US011633593B2

(12) United States Patent
John et al.

(10) Patent No.: US 11,633,593 B2
(45) Date of Patent: Apr. 25, 2023

(54) TREATMENT OF PELVIC FLOOR DISORDERS USING TARGETED LOWER LIMB NERVE STIMULATION

(71) Applicant: EBT MEDICAL, INC., Toronto (CA)

(72) Inventors: Michael Sasha John, Larchmont, NY (US); Paul B. Yoo, Toronto (CA)

(73) Assignee: EBT Medical, Inc., Toronto (CA)

( * ) Notice: Subject to any disclaimer, the term of this patent is extended or adjusted under 35 U.S.C. 154(b) by 358 days.

(21) Appl. No.: 16/734,646

(22) Filed: Jan. 6, 2020

(65) Prior Publication Data

US 2020/0139118 A1   May 7, 2020

Related U.S. Application Data

(63) Continuation-in-part of application No. 14/553,427, filed on Nov. 25, 2014, now Pat. No. 10,549,087.
(Continued)

(51) Int. Cl.
*A61N 1/36* (2006.01)
*A61N 1/04* (2006.01)
(Continued)

(52) U.S. Cl.
CPC ....... *A61N 1/36007* (2013.01); *A61N 1/0456* (2013.01); *A61N 1/0496* (2013.01);
(Continued)

(58) Field of Classification Search
None
See application file for complete search history.

(56) References Cited

U.S. PATENT DOCUMENTS 5,003,978 A * 4/1991 Dunseath, Jr. ......... A61B 5/411
600/391
5,193,539 A    3/1993 Schulman et al.
(Continued)

FOREIGN PATENT DOCUMENTS

CA    2509338 A1    6/2004
CA    2931799 A1    6/2015
(Continued)

OTHER PUBLICATIONS

Badia et al. "Comparative analysis of transverse intrafascicular multichannel, longitudinal intrafascicular and multipolar cuff electrodes for the selective stimulation of nerve fascicles." J. Neural Eng. 8(3), p. 036023 (May 2011). doi:10.1088/1741-2560/8/3/036023.
(Continued)

*Primary Examiner* — Erica S Lee
(74) *Attorney, Agent, or Firm* — Rosenberg, Klein & Lee

(57) ABSTRACT

Methods and systems for improving nerve stimulation are disclosed which relate to shaping characteristics of the stimulation field such as by using different geometries and locations of stimulation. In embodiments, systems and methods are provided to improve selective modulation of specific targeted neural substrate, while minimizing the activation of adjacent non-targeted nervous tissue. While aspects of the disclosed technologies can be applied to any part of the central and peripheral nervous systems for treatment various disorders and providing symptom relief to provide for therapy related to pelvic floor disorders such as overactive bladder.

22 Claims, 43 Drawing Sheets

Related U.S. Application Data

(60) Provisional application No. 62/024,912, filed on Jul. 15, 2014, provisional application No. 61/944,744, filed on Feb. 26, 2014, provisional application No. 61/909,679, filed on Nov. 27, 2013.

(51) Int. Cl.
- *A61N 1/40* (2006.01)
- *A61N 2/00* (2006.01)
- *A61N 7/00* (2006.01)

(52) U.S. Cl.
CPC .............. *A61N 1/40* (2013.01); *A61N 2/002* (2013.01); *A61N 2/006* (2013.01); *A61N 7/00* (2013.01); *A61N 2007/0026* (2013.01)

(56) References Cited

U.S. PATENT DOCUMENTS

| | | |
|---|---|---|
| 6,205,359 B1 | 3/2001 | Boveja |
| 6,314,324 B1 | 11/2001 | Lattner et al. |
| 6,453,204 B1 | 9/2002 | Rhodes |
| 6,493,588 B1 | 12/2002 | Malaney et al. |
| 6,941,171 B2 | 9/2005 | Mann et al. |
| 6,993,392 B2 | 1/2006 | Nicolelis et al. |
| 7,054,689 B1 | 5/2006 | Whitehurst et al. |
| 7,294,101 B2 | 11/2007 | Fischell et al. |
| 7,590,453 B2 | 9/2009 | Heruth et al. |
| 7,668,598 B2 | 2/2010 | Herregraven et al. |
| 7,729,772 B2 | 6/2010 | Williams et al. |
| 8,012,189 B1 | 9/2011 | Webb et al. |
| 8,046,082 B2 | 10/2011 | Herregraven et al. |
| 8,052,591 B2 | 11/2011 | Mishelevich et al. |
| 8,262,556 B2 | 9/2012 | Fischell et al. |
| 8,332,029 B2 | 12/2012 | Glukhovsky et al. |
| 8,435,166 B2 | 5/2013 | Burnett et al. |
| 8,509,920 B2 | 8/2013 | Wahlstrand et al. |
| 8,660,646 B2 | 2/2014 | Laing et al. |
| 8,676,324 B2 | 3/2014 | Simon et al. |
| 8,715,327 B1 | 5/2014 | Lovett et al. |
| 8,788,045 B2 | 7/2014 | Gross et al. |
| 8,812,114 B2 | 8/2014 | Van Den Biggelaar et al. |
| 9,056,194 B2 | 6/2015 | Van Den Biggelaar et al. |
| 9,084,897 B2 | 7/2015 | Yonce |
| 9,265,941 B2 | 2/2016 | Van Den Biggelaar et al. |
| 2001/0025192 A1 | 9/2001 | Gerber et al. |
| 2003/0074037 A1 | 4/2003 | Moore et al. |
| 2003/0187483 A1 | 10/2003 | Grey et al. |
| 2003/0233126 A1 | 12/2003 | Kaplan et al. |
| 2004/0122477 A1 | 6/2004 | Whitehurst et al. |
| 2004/0204962 A1 | 10/2004 | Howser et al. |
| 2005/0143789 A1 | 6/2005 | Whitehurst et al. |
| 2006/0184211 A1 | 8/2006 | Gaunt et al. |
| 2007/0185541 A1 | 8/2007 | DiUbaldi et al. |
| 2008/0154334 A1 | 6/2008 | Gavronsky |
| 2008/0234782 A1 | 9/2008 | Haugland et al. |
| 2008/0306325 A1 | 12/2008 | Burnett et al. |
| 2008/0319272 A1 | 12/2008 | Patangay et al. |
| 2009/0198293 A1 | 8/2009 | Cauller et al. |
| 2009/0210042 A1 | 8/2009 | Kowalczewski |
| 2009/0326602 A1 | 12/2009 | Glukhovsky et al. |
| 2010/0130867 A1 | 5/2010 | Vercellotti et al. |
| 2010/0152808 A1 | 6/2010 | Boggs |
| 2010/0217349 A1 | 8/2010 | Fahey |
| 2010/0292769 A1 | 11/2010 | Braunstein et al. |
| 2011/0054565 A1 | 3/2011 | Wacnik et al. |
| 2011/0112601 A1 | 5/2011 | Meadows et al. |
| 2011/0125203 A1* | 5/2011 | Simon .................... A61N 2/006 607/2 |
| 2011/0190668 A1 | 8/2011 | Mishelevich |
| 2011/0213200 A1 | 9/2011 | Mishelevich |
| 2011/0270138 A1 | 11/2011 | Mishelevich |
| 2012/0101326 A1 | 4/2012 | Simon et al. |
| 2012/0197339 A1 | 8/2012 | Takagi et al. |
| 2012/0197342 A1 | 8/2012 | Towe |
| 2012/0203308 A1 | 8/2012 | Gerber et al. |
| 2012/0265271 A1* | 10/2012 | Goetz .................... A61B 34/20 607/59 |
| 2012/0302912 A1* | 11/2012 | Moffitt ............... A61N 1/36185 607/59 |
| 2013/0006322 A1 | 1/2013 | Tai |
| 2013/0066392 A1 | 3/2013 | Simon et al. |
| 2013/0079843 A1 | 3/2013 | Mashiach |
| 2013/0085545 A1 | 4/2013 | Mashiach |
| 2013/0096656 A1 | 4/2013 | Towe et al. |
| 2013/0123877 A1 | 5/2013 | Rezai |
| 2013/0150696 A1 | 6/2013 | Han et al. |
| 2013/0268023 A1 | 10/2013 | Jahns |
| 2013/0289659 A1 | 10/2013 | Nelson et al. |
| 2013/0310895 A1 | 11/2013 | Pless et al. |
| 2013/0317281 A1 | 11/2013 | Schneider et al. |
| 2013/0325095 A1 | 12/2013 | Ollivier |
| 2014/0031837 A1 | 1/2014 | Perryman et al. |
| 2014/0046423 A1 | 2/2014 | Rajguru et al. |
| 2014/0081363 A1 | 3/2014 | Clark et al. |
| 2014/0088664 A1 | 3/2014 | Sharma et al. |
| 2014/0094720 A1 | 4/2014 | Tyler |
| 2014/0194726 A1 | 7/2014 | Mishelevich et al. |
| 2014/0214128 A1 | 7/2014 | Peterson et al. |
| 2014/0214144 A1 | 7/2014 | Peterson et al. |
| 2014/0247438 A1 | 9/2014 | Hotzel |
| 2014/0296935 A1 | 10/2014 | Ferree et al. |
| 2014/0316499 A1 | 10/2014 | Towe et al. |
| 2014/0324133 A1 | 10/2014 | Deisseroth et al. |
| 2014/0324144 A1 | 10/2014 | Ye et al. |
| 2014/0343656 A1 | 11/2014 | Wechter |
| 2015/0025422 A1 | 1/2015 | Tyler |
| 2015/0073505 A1 | 3/2015 | Errico et al. |
| 2015/0127059 A1 | 5/2015 | Errico et al. |
| 2015/0148862 A1 | 5/2015 | Simon et al. |
| 2015/0148864 A1 | 5/2015 | Peterson et al. |
| 2015/0148878 A1 | 5/2015 | Yoo et al. |

FOREIGN PATENT DOCUMENTS

| | | |
|---|---|---|
| EP | 1981589 B1 | 10/2008 |
| JP | 2006521861 A | 9/2006 |
| JP | 2011526180 A | 10/2011 |
| JP | 2012217565 A | 11/2012 |
| WO | 2005070494 A1 | 8/2005 |
| WO | 2014127091 A1 | 8/2014 |
| WO | 2014153219 A1 | 9/2014 |
| WO | 2016106182 A1 | 6/2016 |
| WO | 2017044904 A1 | 3/2017 |

OTHER PUBLICATIONS

Benzon et al. "Comparison of the different approaches to saphenous nerve block." Anesthesiology 102(3), pp. 633-638 (Mar. 2005). doi:10.1097/00000542-200503000-00023.

Breeders et al. "Endogenous ways to stimulate brown adipose tissue in humans." Ann. Med. 47(2), pp. 123-132 (Feb. 2014). doi:10.3109/07853890.2013.874663.

De Bock et al. "Evaluating the use of different waveforms for intravesical electrical stimulation: a study in the rat." Neurourol. Urodyn. 30(1), pp. 169-173 (Dec. 2010). doi:10.1002/nau.20889.

Fang & Mortimer. "Selective activation of small motor axons by quasi-trapezoidal current pulses." IEEE Trans. Biomed. Eng. 38(2), pp. 168-174 (Feb. 1991). doi:10.1109/10.76383.

Hsu et al. "Effect of neuromuscular electrical muscle stimulation on energy expenditure in healthy adults." Sensors 11(2), pp. 1932-1942 (Feb. 2011). doi:10.3390/s110201932.

Kilgore & Bhadra. "Nerve conduction block utilising high-frequency alternating current." Med. Biol. Eng. Comput. 42(3), pp. 394-406 (May 2004). doi:10.1007/BF02344716.

Kimura. "Electrodiagnosis in Disease of Nerve and Muscle: Principles and Practice." Chapter 6: "Assessment of Individual Nerves." pp. 130-177, Oxford University Press (3d ed., Feb. 2001). ISBN-13:978-0195129779.

Koga et al. "Selective activation of primary afferent fibers evaluated by sine-wave electrical stimulation." Mol. Pain 1(13) (Mar. 2005). doi:10.1186/1744-8069-1-13.

(56) References Cited

OTHER PUBLICATIONS

Kovacevic & Yoo. "Reflex neuromodulation of bladder function elicited by posterior tibial nerve stimulation in anesthetized rats." Am. J. Physiol. Renal Physiol. 308(4), F320-F329 (Nov. 2014). doi:10.1152/ajprenal.00212.2014.

Lee et al. "First human demonstration of cardiac stimulation with transcutaneous ultrasound energy delivery: implications for wireless pacing with implantable devices." J Am. Coll. Cardiol. 50(9), pp. 877-883 (Aug. 2007). doi:10.1016/j.jacc.2007.04.081.

Peng et al. "Role of pudendal afferents in voiding efficiency in the rat." Am. J. Physiol. Regul. Integr. Comp. Physiol. 294(2), R660-R672 (Dec. 2007). doi:10.1152/ajpregu.00270.2007.

Phillips & Park. "Electrophysiological mapping of the segmental innervation of the saphenous and sural nerves." Muscle Nerve 16(8), pp. 827-831 (Aug. 1993). doi:10.1002/mus.880160804.

Rattay. "Analysis of models for extracellular fiber stimulation." IEEE Trans. Biomed. Eng. 36(7), pp. 676-682 (Jul. 1989). doi:10.1109/10.32099.

Ruiz-Tovar et al. "Percutaneous electrical neurostimulation of dermatome T6 for appetite reduction and weight loss in morbidly obese patients." Obes. Surg. 24(2), pp. 205-211 (Feb. 2014). doi:10.1007/s11695-013-1091-z.

Schukro et al. "The effects of auricular electroacupuncture on obesity in female patients—A prospective randomized placebo-controlled pilot study." Complement. Ther. Med. 22(1), pp. 21-25 (Oct. 2013). doi:10.1016/j.ctim.2013.10.002.

Schulte et al. "Loss of vagal tone aggravates systemic inflammation and cardiac impairment in endotoxemic rats." J. Surg. Res. 188(2), pp. 480-488 (Jan. 2014). doi:10.1016/j.jss.2014.01.022.

Su et al. "Comparison of neural targets for neuromodulation of bladder micturition reflex in the rat." AJP Ren. Physiol. 303(8), F1196-F1206 (Aug. 2012). doi:10.1152/ajprenal.00343.2012.

Su et al. "Differentiation and interaction of tibial versus spinal nerve stimulation for micturition control in the rat." Neurourol. Urodyn. 34(1), pp. 92-97 (Oct. 2013). doi:10.1002/nau.22506.

Su et al. "Quantification of effectiveness of bilateral and unilateral neuromodulation in the rat bladder rhythmic contraction model." BMC Urol. 13(34) (Jul. 2013). doi:10.1186/1471-2490-13-34.

Su et al. "Role of the endogenous opioid system in modulation of urinary bladder activity by spinal nerve stimulation." AJP Renal Physiol. 305(1), F52-F60 (Jul. 2013). doi:10.1152/ajprenal.00090.2013.

Tam et al. "Brown adipose tissue: Mechanisms and potential therapeutic targets." Circulation 125(22), pp. 2782-2791 (Jun. 2012). doi:10.1161/CIRCULATIONAHA.111.042929.

Tanaka et al. "Comparison of premodulated interferential and pulsed current electrical stimulation in prevention of deep muscle atrophy in rats." J. Mol. Histol. 44, pp. 203-211 (Dec. 2012). doi:10.1007/s10735-012-9473-4.

Wilmot & Evans. "Categorizing the distribution of the saphenous nerve in relation to the great saphenous vein." Clin. Anat. 26(4), pp. 531-536 (May 2013). doi:10.1002/ca.22168.

Yoneshiro et al. "Recruited brown adipose tissue as an antiobesity agent in humans." J. Clin. Invest. 123(8), pp. 3404-3408 (Aug. 2013). doi:10.1172/JCI67803.

Yoo & Durand. "Selective recording of the canine hypoglossal nerve using a multicontact flat interface nerve electrode." IEEE Trans. Biomed. Eng. 52(8), pp. 1461-1469 (Aug. 2005). doi:10.1109/TBME.2005.851482.

Yoo et al. "Selective stimulation of the canine hypoglossal nerve using a multi-contact cuff electrode." Ann. Biomed. Eng. 32(4), pp. 511-519 (Apr. 2004). doi:10.1023/b:abme.0000019170.74375.fb.

International Search Report and Written Opinion for related PCT Application No. PCT/IB2014/003041, dated May 31, 2016.

International Search Report and Written Opinion for related PCT Application No. PCT/CA2016/050575, dated Nov. 21, 2017.

International Search Report and Written Opinion for related PCT Application No. PCT/CA2017/050971, dated Nov. 3, 2017.

Examination Report for related Australian Application No. 2016265904, dated Apr. 1, 2020.

Examination Report for related Australian Application No. 2016265904, dated Jan. 27, 2021.

Examiner's Requisition and Search Report for related Canadian Application No. 2986467, dated Apr. 11, 2018.

Examiner's Requisition and Search Report for related Canadian Application No. 2986467, dated Jul. 27, 2018.

Examiner's Requisition and Search Report for related Canadian Application No. 2986467, dated Nov. 26, 2019.

Examiner's Requisition and Search Report for related Canadian Application No. 2931799, dated Jan. 4, 2021.

Office Action and Search Report for related Chinese Application No. 201680042787.5, dated Jul. 29, 2020.

Office Action for related Chinese Application No. 201680042787.5, dated Dec. 29, 2020.

Examination and Search Report for related European Application No. 14865099.7, dated Jun. 6, 2017.

Examination and Search Report for related European Application No. 14865099.7, dated May 29, 2020.

Refusal of related Japanese Application No. 2018-512457, dated Jun. 16, 2020.

Refusal of related Japanese Application No. 2018-512457, dated Jan. 18, 2021.

* cited by examiner

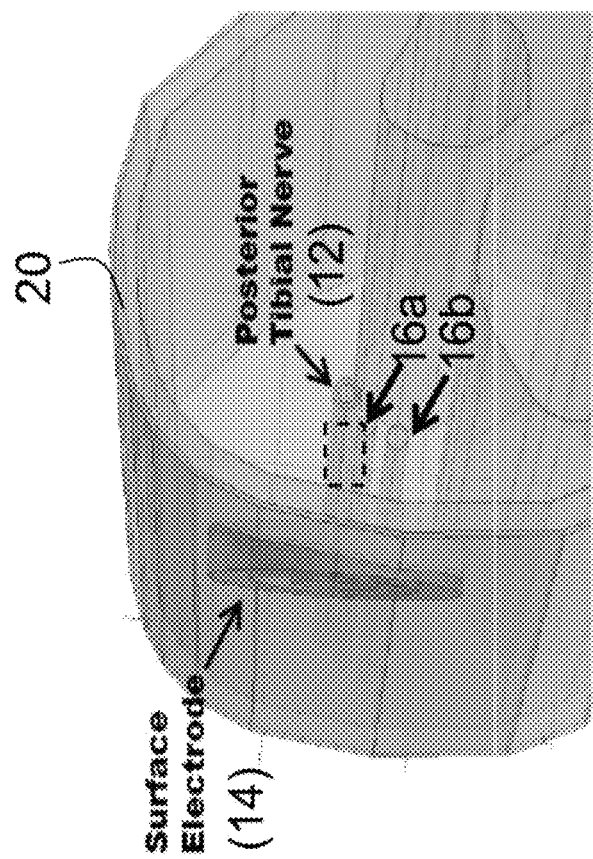
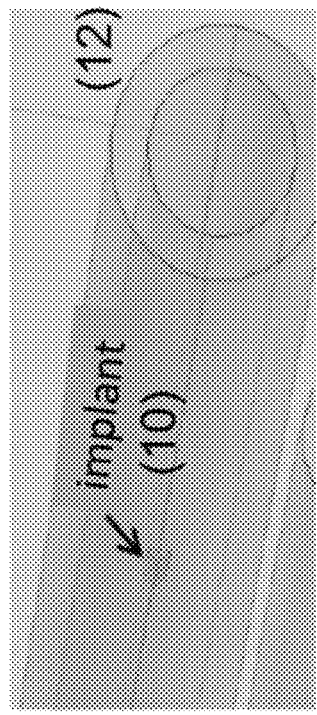
Fig. 1a
Fig. 1b

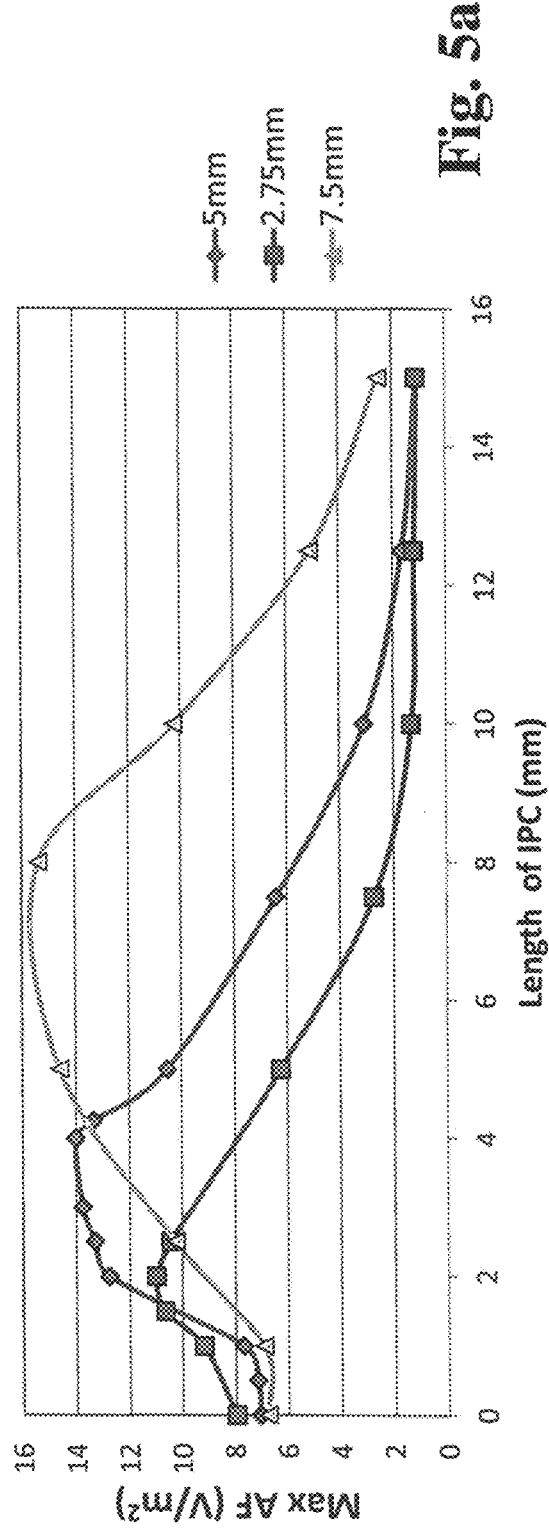
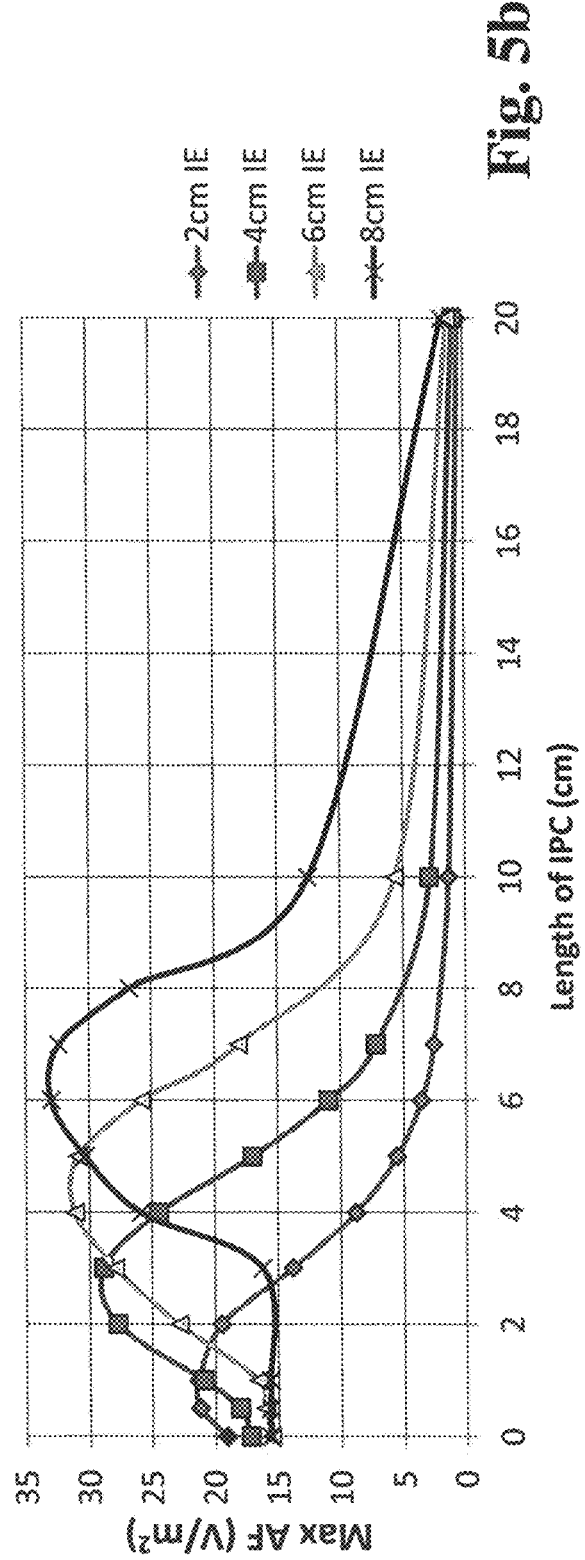

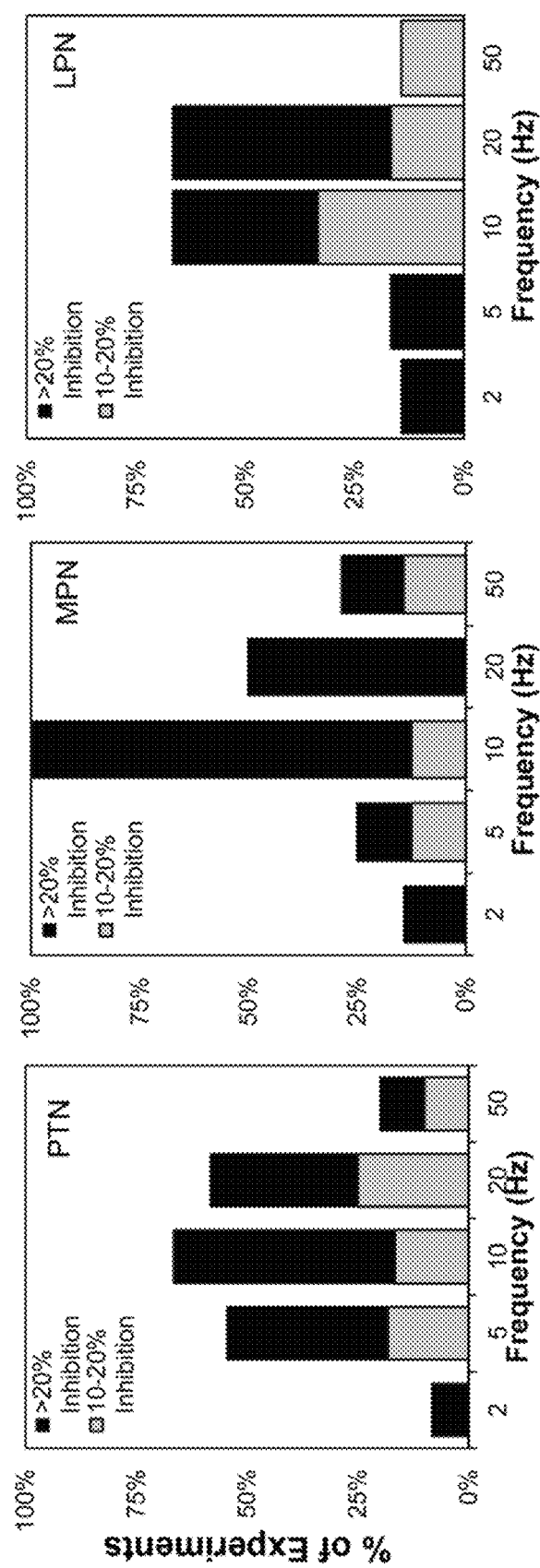

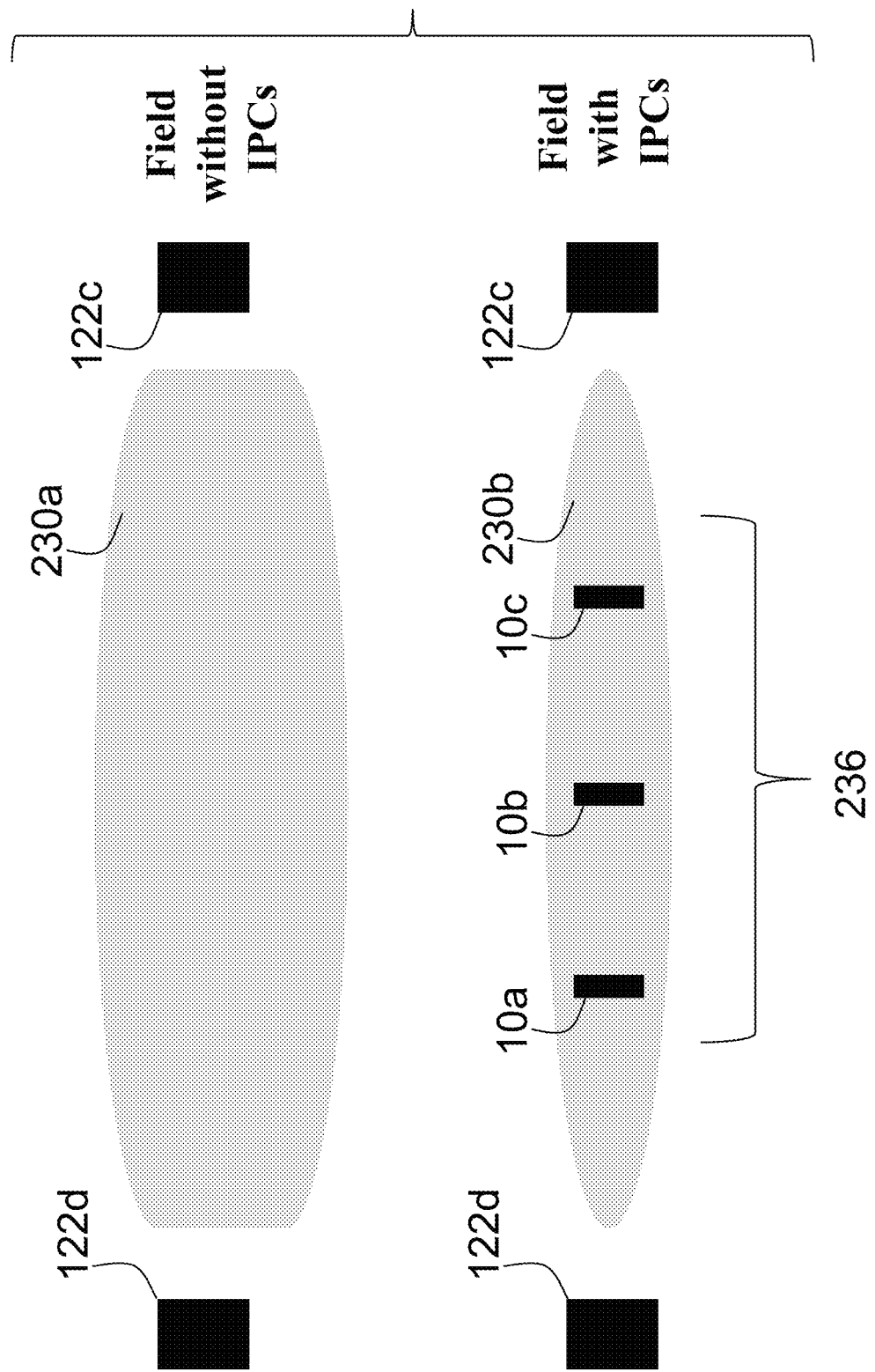

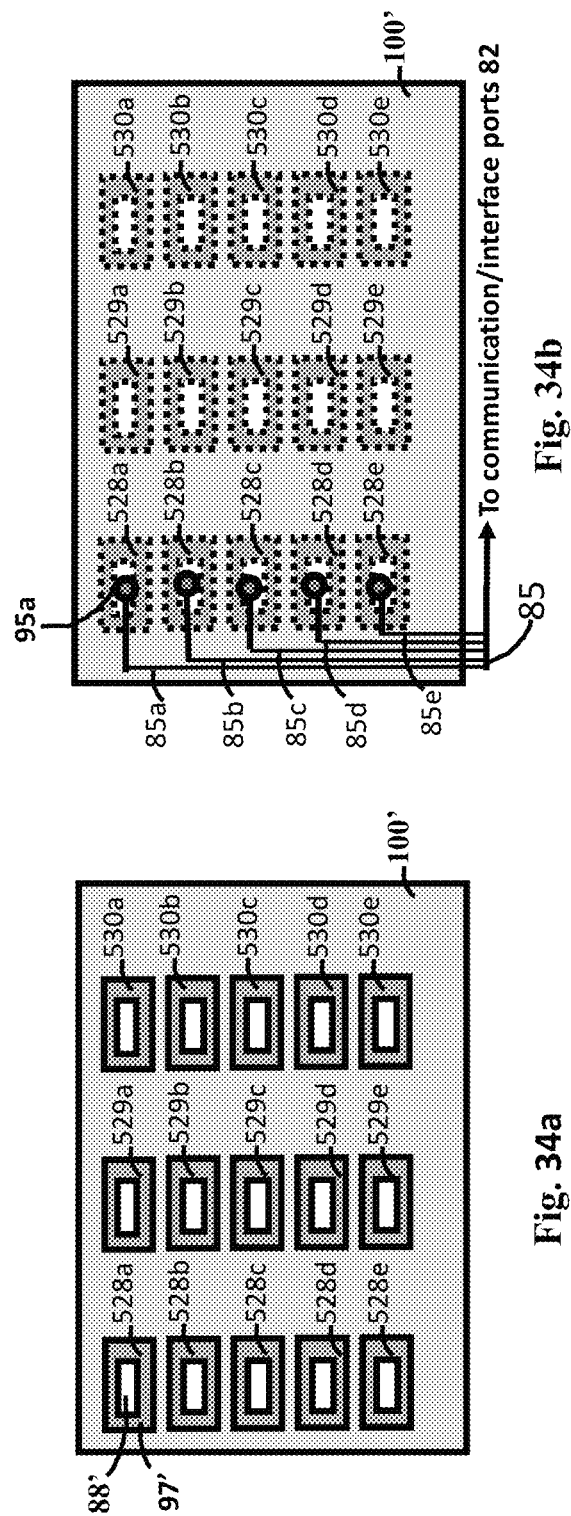

TREATMENT OF PELVIC FLOOR DISORDERS USING TARGETED LOWER LIMB NERVE STIMULATION

REFERENCE TO RELATED APPLICATIONS

This Patent Application is a continuation-in part of patent application U.S. Ser. No. 14/553,427 filed Nov. 25, 2014, entitled Systems and Methods of Enhancing Electrical Activation of Nervous Tissue, based on Provisional Patent Application Ser. No. 61/909,679, filed 27 Nov. 2013, now expired; Provisional Patent Application Ser. No. 61/944,744, filed 26 Feb. 2014, now expired; and, Provisional Patent Application Ser. No. 62/024,912, filed 15 Jul. 2014, now expired.

FIELD OF THE INVENTION

The subject concept relates to the field of modulating biological tissue.

In particular the subject concept pertains to the field of modulating nerve tissue.

BACKGROUND OF THE INVENTION

Nerve stimulation (neurostimulation) technology includes applications such as electrical neuromodulation, functional electrical stimulation, and therapeutic electrical stimulation. Nerve stimulation is an effective clinical tool used to treat various chronic medical disorders and conditions. Examples include (1) deep brain stimulation (DBS) for treating Parkinson's disease and essential tremor, (2) spinal cord stimulation for pain and urinary dysfunction, and (3) peripheral nerve stimulation for overactive bladder, pain, obstructive sleep apnea, headache, migraine, epilepsy, depression, hypertension, chronic heart failure, and stroke rehabilitation. Peripheral nerves may include, for example, the vagus nerve, occipital nerve, cranial nerves, spinal nerves, pudendal nerves, cutaneous nerves, and the sciatic nerve.

Therapeutic efficacy of neurostimulation technology is attributed to selective activation of targeted tissue or neural circuitry. This is achieved by low recruitment of non-targeted tissue or neural circuit(s). Unintended activation of non-targeted nervous tissue, by a broad or incorrectly localized stimulation field, may deter therapeutic benefit. Unintended modulation of biological system(s) may also be due to, for example, inhibitory rather than, or in addition to, excitatory effects, or other unwanted activity or physiological responses. Unintended modulation may produce side-effects and outcomes that are contrary to the intended response.

PRIOR ART

The state-of-the-art method, for addressing the issue of selective nerve activation, is to minimize the distance between a stimulating electrode and the nerve targets, and in certain cases isolate the electrode with insulating material. This usually requires precise implantation of an electrode, connecting wires, and a pulse generator (e.g., for brain or spinal cord stimulation). This solution may involve highly-invasive surgery that may be associated with significant risk and discomfort. Disadvantages may include neural or vascular damage, revision surgeries, periodic replacement of pulse generator, surgical complications, and potentially life-threatening infections.

The peripheral nervous system provides a neural substrate that is relatively conducive for selective nerve stimulation of individual nerve branches. However, long-term viability of permanently implanted neurostimulation systems can become complicated by issues related to repeated mechanical movement of lead wires connected to the pulse generator (e.g., lead fracture and/or component migration). Although transcutaneous electrical stimulation can provide a more simple and non-invasive approach, selective nerve activation is not readily achieved.

In many instances, the ability to selectively activate a specific neural target by implanted nerve stimulation systems is also far from ideal when systems with multiple components must be implanted. The current-state-of-the-art methods aimed at improving stimulation selectivity involve the design and implementation of various types of neural interfaces: multi-polar (or multi-contact) deep brain stimulation DBS leads, multi-polar paddle-type electrodes for spinal cord or subcutaneous stimulation, microelectrode arrays (e.g., Utah Array or Michigan Probe, or Huntington Medical Research Institute electrodes), and multi-contact nerve cuff electrodes (e.g., Cyberonics Inc., Case Western Reserve University). A main objective of these electrode designs is to maximize the number of electrode contacts such that an 'optimally-positioned' stimulation location, or an 'optimal combination of one or more electrode contacts', can be used to achieve effective therapeutic outcomes. Improved nerve stimulation selectivity can increase the efficacy of treatment in some instances, such as unintended stimulation of adjacent nerves.

Advances in minimally-invasive nerve stimulation have been realized clinically. Wireless implantable electrode probes have been developed for achieving less invasive methods of selective nerve stimulation. The BION (Alfred Mann Foundation, Boston Scientific) is a glass or ceramic covered electrode that can be percutaneously injected into a region of interest. It can be self-powered or passively charged by radio frequency (RF) pulses. Long-term use may be complicated by migration of the BION from its original implant location. This migration may cause both reduced therapeutic effects and increased stimulation-evoked side effects due to activation of other (non-target) tissue. Nerve stimulation systems (e.g., MicroTransponder Inc. SAINT™ System) which are smaller, less expensive, and less technically complicated than the BION may be advantageous in treatment of some disorders.

Another example of nerve stimulation technology is the floating light-activated micro-electrode (FLAME). FLAME uses an analogous design approach to the BION however, instead of RF pulses, the implanted electrode converts near infrared light into electrical pulses. Clinical use of FLAME technology is currently limited, primarily due to poor penetration of light into biological tissue and other technical hurdles.

Transcutaneous magnetic stimulators (TMS), termed "transcranial magnetic stimulators" when used for brain stimulation, are used to treat disorders such as migraine (e.g. Neuralieve Inc.) by using an external magnetic stimulation device to stimulate central or peripheral tissue targets. The fields induced inside the tissue by one or more pulses (pulsed electromagnetic stimulation) may be less localized than desired.

Transcutaneous electrical nerve stimulation (TENS) is another non-invasive approach to activating nervous tissue. Companies such as Cefaly have designed TENS systems to work specifically on nerve cells affected by pain. The TENS system developed by Cefaly works by introducing electric impulses to act on the nerves that transmit migraine pain such as a bifurcation of nerves known as the trigeminal nerve. In addition to pain, TENS systems have been used to apply electrical fields to the brain in order to modulate sleep, anxiety, depression, pain, attention, memory, and other types of cognitive/sensory processing. The current system and method may be used with such a TENS system in order to focus on an area, or population, of nerves that are electrically activated.

Electrocore Inc. has developed both non-invasive electrical (e.g., TENS) and implantable magnetically driven stimulators that electrically stimulate nerves such as the vagus nerve. For vagus nerve stimulation (VNS) therapy, a handheld device is placed on the surface of the skin just above the vagus nerve, which is palpated by the pulsating carotid artery. The clinical efficacy of this approach is currently undergoing validation. Given the anatomical characteristics of the vagus nerve (e.g., distance from the skin surface, embedded within a neurovascular bundle), there may be challenges associated with TENS based VNS. Factors such as overweight patients with subcutaneous tissue (e.g., fat deposits) may prove challenging since this increases the distance between the stimulating electrode and the vagal target.

Uroplasty has developed both cutaneous and percutaneous stimulation systems for the treatment of urological disorders. The main therapy currently implemented involves posterior tibial nerve stimulation, which relies on percutaneous injection of a needle electrode near the patient's ankle.

Both Electrocore Inc and Uroplasty are currently engaged in developing implantable stimulation systems for activating nervous tissue, where the implanted stimulator is wirelessly powered by magnetic induction. This approach obviates the need for using an implantable battery, percutaneous or sub-cutaneous leads connecting to a power source, and it may also decrease the complexity of the implanted circuitry. This system has not yet completed clinically trials, and so the associated disadvantages are currently unknown. Modulation of biological tissue, such as nervous tissue, presents the opportunity to treat a myriad of biological and physiological conditions and disorders. Modulation can include interacting with, and controlling, a patient's natural processes. Modulation of tissue can include nerve modulation such as inhibition (e.g. blockage), activation, modification, up-regulation, down-regulation, or other type of therapeutic alteration of activity. The resulting biological response may be electrical or chemical in nature and may occur within the central or peripheral nervous systems, or the autonomic or somatic nervous systems. By modulating the activity of the nervous system, for example, through activation or blocking of nerves, many functional outcomes may be achieved. Motor neurons may be stimulated to cause muscle contractions. Sensory neurons may be blocked, to relieve pain, or stimulated, to provide a biofeedback signal to a subject. In other examples, modulation of the autonomic nervous system may be used to adjust various involuntary physiological parameters, such as heart rate and blood pressure.

SUMMARY

A transcutaneous tissue stimulation system and method is provided which includes an electrical generator positioned external to a patient. A stimulator is electrically coupled to the electrical generator and is positioned on the surface of the patient's skin. An implanted electrically conductive member is positioned on or contiguous to a target nerve tissue for stimulation of the target nerve tissue to modify the electrical field signals generated by the electrical generator and provided by the stimulator for the purpose of modulating signals from the nerve tissue to the brain, to the central or peripheral nervous system, or other target, of the patient.

Stimulation systems and methods are described for providing advantages related to increasing therapeutic efficacy of nerve stimulation, improving the comfort of a patient relative to other therapeutic solutions, decreasing the cost of treatment, and/or providing for a simple treatment and/or implantation procedure.

One objective of the current system is to provide systems and methods which provide selective nerve stimulation, and stimulate specific nerve branches or selected portions of a nerve.

Another objective of the current system is to provide one or more small implanted components to provide selective nerve stimulation and thereby offer improved long-term clinical therapy. This system and method aims to avoid activation of non-targeted nervous tissue, which can both limit the overall therapeutic effects and exacerbate stimulation-evoked side effects.

Another objective of the current system and method is to provide for a nerve stimulation system having external components and an implanted passive element which is configured to allow therapy to achieve the same, or improved therapeutic benefit as that which would otherwise be achieved when using only transcutaneous nerve stimulation without an implanted passive element.

Another objective is to provide systems and methods for providing stimulation of tissue using complementary or "paired" configurations of external stimulation elements and subcutaneously implanted passive elements.

Another objective is to provide systems and methods for providing a selective increase in neural excitability, where a single neural target (located among one or more other nerves) is independently activated or multiple nerves are activated independently using one or more implanted elements and applying different stimulation parameters such as stimulator location, amplitude, frequency, duty cycle, and waveform.

Another objective is to provide systems and methods for achieving effective therapeutic nerve activation with relatively lower stimulation amplitude and/or shorter pulse width than what is achievable using prior art methods (e.g., TENS).

Another objective is to provide systems and methods for reduced activation of non-targeted nervous tissue (i.e., minimize stimulation spillover).

Another objective is to provide systems and methods for decreasing nerve stimulation-evoked side effects.

Another objective is to provide systems and methods for providing improved transcutaneous electrical nerve stimulation, intra-vascular stimulation of nervous tissue, and augmented selective activation of peripheral and central nervous system tissue.

Another objective is to provide systems and methods for providing improved TENS for certain fibers during VNS (e.g., small myelinated B-fibers and/or unmyelinated C-fibers), while avoiding, for example, A-Type fibers.

Another objective is to provide systems and methods for providing improved modulation of tissue targets that may include glandular tissue, fatty or lipid tissue, bone tissue, muscle tissue, and nerve tissue.

Another objective is to provide systems and methods for improving a number of clinical conditions and their related treatments including, for example: a) Overactive Bladder treatment (or any disorder or condition related to bladder activity or voiding including pelvic floor disorders) by posterior tibial nerve or sacral nerve stimulation; b) Chronic pain and treatment by stimulation of the lower back or lower extremities; c) treatment related to migraine and headache; d) Obstructive sleep apnea and treatment related to hypoglossal, vagal, or superior larygeal nerve stimulation; e) various conditions such as epilepsy and depression which may be treated by vagus nerve stimulation; and f) various other conditions that may be treated by improving selective targeting of specific tissue.

Another objective is to provide systems and methods for providing stimulation of tissue using improved configurations, materials, orientations, embodiments, and spacing of external stimulation elements, cutaneous stimulation elements, and implanted passive elements which are not physically connected to the stimulation sources.

Another objective is to provide systems and methods for providing stimulation of a first tissue target that is approximately cutaneous and also providing for stimulation of a second target that is a nerve that is relatively distal from the skin surface.

Another objective is to provide systems and methods for augmenting other therapies in order to increase the number of patients that benefit, augment the magnitude of therapeutic benefits, and/or decrease the frequency of repeated therapeutic interventions that may be significantly more invasive.

A further object of the subject system and method is to allow magnetically-induced electric fields to achieve more specific modulation of tissue or neural circuits.

A further object of the system and method is to permit a functional focusing and/or shaping of a TMS field so that selective activation is promoted.

A still further object of the system and method is to permit use with a TENS system to focus the area or population of nerves that is electrically activated.

These and other objectives and advantages of the invention will now be disclosed in the figures, detailed description, and claims of the invention.

In the illustrated embodiments, any steps shown in the figures may occur in a different order, may be repeated, may lead to different steps of the method shown within each figure, or may lead to steps shown in other figures, may be included or excluded from a particular embodiment, and this may occur conditionally, or according to the desires of a patient, doctor, remote medical service, or caregiver.

BRIEF DESCRIPTION OF THE FIGURES

FIGS. 1a-1b show a schematic diagram of one embodiment of an enhanced transcutaneous nerve stimulation (eTNS) system implemented in a lower limb, where the system, or finite element model thereof, includes a surface electrode, and a passive element (implantable passive component or "IPC") that is placed in close proximity to the posterior tibial nerve, and FIG. 1b is a close-up of the area enclosed by the dashed box of FIG. 1a.

FIG. 5a is a graph of data from computer simulations, (finite element model of FIG. 1a scaled to dimensions of a rat), that depict the relationship between the length of the IPC (cuff-type) and the distance between the bipolar stimulating surface electrodes (similar to the setup shown in FIG. 1c).

FIG. 5b is a graph of data from computer simulations (finite element model of FIG. 1a scaled to dimensions of a human) of enhanced transcutaneous nerve stimulation (eTENS) that are in agreement with findings from an experimental rat model (i.e., result of FIG. 5a).

FIGS. 14a, b, c are graphs of summary data of percentage of experiments (total 11 rats) that exhibited an acute reduction in BRC (i.e. acute bladder inhibition) during each 10-minute stimulation trial of the PTN, MPN, and LPN in anesthetized rats.

FIG. 23a is a schematic diagram of an embodiment of the subject system in which a plurality of IPCs provides for the shaping of an electrical field.

FIGS. 34a and 34b show the upper and lower surfaces of an electrode grid array.

DETAILED DESCRIPTION OF THE PREFERRED EMBODIMENTS

Figure 1C:
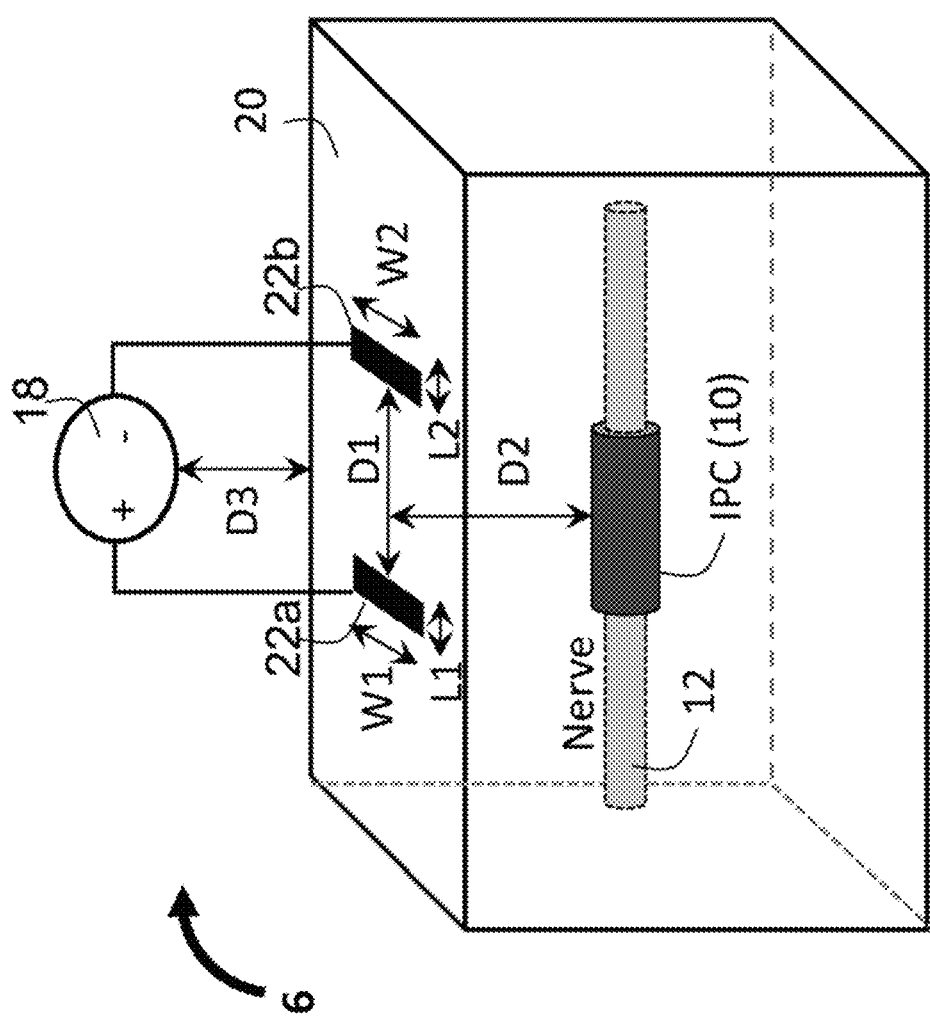
FIG. 1c shows another embodiment of the enhanced nerve stimulation system, or finite element model thereof, and includes a pair of stimulating surface electrodes (bipolar stimulation), with lengths (L1, L2) and widths (W1, W2), placed on the surface of the skin of a patient, with an inter-electrode distance (D1), as well as an implant located at a given depth distance (D2) from the skin surface.

Reference will now be made in detail to exemplary embodiments of the present disclosure, examples of which are illustrated in the accompanying drawings. Wherever possible, the same reference numbers will be used throughout the drawings to refer to the same or like parts. When titles are provided to the different sections of the disclosure these are provided to highlight certain themes in the application and are not meant to constrain or limit the invention concept in any manner.

Embodiments of the present disclosure relate generally to systems and methods for modulating tissue through the delivery of energy. Tissue modulation/stimulation, which includes nerve or neural modulation, can cause for example, inhibition (e.g. blockage), excitation, modification, regulation, and/or therapeutic alteration of activity and patterns of activity. These changes can occur in the central, peripheral, or autonomic nervous systems. Tissue modulation may include providing energy to the tissue to create a voltage change, and in the case of a nerve can be sufficient for the nerve to activate, or propagate an electrical signal (action potential(s)). Nerve modulation/stimulation may also take the form of nerve inhibition, which may include providing energy to the nerve sufficient to prevent the nerve from propagating electrical signals. Nerve inhibition may be performed using approximately continuous or ongoing application of energy, and may also be performed through the application of enough energy to inhibit the function of the nerve for some time after the application. Other forms of neural modulation may modify the function of a nerve, causing for example a heightened or lessened degree of sensitivity. As referred to herein, modulation of a nerve may include modulation of an entire nerve and/or modulation of a portion of a nerve. For example, modulation of a motor neuron may be performed and may only lead to changes in those portions of the neuron that are proximal to, or distal to, the location to which an energy field is applied.

FIGS. 1a and 1b show one embodiment of the invention which is a novel system and method for improving the selective modulation of targeted biological tissue such as various components of the nervous system. FIG. 1a shows a cutaneous surface electrode 14 located near a tissue target 12, such as the posterior tibial nerve. A selective increase in neural excitability (i.e., reduced stimulation threshold) is achieved by placing a biologically-compatible 'implant' 10 in sufficiently close proximity to the targeted neural tissue 12, as shown in FIG. 1b (close-up of the target 12 of FIG. 1a, which shows the implant 10 embedded within the epineurium). Under certain circumstances, presence of this implant 10 can also increase the amount of electrical charge or energy needed to activate non-target nerves 16a, 16b located in the vicinity of the target, thereby supporting increased stimulation selectivity or specificity (note: anatomically, 16a and 16b are posterior tibial vein and artery blood vessels, however in this example we are treating these as non-target nerves for purposes of illustration). The implant 10 (or implantable passive component "IPC") is at least partially electrically conductive, and has at least one conductive portion. The conductive portion is preferably a highly conductive material for promoting electrical nerve activation. The IPC is not physically connected to any electrical power source but rather is positioned to modify the electrical field or power that affects the targeted (nervous) tissue 12. The IPC may be physically secured directly to nerve tissue or surrounding connective tissue, for example, by a suture. The IPC may have a connector portion to assist with its implantation and securing. In one embodiment, the IPC serves to modify the field generated by a cutaneously located stimulator 14.

In another embodiment of the invention which can be used, for example, in order to test and select therapy parameters, the system components and target tissue may be simulated, for example, using a finite element model of the human lower leg. An analogous finite element model of the human lower limb can approximate this scenario by setting the virtual surface electrode at a constant current (e.g., −1 mA, cathode) and the proximal cut surface of the virtual leg as the return (anode). However, in the real world, the return electrode can be placed anywhere on the patient, or alternatively cutaneous (surface) stimulation can be delivered by a pair of electrodes (bipolar configuration). The electrode 14 may be bipolar having both anode and cathode portions (e.g., concentric ring electrodes), with non-conductive material between, or it may be monopolar with the return electrode located at a distal location. FIG. 1a shows an electrode configuration, where the electrode 14 is placed at the level of skin 20 near the IPC 10.

FIG. 1c shows an alternative embodiment of the enhanced nerve stimulation system having at least two surface electrodes 22a, 22b that are placed on the skin surface 20 in a bipolar configuration where one electrode serves as anode (+) and the other as cathode (−). Although, in this example, stimulator lengths L1 and L2 and stimulator widths W1/W2 are set to 5 mm and 2 mm, respectively, the widths and lengths of the two electrodes may be different, and the electrode stimulators may also be of different shapes (rather than both being rectangular). The IPC 10 may be implemented as a cuff-type electrode which is embodied as a hollow cylindrical cuff that completely wraps around a nerve 12, and is in close contact with the outer surface of the nerve. The inter-electrode ("IE") distance is indicated by the D1 double-headed arrow located between the two stimulators 22a, 22b, while depth (distance between the surface stimulators and the IPC) is represented by the D2 double-headed arrow. An electrical source 18 is connected to a pair of cutaneous electrodes that are affixed to a patient's skin 20 near at least one IPC 10. The electrodes may include at least one anode electrode 22a and at least one cathode electrode 22b so that current flows through the tissue between the at least two electrodes and also provides electrical stimulation to target tissue such as nerve 12, and is influenced by at least one IPC, positioned within the patient. As will be shown, certain characteristics of the therapy system (and the corresponding parameters of the model) can influence the ability of the external stimulators 22a, 22b to stimulate the nerve 12. For example, a) the widths W1,W2 and lengths L1, L2 of the surface electrode stimulators 22a, 22b, b) the distance D1 between the two stimulators relative to the length of the IPC, c) the distance D2 between at least one stimulator and the IPC, d) the alignment between the edge of at least one stimulator and at least one edge or "end" of the IPC, e) the distance between the IPC and the nerve, and f) the conductivity of the IPC can all contribute to enhancing the electrical modulation of nervous tissue 12. Other factors such as the thickness, shape, and orientation of the IPC relative to at least one stimulator, may also alter the excitability of the targeted nerve. The system shown in FIG. 1b, illustrates both how it may be implemented physically, when used to modulate nerve activity of a patient, as well as how it may be simulated as a model in order to test and select therapy parameters. In this embodiment, the IPC was modeled as a hollow cylindrical shell placed around and including contact with the outer surface of the nerve.

An embodiment of a method for clinically implementing the system may involve an assessment process which may be termed IPC assessment process, when an IPC is used. The initial step of the process can include creating a computer or physical model which simulates at least one stimulator, the patient and patient tissue, at least one of a target and non-target tissue, and either no IPC or at least one IPC. When two simulations are compared, one in which the IPC is present and one in which the IPC is absent, then the two modeled results may be compared in order to assess the effect of the IPC. In the next step, the model can be adjusted to simulate how a change in each modeled parameter can affect the stimulated tissue, and accordingly suitable stimulation protocols and parameters may be derived for subsequent use in a patient. In a following step, the model and simulated results are then used to customize an improved stimulation system for use with an individual patient. The model parameters can be adjusted based upon patient measurements. For example, patient measurement may include structural and anatomical measurements obtained by physically measuring characteristics of the patient, such as by obtaining sensed data including imaging data related to light/laser, ultrasound, MRI, x-ray or other imaging modality. Patient measurements may also include functional measurements of impedance, bloodflow (e.g. infrared spectroscopy measurements), EMG, data related to muscle (e.g. bladder) contraction, data related to bladder capacity, and the like. The IPC assessment process can be realized in steps 34 and/or 48 of FIG. 17, and/or this process may be done within before, or outside of, the other steps shown in the figure. Patient measurement data can also be used to adjust stimulation protocol parameters and system components, used during therapy, according to individual patients. This can be done to improve therapy and may occur during a step of initial therapy assessment, for example, as in step 250 of FIG. 22c. Patient measurements may be used intermittently (e.g., every 6 months to one year of maintenance PTNS) to confirm proper stimulation settings are maintained or require modifications.

A number of advantages of one aspect of the invention can be demonstrated by computational models. The simulations support the idea of selectively enhancing neural excitability by manipulating the extracellular potential gradient that is generated along the targeted nervous tissue by electrical stimuli. This voltage gradient may be characterized according to a model that is widely referenced in the literature to predict the relative neural excitability (Rattay, F. (1989). "Analysis of models for extracellular fiber stimulation." IEEE Trans Biomed Eng 36(7): 676-682). This is referred to as the 'activating function' (AF) and is defined as the second spatial derivative of the extracellular potential along an axon.

The computationally derived simulation data shown in FIGS. 2a-8, 9b, and 9c were obtained by implementing a 3-dimensional finite element model that consisted of a surface electrode(s), a peripheral nerve (endoneurium, perineurium, and epineurium layers), an IPC (cuff-type hollow cylinder or solid rod), biological tissue (dermis, fat, muscle and bone), and a large saline bath. Electrical stimuli were applied in either a monopolar or bipolar fashion. Monopolar stimulation (modeled as per FIG. 1a) was achieved by setting the surface electrode at the skin interface as the cathode and the surface of the other anatomical objects (e.g., distal cut-end of leg) as the anode. For bipolar stimulation (modeled as per FIG. 1b), one electrode was set as the cathode and the other as the anode. All electrical conductivity values were obtained from the literature (Yoo and Durand, Selective Recording of the Canine Hypoglossal Nerve Using a Multi-contact Flat Interface Nerve Electrode, IEEE Trans. Biomed. Eng., 2004). The resulting extracellular potential (within the endoneurium region) obtained from the finite element model was used to compute the AF of individual nerve fibers. In MATLAB this was calculated as the second spatial difference of extra-cellular potential.

In the absence of an IPC, the electrical stimulation signals provided by the surface electrodes would normally stimulate the neural target tissue 12, and any non-targeted nerves within close proximity to the surface stimulator. It is an advantage of the current invention to provide the IPC to increase neural excitation of targeted nerve(s), and thereby effectively modulate one or multiple neural circuits that produce therapeutic effects. Although the exact mechanisms for the novel phenomenon which is the basis of this aspect of the system and method are not completely understood it may be helpful to conceptualize the system as follows. In one embodiment, the IPC may act to modify the extracellular electric potential generated by the surface electrodes, in order to focus the electrical field (i.e., act as a "lightning rod"), and thereby "enhance" the second spatial derivative of this field along a given target nerve. This enhancement can be seen in relation to changes in the nerve's activating function (AF). The AF is commonly used to quantify the excitation of nervous tissue. In this manner the present invention may serve to provide several advantages such as focusing the field toward an intended tissue target and away from adjacent tissue in order to produce improved therapy with less stimulation-evoked side effects. Another advantage is that the system and method permits the electrical therapy to use less power, at one or more stimulators, in order to supply the therapy and obtain a given effect that is either not normally attainable without more power, or which may not be attainable at all in the absence of the IPC. Using less power at the stimulation site also provides other advantages such as greater patient comfort.

Figure 17:
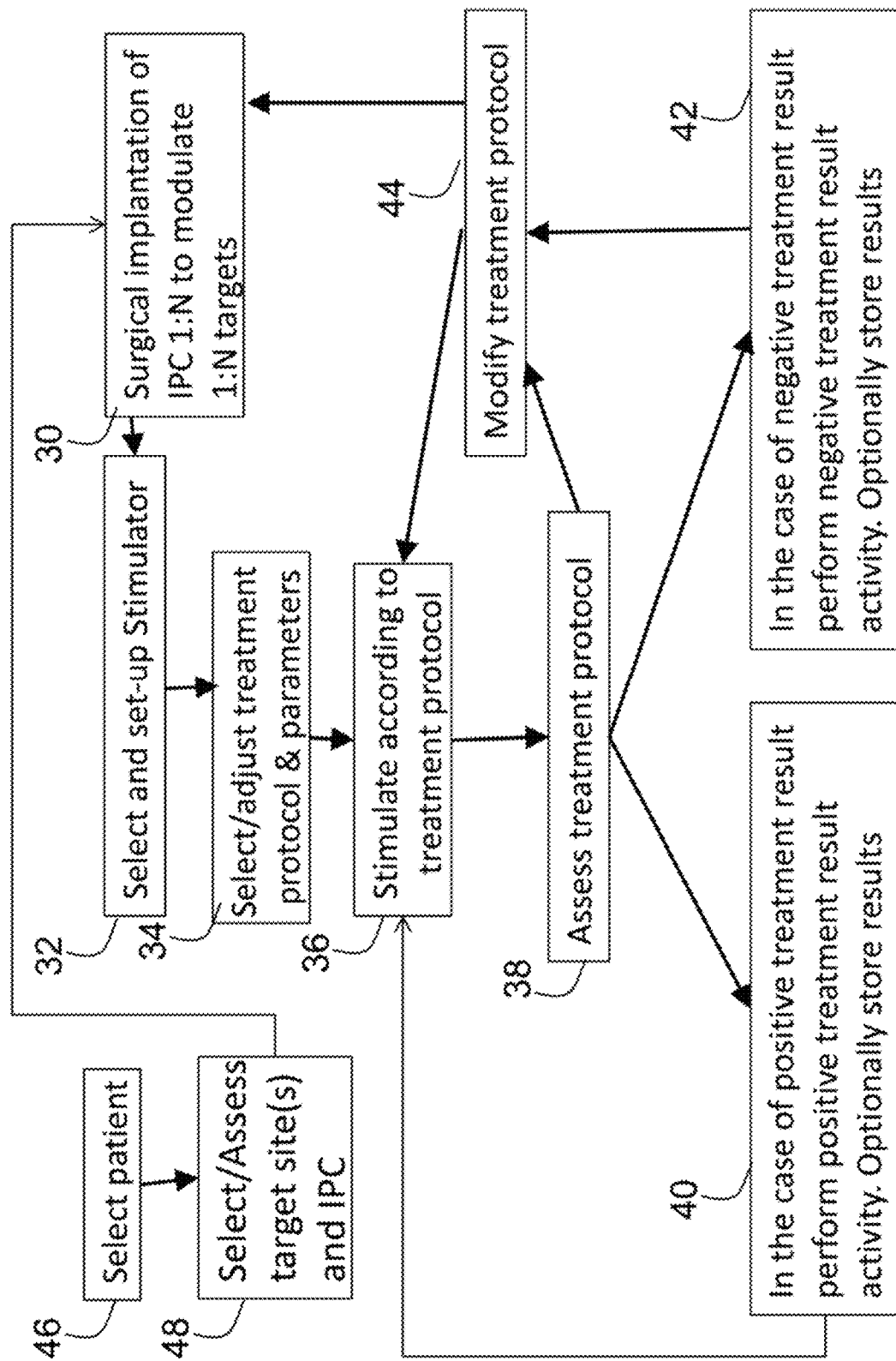
FIG. 17 is a logic flow block diagram showing a method for providing treatment to a patient.
Figure 22A:
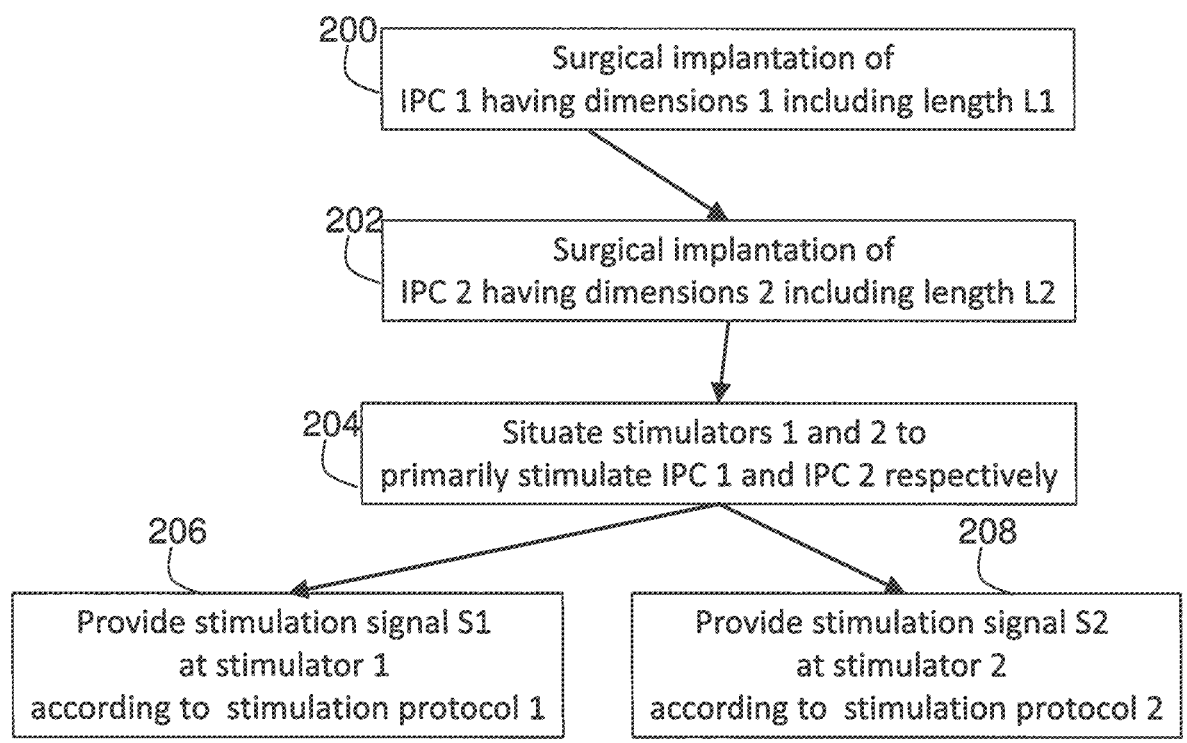
FIG. 22a is a logic block flow diagram for a method of using the eTNS system to stimulate using more than one IPC.
Figure 22B:
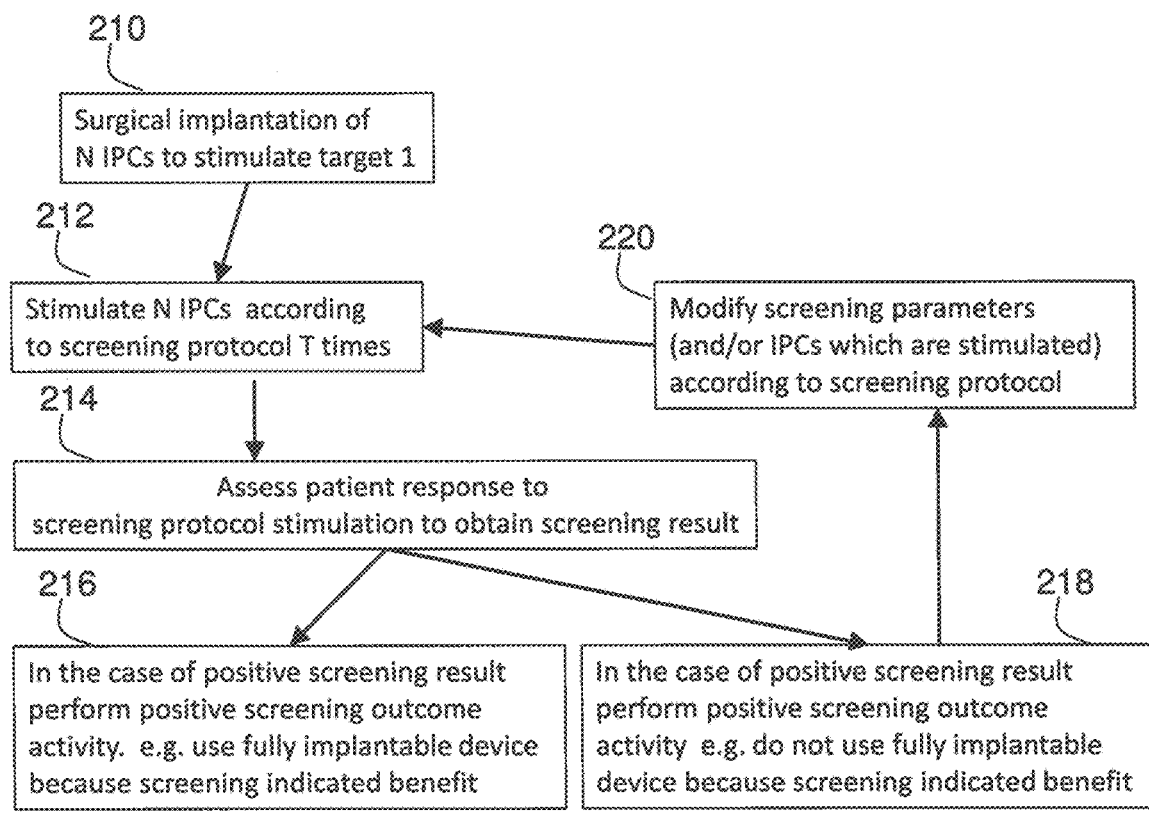
FIG. 22b is a logic block flow diagram for a method of using the eTNS system as a medical screening test.
Figure 22C:
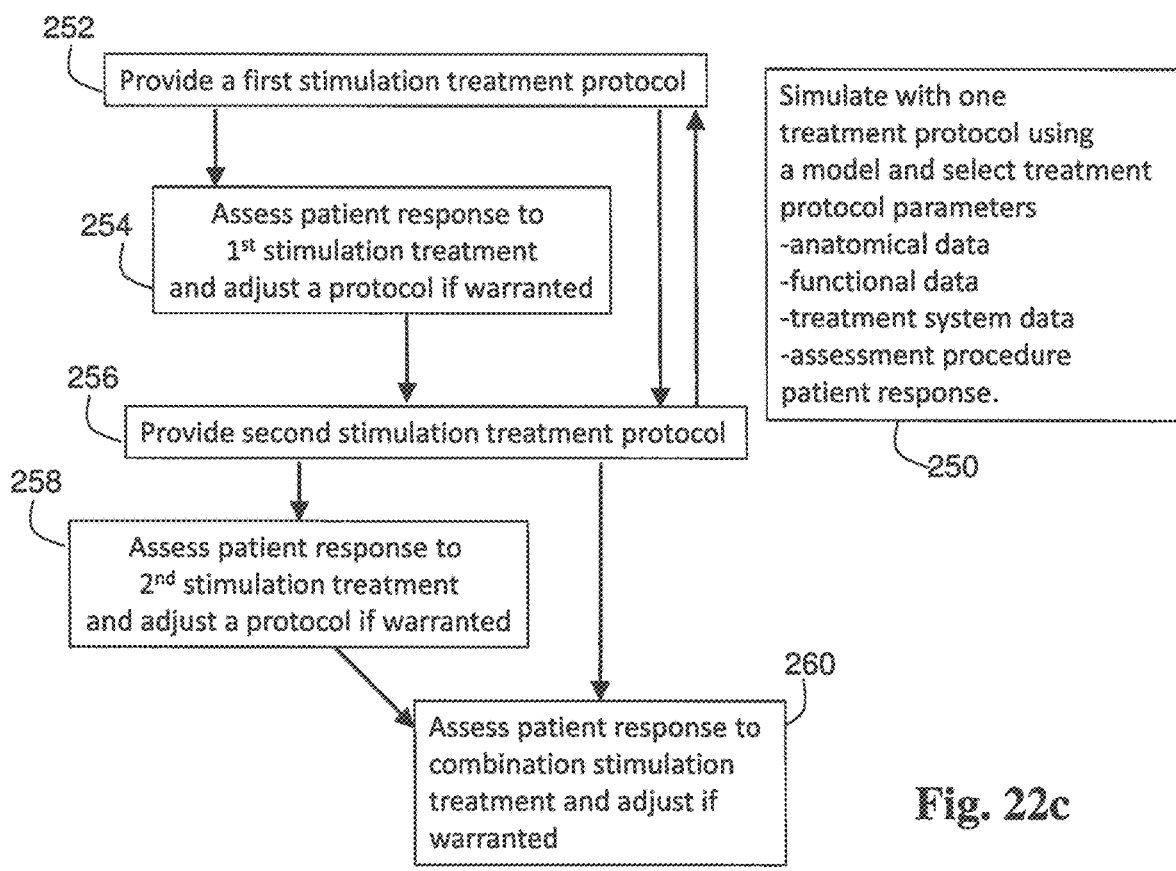
FIG. 22c is a logic flow block diagram for a method of providing a first stimulation treatment and second stimulation treatment for providing therapy.

Further advantages may be obtained if the IPC physical characteristics are configured for improved performance, such as may occur, in various embodiments, as part of step 48 of FIG. 17, or step 250 of FIG. 22c. For example, as will be shown, the IPC can provide larger improvements in performance when it is of an appropriate size, shape, material, and electrical property (e.g., higher conductivity than surrounding tissue). When configured according to certain considerations (e.g., size and location of at least one stimulator), the presence of the IPC 10 can reduce the net activation threshold of the targeted neural tissue. The "modification" of a stimulation field, according to the current invention, may include functionally modulating (e.g., redirecting, focusing, relaying, shaping, and/or otherwise having an effect on) the stimulation field so that the energy that reaches the targeted tissue enhances the effects of the applied stimulus to a greater degree than what may be achieved in the absence of the IPC.

One embodiment of the invention comprises implanting an IPC as shown in block 30 of FIG. 17 (e.g., metal nerve cuff surgically placed around a specific nerve branch) that will be used in conjunction with various transcutaneous, percutaneous, implanted, or other electrical stimulation devices, such as in step 36. These may include conventional transcutaneous electrical nerve stimulation (TENS) devices, implanted multi-contact lead electrodes (e.g., Medtronic Interstim device), intravascular nerve stimulation systems, and deep brain stimulation systems. Various physical parameters of the IPC (e.g., shape, length, width, thickness, density, curvature, material(s), resistivity/conductivity, relative permittivity) may also be used to shape, enhance and/or otherwise modify fields, and the parameter may be set or adjusted in block 34 in relation to at least one stimulator (i.e. "stimulator-IPC pairing"). In embodiments, the fields may be produced by electrical stimulators or magnetic stimulators, such as those used in transcranial magnetic stimulation (TMS). When used with magnetic stimulation devices, the IPC may be shaped, positioned, and oriented, relative to the 1 or more coils that generate one or more stimulation fields. When the IPC is used with TMS stimulators, the method and system may be referred to as enhanced TMS (eTMS). When realized as part of an eTMS embodiment, the IPC may be constructed using material with lower electrical conductivity than that used for eTENS. In an embodiment, the electrical source 18 of FIG. 1c may be replaced by a magnetic source which utilizes magnetic coils as stimulators 22a, 22b, (and which may be separated from the IPC by distances represented by parameters termed D2+D3). When the setup of FIG. 1c is realized as a model, with the electrical source 18 replaced by at least one magnetic source, additional model parameters can be related to the strength, orientation, distance (e.g., D2/D3), 3-dimensional location, and shape of one or more magnetic coils. Use of a magnetic stimulator with at least one coil 152 is shown in relation to providing vagal stimulation of a patient, by stimulating Implant #3 142c, in FIG. 21 (which can be realized by a device 400' such as that show in FIG. 24c).

Targets. Targets for enhanced excitation may include any anatomical component of the human nervous system, the activation of which may be used to modulate neural circuits or reflexes to achieve a desired clinical or therapeutic effect. These may include one or multiple nerves of the peripheral nervous system or a sympathetic nerve chain and/or all of the associated structures and nerves in communication with the sympathetic nerve chain. Certain targets may be very advantageously targeted by the current invention, such as targets that move or rotate or targets which are small. For example, it may be easier to stimulate an IPC which has been implanted in a portion of the eyeball which is coupled to a stimulator that sits outside of the eyeball, than to attempt to chronically implant an electrode that is capable of transmitting power along a path that requires the electrode to remain fixed and unbroken over a period of time. Another example is a target which may be within the vestibular system, or a facial or cranial nerve that is prone to movement which would make the use of a relatively larger, fixed electrode difficult. Another target may be in the foot, or near an ankle, where using a small IPC with an external stimulator will not be prone to the same damage or risk of electrode migration of an electrode which is tethered to a stimulator and which experiences shearing and pulling forces.

Conditions. The medical conditions that can be treated by methods of the present system and method include a host of conditions such as, but not limited to, skeletal, immunological, vascular/hematological, muscular/connective, neurological, visual, auditory/vestibular, dermatological, endocrinological, olfactory, cardiovascular, reproductive, sexual, urinary, psychological, gastrointestinal, respiratory/pulmonary, inflammatory, infectious (bacterial, viral, fungal, parasitic), traumatic, iatrogenic, drug induced and neoplastic medical and surgical conditions. Other conditions for which the technology may be applied are disclosed throughout this specification.

Treatment. As used herein, the term "treating" a medical condition encompasses therapeutically regulating, preventing, improving, alleviating the symptoms of, reducing the effects of, and/or diagnosing a medical condition. As used herein, the term "medical condition" encompasses any condition, disease, disorder, function, abnormality, or deficit influenced by the nervous system. Further, the methods of the present invention can be used to treat more than one medical condition concurrently. Non-limiting examples of medical conditions that can be treated according to the present invention include genetic, skeletal, renal, dental, immunological, vascular or hematological, muscular or connective tissue, neurological, ocular, visual (treated with or without concurrent visual stimulation), auditory or vestibular, tinnitus (treated with or without concurrent auditory stimulation), dermatological, endocrinological, olfactory, cardiovascular, reproductive, urinary, fecal, psychological, gastrointestinal, respiratory/pulmonary, neoplastic, or inflammatory medical conditions. Further, the medical condition can be the result of any etiology including vascular, ischemic, thrombotic, embolic, infectious (including bacterial, viral, parasitic, fungal, abscessal), neoplastic, drug-induced, metabolic, immunological, collagenic, traumatic, surgical/iatrogenic, idiopathic, endocrinological, allergic, degenerative, congenital, or abnormal malformational causes.

Further, treatment may include stimulation. Stimulation may include any type of modulation of physiological or biological related activity. Thus stimulation and modulation may be used interchangeably when the intention is to describe the influence of a generated field upon human tissue. Other conditions for which the technology may be applied for "treatment" are disclosed throughout this specification.

Implant Component. The implanted component that is often referred to as an implantable passive component "IPC" may be as simple as a passive conductive element. The IPC may also have securing structure such as flaps that can be mechanically folded over to situate and secure the IPC in place. The IPC may have a least one suture hole for securing the IPC in place. The IPCs may be of many shapes and sizes and may have physical dimensions that are configured based upon the tissue target where it will be used, the distance of the target from the stimulator, and the size of a stimulator, as well as other factors. The IPC may have conductive and non-conductive surfaces and portions, as well as more than one conductive portion which are not electrically continuous with a different conductive section. When an IPC has circuitry that is driven by electrical or magnetic fields or otherwise then the IPC becomes an implantable active component "IAC". The IPC may have portions that are configured so that permanent implantable pulse generators can be attached to the IPC in the case where the IPC, such as may occur if cutaneous stimulation is found to be inefficient, or becomes inefficient over time.

Stimulator-IPC pairs. At least one stimulator and at least one IPC can be selected or adjusted so that these work in the intended manner to provide stimulation to a tissue target. For example, a stimulator-IPC pair may include a stimulator that has a physical dimension set in relation to the IPC to that the two are "matched". Further, a stimulator-IPC pair may be configured so that the stimulator and IPC have at least one edge that is aligned, which has been shown, in some instances, to provide for increased enhancement of effects on the target in the stimulation field.

Electrical fields and IPC-stimulator orientations. Various types of field inducing signals may include electrical, magnetic or both. In some embodiments, a modulation signal may include a moderate amplitude and moderate duration, while in other embodiments, a modulation signal may include a higher amplitude and a shorter duration. Various amplitudes and/or durations of field-inducing signals which are provided by stimulators such as 88, 90 may result in functional (i.e., super-threshold) modulation signals. Whether a field-inducing signal rises to the level of a modulation signal can depend on many factors (e.g., distance from a particular nerve to be stimulated; whether the nerve is branched; orientation of the induced electric field with respect to the nerve; type of tissue present between the electrode stimulators and the nerve; size of the IPC; suitability of pairing between the stimulator and IPC, etc.). Whether a field inducing signal constitutes a modulation signal (resulting in an electric field that may cause nerve modulation) or a sub-modulation signal (resulting in an electric field not intended to cause nerve modulation) may be affected by the proper alignment of at least one edge of the IPC and the stimulator.

Figure 2A:
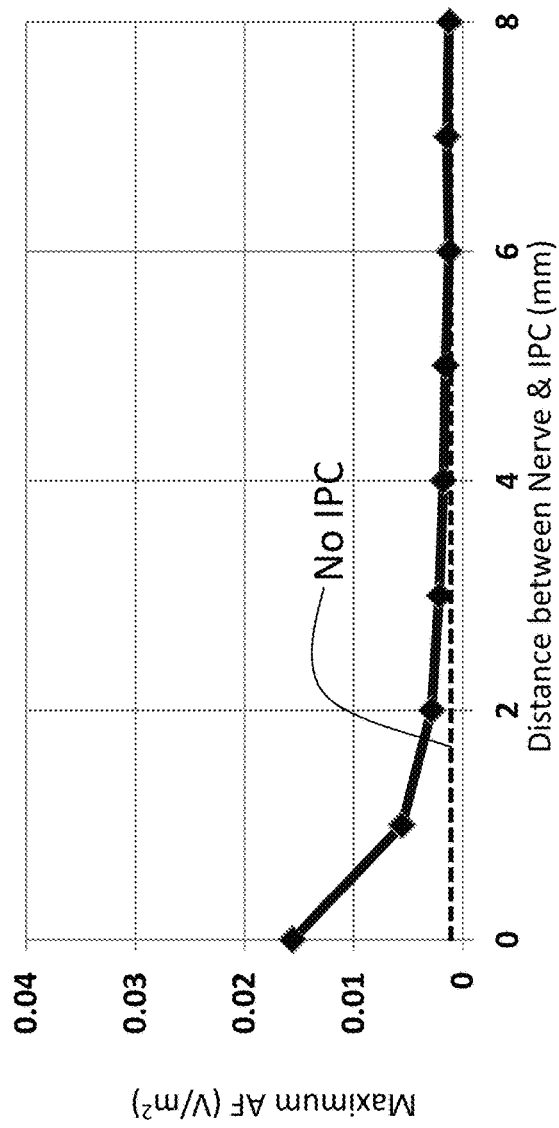
FIG. 2a is a graph showing results from a computer simulation that depicts the relationship between the activating function (AF: measure of neural excitability) and the distance between the IPC and the target nerve, where the distance between the surface electrode and the nerve is kept constant (a higher AF indicates a lower nerve activation threshold).

FIG. 2*a* shows a graph of the results of a modeled AF of a single axon located within the posterior tibial nerve (PTN) in response to a simulated current pulse (−1 mA) applied by a surface electrode stimulator. A computational finite element model was used to test the idea of enhancing the excitability of the PTN. The model consisted of a 3-dimensionally reconstructed human lower limb with a surface electrode placed over the PTN. The anode was the proximal cut surface of the lower leg (farthest from the surface electrode). As indicated in FIG. 1*a*, the IPC 10 is simulated as a highly conductive material placed in close proximity to the nerve and was modeled as a rod with diameter=0.2 mm and length=5 mm. The graph shows the simulated effects of varying the distance between the IPC 10 and the target nerve 12 on the calculated AF. In all simulations, the maximum AF value was used to determine and compare the excitability of the targeted nerve. The AF was calculated for a series of simulations, where the distance between the implant and the PTN was decreased from 8 mm (outside the epineurium) to 0 mm (direct contact with nerve bundle, perineurium). The results of FIG. 2*a* indicate that the implant (IPC)—for the given length, diameter, shape, and conductivity—begins to enhance neural excitability at a distance of approximately 3 mm from the nerve. This enhancement continues to increase to almost 8-fold when the implant is embedded within the connective tissue layer surrounding the nerve itself (the "epineurium"). The graph suggests that using this setup, a steep benefit is gained as the IPC-to-nerve distance is reduced below 2 mm. Modifications to the model (e.g., size and location of the stimulator, IPC or nerve) may change the shape of the graph.

Figure 2B:
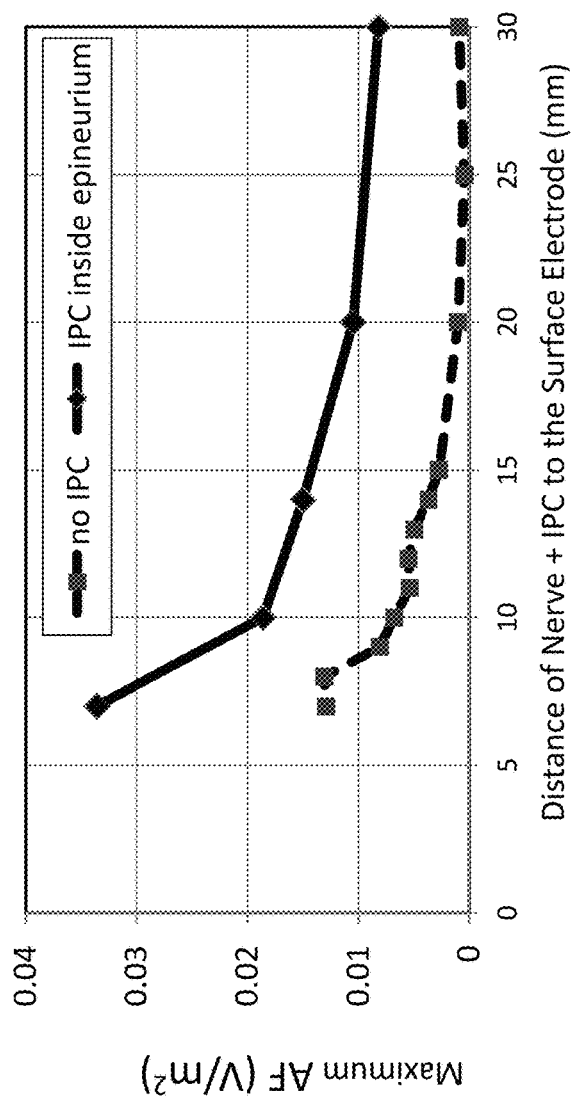
FIG. 2b is a graph showing results from a computer simulation that depicts the effects of the IPC on the AF, where the distance between the surface electrode and the target nerve was increased (depth from skin surface=7 mm to 30 mm).

FIG. 2*b* shows the simulated results reflecting changes in the AF as the distance between the IPC and nerve combination ("Implant+Nerve") and at least one of the stimulating electrodes is increased. The effects of the implant on neural excitability were quantified by comparing the maximum AF between the control case (labeled as "no IPC" in the figure) to the case where an IPC was placed in close proximity to the nerve (i.e., inside the epineurium). The results of this computational model show that the implant caused a 184% increase in AF for a nerve located 7 mm from the skin surface (i.e., stimulating electrode). Compared to the nerve without an IPC (labeled as 'no IPC', dashed line), the AF is consistently greater with the IPC placed close to the nerve (labeled as "IPC inside epineurium", solid line). Further, at a stimulator-to-IPC distance of 30 mm the AF achieved by the IPC is similar to the AF achieved at a stimulator-to-nerve distance of under 10 mm, when no IPC is used.

Repeated computer simulations at stimulator-to-nerve distances of up to 3 cm (as per FIG. 2*b*) showed that the AF drops precipitously over the initial 15 mm and reaches an asymptotic value at about the 25 mm. This trend is the same for both cases (with and without the IPC), but clearly shows that the IPC enhances neural excitability at all nerve depths.

Figure 3A:
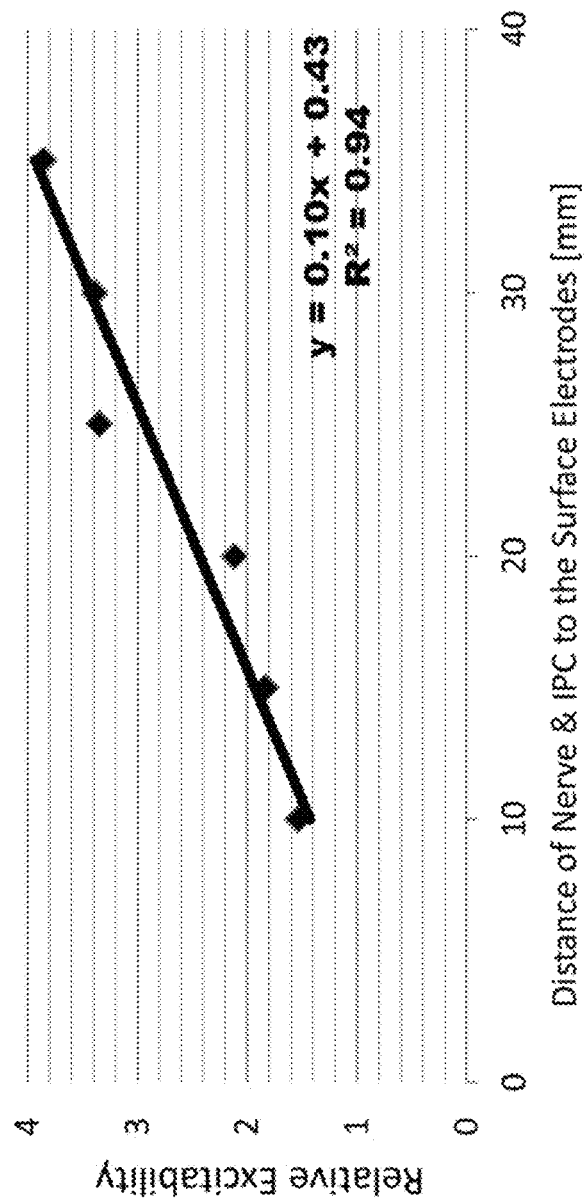
FIG. 3a is a graph showing modeled results of relative "neural excitability" as a function of nerve depth from the skin surface (the relative excitability was calculated as the ratio of the AF between the "IPC present" condition and an "IPC absent" condition).

FIG. 3*a* shows modeled results of the "relative excitability" of the target nerve, calculated as the ratio of the AF of an "IPC present (rod)" condition compared to an "IPC absent (no rod)" condition (see FIG. 2*b*). The positive slope indicates that the enhanced neural excitability effect due to the IPC is relatively greater for nerves located further away from the surface electrode stimulator. As per FIG. 3*a*, the simulation results suggest that, by using an IPC, the stimulation amplitude required for transcutaneous nerve activation can be significantly reduced. For example, FIG. 3*a* suggests that the stimulation amplitude at the surface may be reduced to from approximately one-half to one-quarter of the original stimulation intensity, since the relative excitability (RE) moves from about 1.8× to about 4×.

Figure 3B:
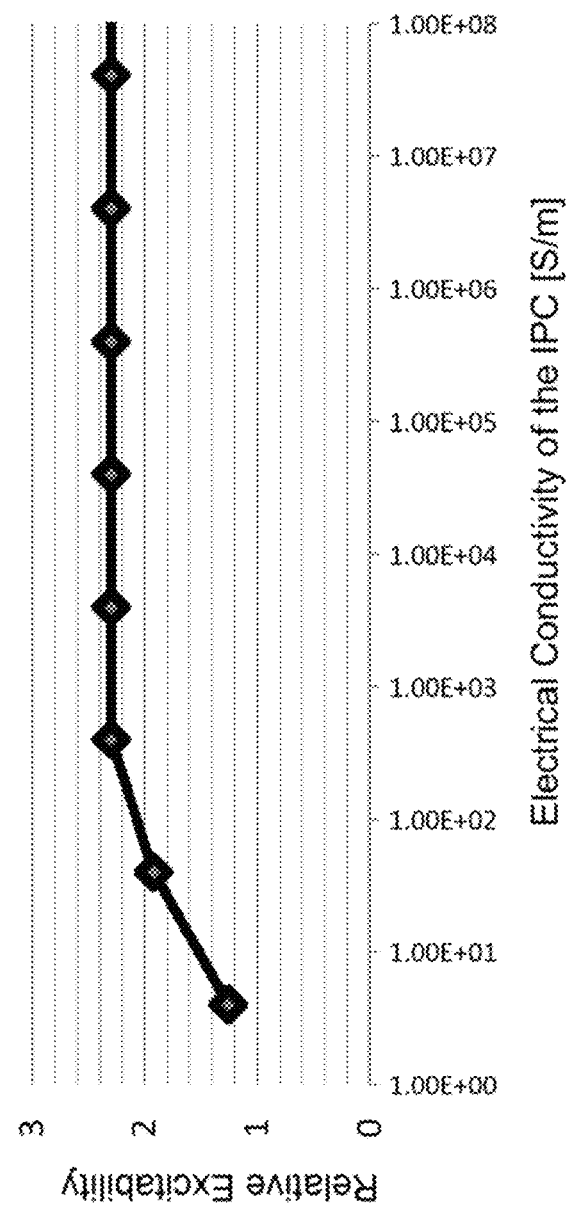
FIG. 3b is a graph showing modeled results of the effects of the electrical conductivity of the IPC on the relative neural excitability (AF).

FIG. 3*b* shows the effects of electrical conductivity of the IPC (rod-type implant) on the RE (relative excitability) of the target nerve Enhancement of neural excitability (quantified as the relative excitability) is maximally achieved when the electrical conductivity of the IPC equals or exceeds 4E+2 S/m (or approximately 1.00E+3 on the graph). This lower boundary corresponds to an electrical conductivity that is approximately 5 orders of magnitude greater than that of the nerve (e.g., epineurium). These results suggest that most highly-conductive metals would serve as appropriate IPC materials for enhancing TENS, with platinum or gold serving as good candidates. Of course various conductive alloys, and semi-conducting material which are suitably doped, may be used to create at least portions of the IPC.

Figure 4A:
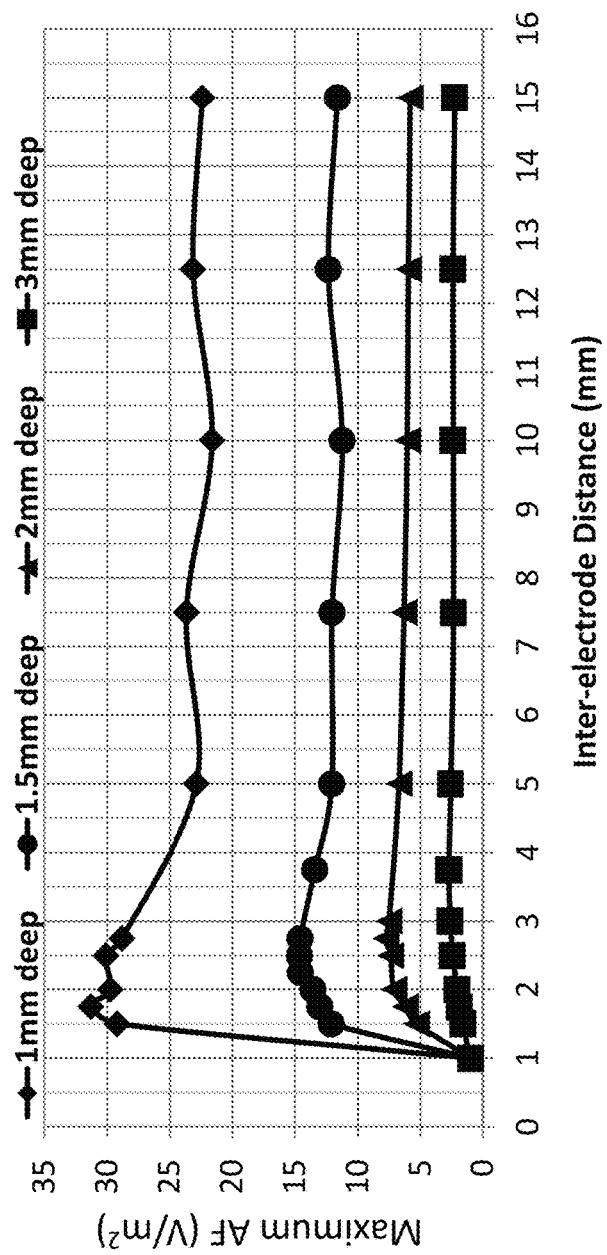
FIG. 4a is a graphical representation showing data from computer simulations (according to setup shown in FIG. 2) that calculated the AF generated by conventional TENS (no IPC) as a function of both the depth of the nerve (D2, depth distance to nerve from cutaneous stimulation electrode) and the distance between the anode and cathode surface electrodes (D1, inter-electrode distance is the x-axis).

FIG. 4*a* shows the effects of nerve depth (from skin surface) on the inter-electrode distance between two surface electrode stimulators (bipolar stimulation, see FIG. 1*c*). The effect was quantified by the maximum AF calculated from computer simulations of the rat PTN that simply included stimulators and did not also incorporate the subcutaneous placement of an IPC. These results are relevant to transcutaneous stimulation embodiments of the invention having bipolar surface electrodes. The finite element model, having a monopolar setup which is illustrated in FIG. 1a, and which was used to generate results presented in FIG. 2a, 2b and FIG. 3a, 3b, was modified to approximate transcutaneous electrical stimulation of the PTN in a rat. This modification simply involved scaling all components of the model to that of rodents: nerve radius (0.38 mm), nerve depth (1.5 mm), skin thickness (0.46 mm), pair of surface electrodes (2 mm×1 mm) comprising the anodic and cathodic electrodes. The results of this computer model indicate that optimal nerve activation (maximum AF) is achieved when the inter-electrode (stimulator) distance approximates the depth of the nerve from the skin surface (1 to 3 mm). It is noted that the maximum AF at an inter-stimulator distance of 1 mm indicates very low neural excitation for all nerve depths. This suggests that the electrical current is effectively shorted between the cathodic and anodic electrodes. When an IPC is also used, the shape of the graph may be affected by the physical dimensions of the IPC and stimulators, both in absolute and/or relative terms.

These results indicate that deeper nerves are more easily activated by bipolar electrode pairs when greater separation is used. In one embodiment of the system 6, shown in FIG. 1c, the inter-stimulator distance D1 should be varied proportionately to the distance between the stimulator and the nerve D2. The effects relating to spacing of the surface electrodes, in relation to depth of stimulated tissue target, may be applicable whether an IPC is used or not. In general, if the electrodes are placed closer together the area of highest current density will be relatively superficial, while further spaced electrodes will cause the current density to be higher in deeper tissue. Electrode stimulator size will also change the current density, with larger electrodes decreasing current density relative to smaller electrodes. Accordingly, placing a smaller electrode closer to the nerve or IPC with a larger electrode (dispersive electrode) remote from (further away) the tissue target should cause the current density to be higher near the smaller electrode (near the tissue target). Cutaneously applied electrode size and position characteristics will therefore alter the characteristics of the current density and path. When an IPC is used, this relationship must also be considered in relation to the specifications of the IPC. If the IPC and stimulators are "paired" with respect to certain characteristics, in order to increase the effectiveness of stimulation, then these pairing should be considered with respect to factors such as depth of the IPC/nerve, and may be part of step 250. Stimulation of a deeper nerve may require a larger spacing of the surface stimulators, which may, in turn, require an increased length of IPC. These, as well as other considerations may be used in the adjustments to the current invention stimulation systems and methods of providing therapy to a patient.

Figure 4B:
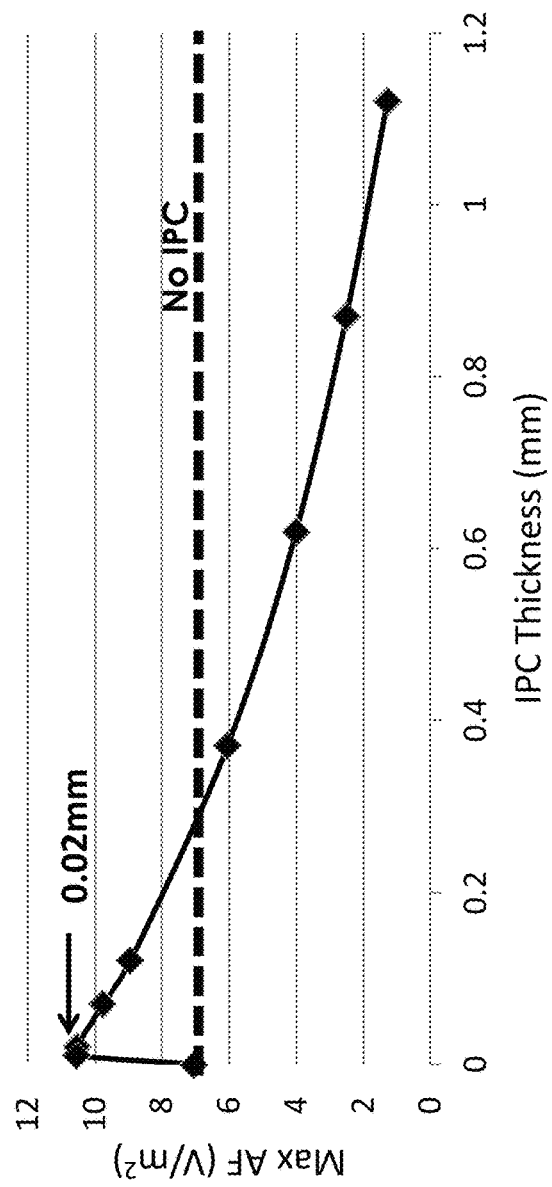
FIG. 4b is a graphical representation showing data from computer simulations that depict the effects of IPC thickness (i.e., thickness of cylindrical wall of nerve cuff) on enhancing neural excitability ("Max AF") and shows that, compared to the case of 'no IPC', an IPC thickness of less than 0.3 mm increases AF, while a thickness above 0.3 mm was found to reduce neural excitability.

FIG. 4b shows a graph of computationally generated simulation results exploring the effect of IPC thickness. These results are relevant to, and can be used to guide, the adjustment the IPC shape characteristics. Instead of the IPC modeled as a solid cylindrical rod placed within the epineurium (FIG. 1a), the IPC was modeled as a simple cylindrical cuff wrapped around the nerve (FIG. 1b). This practical and simple design is currently used for many implantable nerve cuff electrodes. With the cuff length set at 5 mm, the thickness of the cylinder was varied from zero (reflecting no IPC) up to 1.2 mm. The results of this study suggest that neural excitability is maximally enhanced by thinner IPCs (e.g., 20 μm thickness), at least in the case of implants with a length of 5 mm and a relatively shallow nerve depth of 2 mm. Various different manners of modifying the IPC physical characteristics may also serve to increase excitability, aside from adjusting the shape characteristic to create a thin IPC. For example, when the IPC physical characteristic are selected so that the IPC created of a mesh, or using material with different electrical conductivity, may also provide improved excitability. In one embodiment, using a material such as mesh that decreases the mass of the implant, increases flexibility and adaptability of the IPC, and increases patient comfort, or has other advantages may improve the performance of the system and decrease the likelihood of adverse events. Further, it should be noted that an IPC thickness of less than 0.3 mm increased AF, while a thickness above 0.3 mm was found to reduce neural excitability. When using a bipolar stimulation configuration, a therapy system may rely upon different IPC thickness to "selectively" activate targeted nerve(s). Since increasing thicknesses of the IPC above a certain dimension (e.g., IPC thickness=0.3 mm) was found to increase rather than decrease the activation threshold, an IPC of increased thickness above that threshold thickness can be used to suppress activation of adjacent non-target nerves at this particular nerve depth. A thinner IPC, configured to increase the excitability of a nerve, can be used on the target nerve.

Figure 4C:
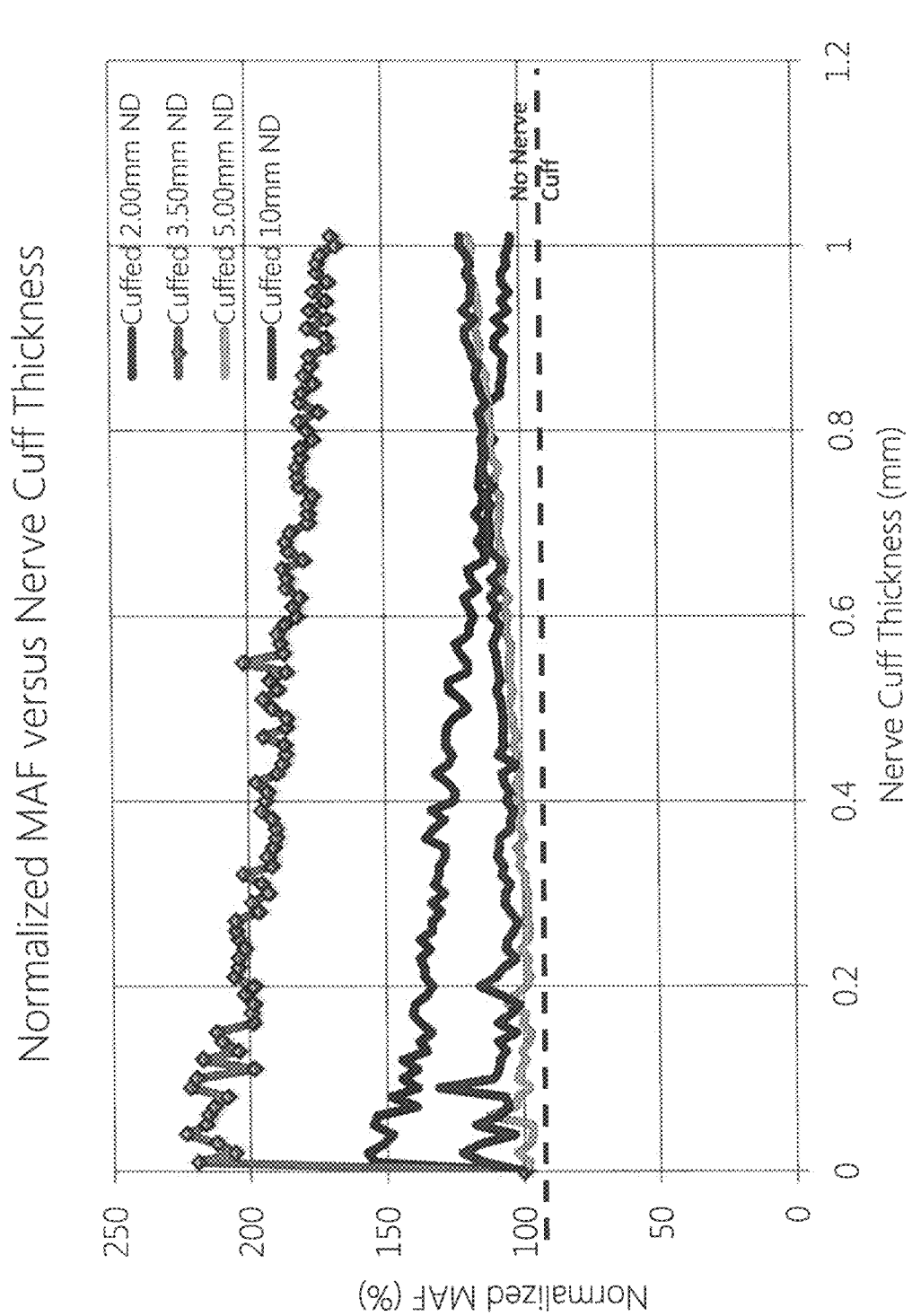
FIG. 4c is a graphical representation showing data from computer simulations showing the normalized Max AF as a function of both the thickness of the nerve cuff (IPC) and the depth distance of the nerve from skin surface (ND).

FIG. 4c is a graphical representation showing data from computer simulations involving a monopolar stimulator used to activate a peripheral nerve placed at varying depths. In this embodiment, the normalized MAF increased as the thickness of the IPC (cuff-type implant) was decreased, at nerve depths (ND) of 2 mm and 3.5 mm. The enhanced effects of reducing IPC thickness at these relatively shallow nerve depths corroborate our simulations that used bipolar stimulators (FIG. 4b). However, at deeper nerve depths (5 mm and 10 mm) the normalized MAF increased as the IPC thickness was increased. This enhancement in neural excitability indicates that greater overall electrical conductivity of the IPC may play an important role for nerves located relatively farther from the skin surface. As a result, this suggests that eTENS activation of nerves at relatively greater nerve depths may be further enhanced such as by using different IPC material (e.g., higher electrical conductivity), and larger dimensions (e.g., length, see FIG. 8).

FIG. 5a shows a graph of simulated results of the optimum combinations of inter-electrode distance and IPC length for achieving effective peripheral nerve activation (i.e., lowest activation threshold). In a model of rat PTN stimulation (e.g., as per the set-up of FIG. 1b) the peak of each trace corresponds to an IPC length that is very similar in physical dimensions to the inter-electrode distance. The data suggest that enhancement of neural excitation is improved when the inter-electrode distance approximates, or is a little less than, the length of the IPC, for the range of IPC lengths shown. Changes in the AF were studied in response to varying the length of the implant, from 0 mm (no implant) up to 15 mm. These simulations were repeated for different inter-electrode distances: 2.75 mm, 5 mm, and 7.5 mm. For each given inter-electrode distance and bipolar configuration, the maximum AF was achieved when the implant length approximated this distance (e.g., 8 mm implant length for an inter-electrode distance of 7.5 mm). Accordingly, in a system for providing eTENS therapy 6 the IPC length can be set in proportion to the distance between at least 2 stimulators, such as being equal to, or slightly less than, the distance between the two electrodes.

In FIG. 5a, the zero mm data points are equivalent to not using any IPC ("no IPC"). Accordingly, any system and method which utilizes an IPC that increase the AF above the no-IPC condition can provide enhanced nerve excitability. Further, any AF which is below the no-IPC condition, for example, IPC lengths of about 12 to 15 when the inter-electrode distance is any of those tested in the figure, will serve to decrease the excitability of that nerve. Accordingly, providing IPCs that cause decrements in excitability to non-target nerves may provide a strategy for further increasing the selective activation of a targeted nerve. Further, even when not discussed explicitly, in all other figures of this application, when the AF drops below the no-IPC condition, the results could be understood to be relevant to providing greater selectivity of target nerve stimulation.

Additional computer simulations were also conducted using a single monopolar surface electrode that was aligned to the center of the IPC 10. The width (W) remained the same, but the length was varied. The anodic (return) electrode was modeled as being placed far away from the active cathode. The results of this study showed that maximum AF (i.e., lowest stimulation threshold) was achieved when the length (L) of the single electrode was larger than the IPC. In other words, when the mono-polar electrode fits exactly in between the pair of electrodes in FIG. 1c the optimum activation was not found. While the results of FIG. 5a, suggest that optimum nerve stimulation is achieved when the opposing ends at each edge of the IPC align (approximately) with those of the surface electrodes, this may be true for bipolar but not monopolar stimulation. It is likely that in one embodiment of a clinical system, the edges of the IPC and at least one electrode should be approximately aligned, while alignment of two parallel edges may only improve bipolar stimulation. Initial data has suggested that in the case of monopolar stimulation, increased activation is obtained when the monopolar electrode is longer than the IPC (data not shown). Accordingly, in one embodiment of the system which uses a monopolar electrode, at least the length or width of the IPC should be made to be larger than then IPC, and further only one edge of the IPC should be aligned with an edge of the stimulator electrode.

FIG. 5b shows a graph of computer simulations using the original human PTN model (inter-electrode distance range: 2 cm to 8 cm) that confirm the results of the rat PTN model translate to larger physical dimensions.

Figures 6A, 6B:
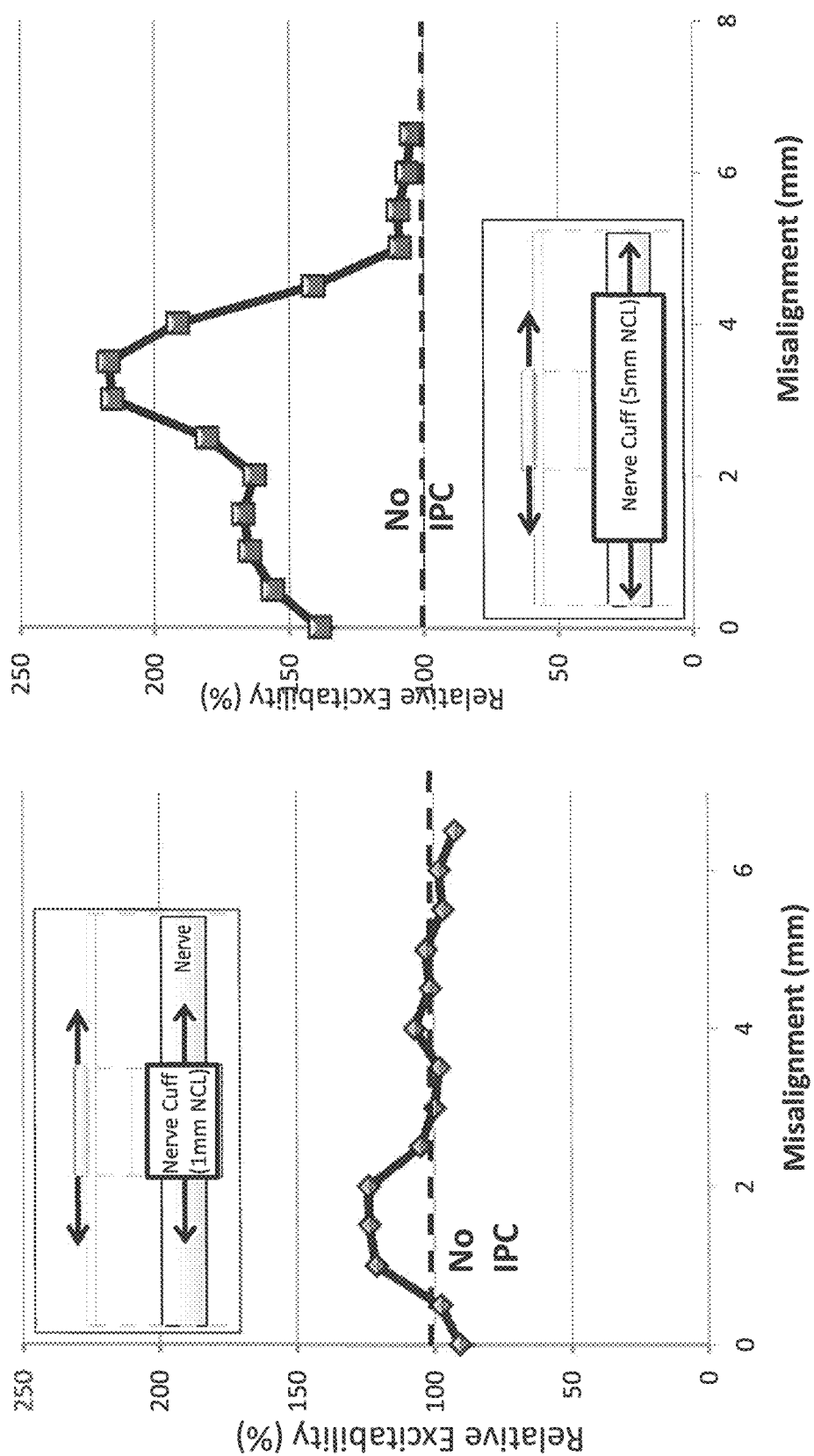
FIG. 6a is a graph of data from a computer model of eTENS (scaled to dimensions of a rat) involving monopolar surface stimulation in which the surface electrode (area=1 mm×1 mm) and IPC (nerve cuff length, NCL=1 mm) are of similar dimensions, and initially aligned as depicted in the inset diagram (misalignment=0 mm) and in which the relative excitability (% AF normalized to TENS with no IPC) is calculated as the IPC is shifted along the nerve (surface electrode is stationary) such that the misalignment increases from 0 mm to 6.5 mm.
FIG. 6b is a graph of data from a computer model of eTENS (scaled to dimensions of a rat) involving monopolar surface stimulation, in which the dimensions of the surface electrode (area=1 mm×1 mm) are smaller than the IPC (nerve cuff length, NCL=5 mm), and in which the IPC is shifted along the nerve (surface electrode is stationary), such that the misalignment increases from 0 mm to 6.5 mm.

FIG. 6a shows a data from a computer model that simulated eTENS using a monopolar surface electrode. When both edges of the electrode (length of 1 mm along the nerve) and the IPC (nerve cuff length of 1 mm) are aligned (misalignment=0 mm), the AF is actually below that of TENS without any IPC. However, as the IPC is moved along the nerve, the AF becomes approximately 1.25 times greater than that for conventional TENS. In this example (nerve depth=2 mm), the 'enhancing effect' of the IPC persists even with an inter-edge gap (distance between the right edge of electrode and the left edge of IPC) of up to 1 mm (i.e., misalignment=2 mm). Beyond this misalignment, the IPC has negligible effect on neural excitability. Accordingly, in one embodiment of the system which uses a monopolar electrode, the alignment of the IPC and stimulator should be adjusted, as per step 48 in FIG. 17, so that the inter-edge gap provides improved AF. The nerve depth in this example was only 2 mm and different results may be simulated for other nerve depths in order to obtain relative excitability functions for those depths which can then be implemented by the systems and methods of the current invention.

FIG. 6b shows data from a computer model that is similar to FIG. 6a, but with a longer IPC (nerve cuff length=5 mm). These results show that if the IPC is longer than the surface electrode and that the electrode overlaps with the nerve cuff (misalignment up to 2.5 mm), the AF of the target nerve is enhanced by 1.4 to 1.8 times that of conventional TENS. Maximum enhancement is achieved (increased AF by 2.2 times) when the inter-edge gap (between the electrode and IPC edges) is between 0.0 mm and 1.0 mm (which occurs when the misalignment is about 3 mm). At inter-edge gaps greater than 2.5 mm (misalignment above 5 mm), the IPC does not affect neural excitability.

Figure 7:
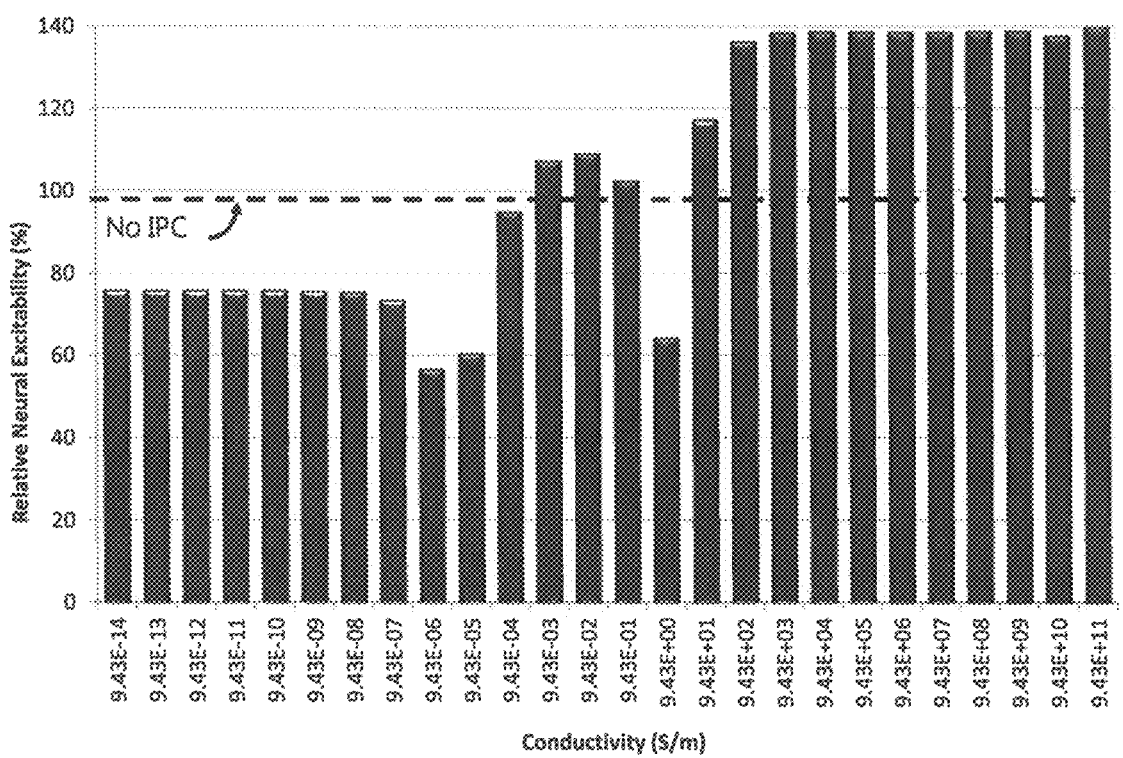
FIG. 7 is a graph of data relating to the effects of the electrical conductivity of the IPC (monopolar stimulation model in FIG. 6) on the relative % neural excitability, as the conductivity values were increased from 9.43e-14 to 9.43e+11.

FIG. 7 shows a graph of computationally generated results exploring the effects of the electrical conductivity of the IPC on the relative neural excitability using monopolar stimulation (nerve depth=2 mm, IPC thickness 0.02 mm). For conductivity values above 9.43E+2, there is observed enhanced neural excitation (as shown in FIG. 3b). However, at electrical conductivity values between 9.43E-4 and 9.43E-1 there is observed negligible effects of the IPC (no change in relative excitability); whereas at conductivity values below 9.43E-5 there is observed reduced excitation of the nerve on which the IPC is implanted. These findings suggest a novel system and method of increasing the selective activation of a targeted nerve in which a highly conductive IPC is implanted on the target nerve. Additionally, a poorly conductive IPC may be placed on or near one or more non-target nerves to deter unwanted activation.

Figure 8:
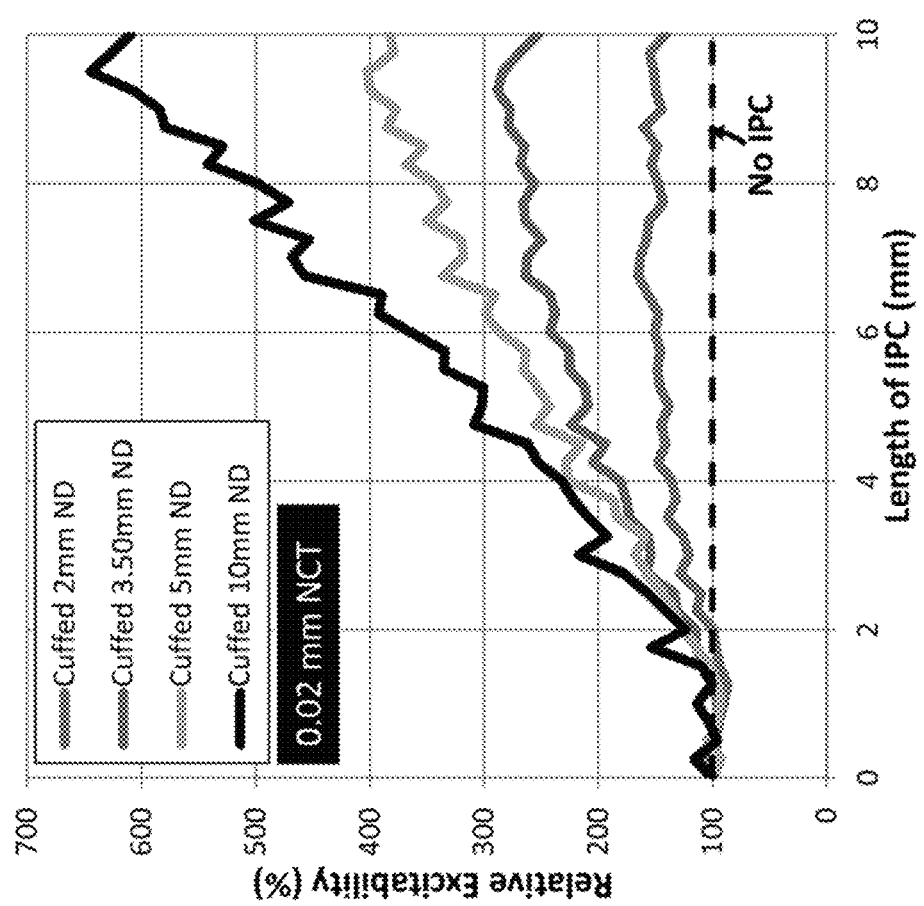
FIG. 8 is a graph of data from a computer model of eTENS (monopolar stimulation model in FIG. 6), where the effects of IPC length on relative excitability were simulated for an IPC with 0.02 mm nerve cuff thickness (NCT, refer to FIG. 4b), and where the length of the IPC ('cuffed around the nerve') was increased from 0 mm (no-IPC baseline condition) to 10 mm for 4 different cases of nerve depth (ND): 2 mm, 3.5 mm, 5 mm, and 10 mm from the skin surface.

FIG. 8 shows the relationship between the length of the IPC and the depth of the nerve (ND). In this computational model, the IPC was a nerve cuff with 0.02 mm thickness and the IPC+nerve was positioned at 4 different nerve depths: ND=2 mm, 3.5 mm, 5 mm, and 10 mm from the skin surface. For this example of monopolar stimulation, the data indicates that increasing the length of the IPC can markedly increase neural excitability. This 'enhancement effect' is more pronounced for nerves located further away from the skin surface. For shallow nerve depths (2 mm), the effects of increasing the IPC length are diminished beyond 4 mm, with the neural excitability increase showing a plateau at approximately 1.5× of conventional TENS (no IPC). In contrast, at deeper locations (10 mm ND), the AF continues to increase up to IPC lengths of 9.5 mm, where the neural excitability reaches a 6.5 multiple of conventional TENS. In an embodiment of the system and method of providing eTENS stimulation, the length of the IPC can be adjusted, as per step 48 in FIG. 17, in order to derive the desired increase in neural excitability. Additionally, for deeper nerves, longer IPCs should be selected to provide improved enhancement of neural excitability. Further for deeper nerve targets, increasing the thickness of the IPC may provide for increased excitability of the target nerve (FIG. 4b shows increased MaxAF at lower thickness, compared to higher thicknesses, because that nerve target was relatively superficial).

Evidence supporting the ability of the IPC to provide enhanced excitability was also obtained from in vivo studies (anesthetized rat). A monopolar surface (cathodic) stimulating electrode (5 mm×10 mm) was placed over the PTN of the left leg immediately rostral to the calcaneous (ankle bone). The return electrode (anode) was connected to a needle inserted through the abdominal fat pad, ipsilateral to the active cathode electrode. A pair of de-sheathed stainless steel wires were inserted into the foot, ipsilateral to the cathodic electrode and connected to a low-noise amplifier. This electrode was used to record the electromyogram (EMG) evoked by transcutaneous PTN stimulation. Results from one experiment are shown in FIG. 9a, which illustrates that the presence of the IPC 10 around the PTN (immediately rostral to the ankle) lowers the nerve stimulation threshold by 30% of that seen when no IPC was used.

Figure 9A:
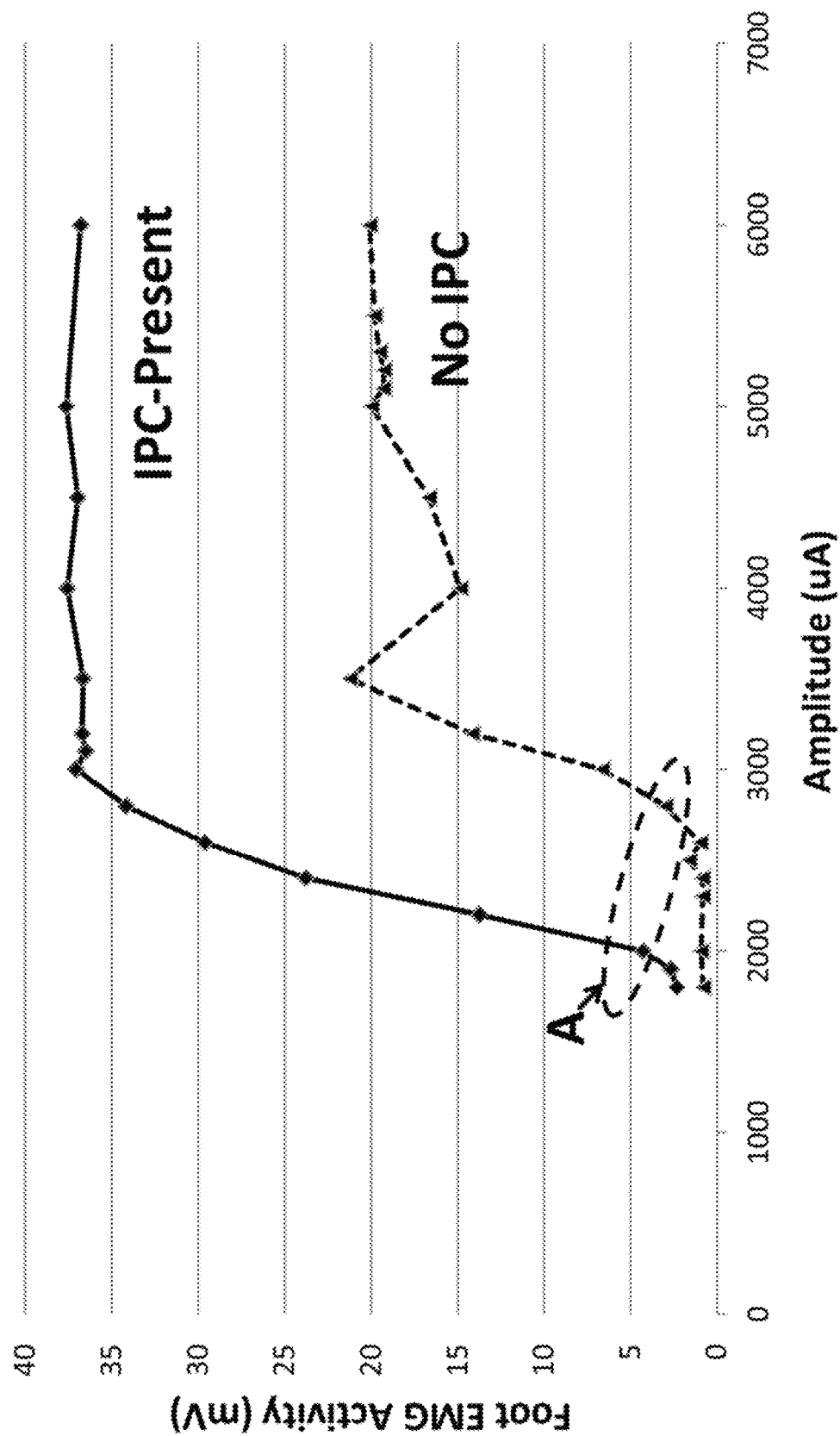
FIG. 9a is a graph of data from an experiment conducted in an anesthetized rat, where a surface electrode (5 mm×5 mm) was placed on the posterior-medial surface of the hind limb to stimulate the posterior tibial nerve and a pair of insulated stainless steel wires was inserted into the ipsilateral foot to measure muscle activation (EMG). The return "anodic" electrode was a needle inserted percutaneously through the abdominal fat pad, ipsilateral to the stimulated leg.
Figure 9C:
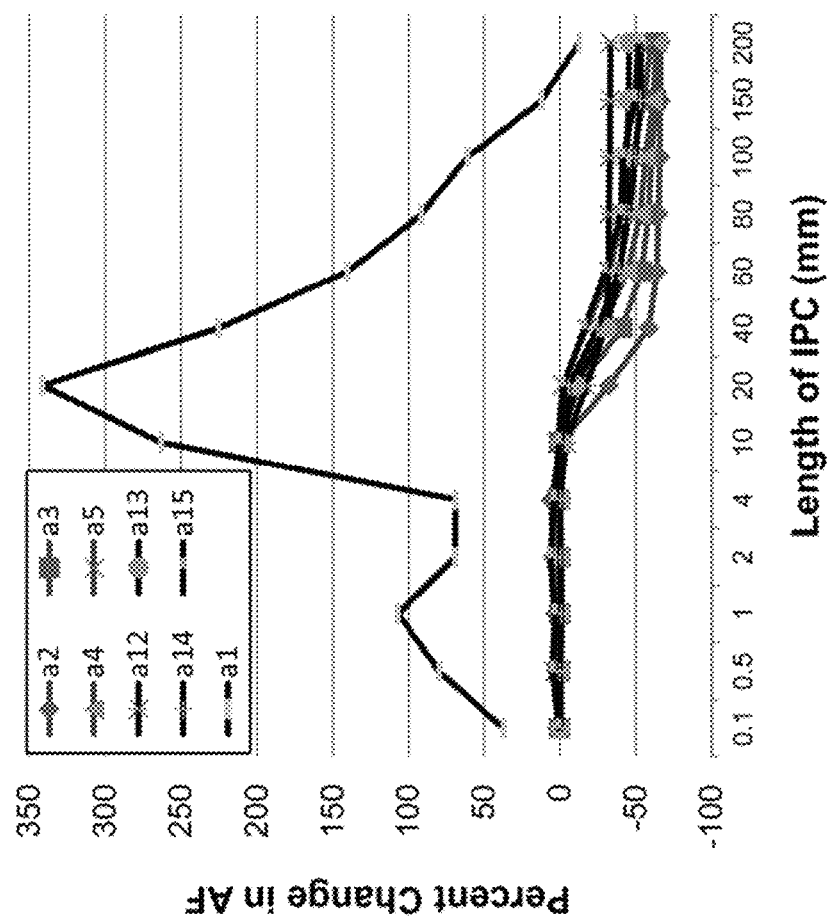
FIG. 9c is a graph of data derived from the computer simulation of FIG. 9b, where the target nerve (a1) shows increased AF which peaks when the IPC length is between 10 and 40 mm, while the non-target nerves show reduced AF, supporting both increased sensitivity and specificity, respectively, to the stimulation electrode.
Figure 9B:
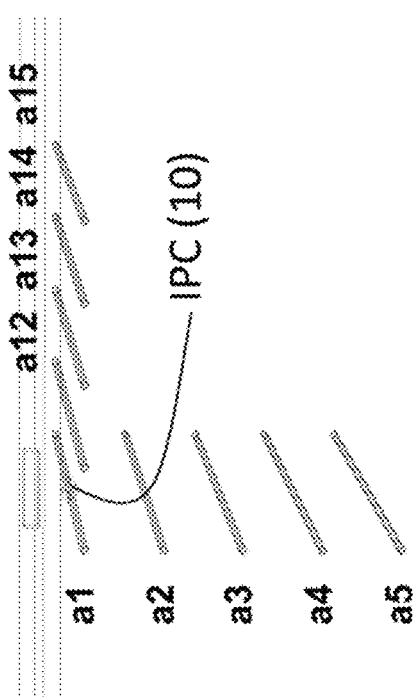
FIG. 9b shows the experimental set-up of a computer simulation, where a surface electrode (10 mm×10 mm) was positioned over an array of peripheral nerves (diameter=1 mm, length=100 mm) and the target nerve (a1) was positioned directly below the stimulating electrode at a depth of 3 mm from the skin surface. Additional nerves were positioned in both vertical (a2 to a5) and lateral (a12 to a15) fashion with respect to a1. The distance between each nerve was 10 mm.

FIGS. 9a, b, c show the effects of an IPC on the recruitment properties of transcutaneous nerve stimulation. These results were obtained from (FIG. 9a) rat experiments and (FIG. 9b, 9c) computer simulations. FIG. 9a characterizes the recruitment of foot EMG activity that was elicited by transcutaneous PTNS, with (solid line) and without an IPC (dashed line) placed around the nerve. The implant was implemented experimentally in anesthetized rats as an aluminum cuff. The data indicate that the IPC 10 of the current invention can effectively (1) lower the stimulation threshold (labeled "A" in the figure) for activating the PTN (2000 uA vs. 2800 uA) and (2) recruit more PTN fibers from transcutaneous stimulation (37 mV vs. 21 mV). FIG. 9b shows a diagram of the computer model, which was used to investigate the effects of the IPC (implanted on a1) on the neural excitability of non-target nerves (a1-a5 and a12-a15). FIG. 9c compares the computationally derived activating function (i.e., nerve excitability) of multiple nerves, where one (a1) has been instrumented with an IPC. As the length of IPC was increased from 0.1 mm to 4 mm, the excitability of the target nerve (a1) showed a 50% to 100% increase in the AF; while there was little change in the excitability of non-targeted nerves (a2 to a5, a12 to a15). Further, at IPC lengths of 10 mm and above, the excitation properties of the targeted (a1) and non-targeted nerves begin to diverge more dramatically. The percent change in AF for a1 reaches a peak at 20 mm (342% increase), while the remaining nerves exhibit a 40% to 60% decrease in excitability beyond this IPC length. This data support an embodiment of the system and method of providing eTENS stimulation, wherein the IPC is provided on a target nerve to increase the sensitivity of a target nerve to stimulation, and within certain ranges the IPC can also increase the specificity of the stimulation by decreasing the effect of the electrical field on non-target nerves.

While the experimental data (FIG. 9A) confirms enhanced neural excitation achieved by an IPC placed around the target nerve (i.e. increased activation function), the computer model (FIG. 9B) shows that the IPC can concomitantly reduce the excitability of surrounding (non-targeted) nerves. These results suggest that the presence of a single highly-conductive IPC can also minimize any stimulation-evoked side-effects caused by unwanted activation of adjacent nervous tissue. While the mechanism for enhanced selectivity, at a given stimulation level, is not yet fully understood, it may be that the IPC provides a lower resistance path for the electrical field and thereby decreases dispersion of the field around the area of the IPC. Accordingly, as will be disclosed later, in embodiments using 1 or more IPCs may be used to shape or guide an electrical path through tissue.

Treatment of Incontinence Related Disorders

A central use for the systems and methods of the present invention relate to treatment of chronic lower urinary tract dysfunction, such as overactive bladder and detrusor underactivity (related to urinary retention). For simplicity the term overactive bladder (OAB) may be used to refer to various types of voiding dysfunction, without intending to be limiting. The following section will provide example embodiments of the invention being used in the treatment of these disorders, with the understanding that the specific embodiments and principles can be generalized to the treatment of other disorders and the modulation of tissue to provide various benefits.

Figure 10B:
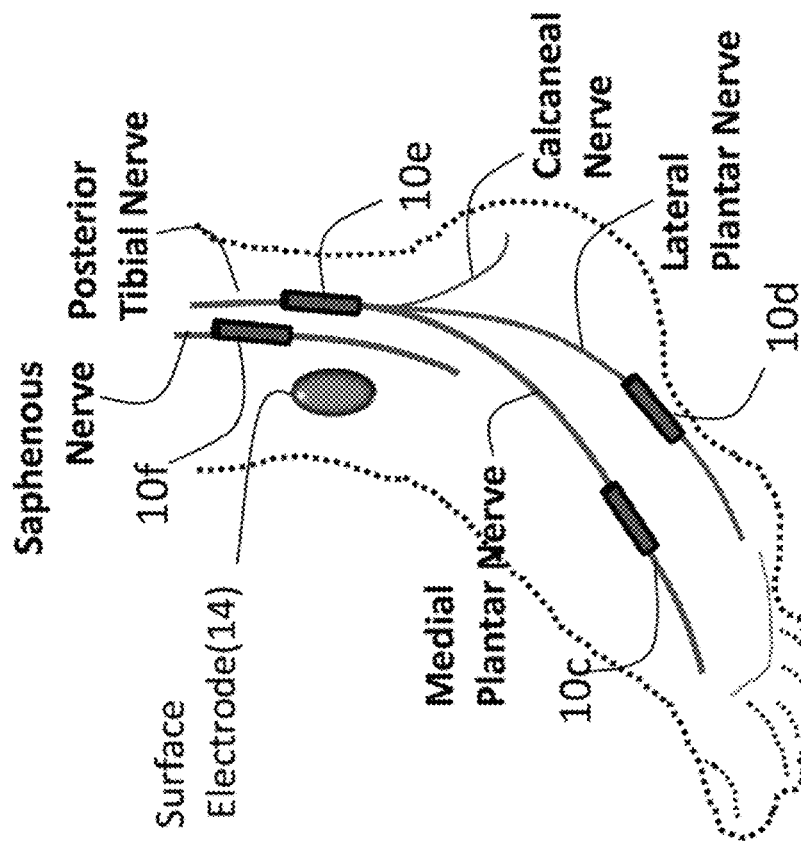
FIG. 10b schematically depicts the posterior tibial nerve (PTN) and saphenous nerve descending the posterior-medial aspect of the human leg. The PTN divides into the medial plantar nerve branch, lateral plantar nerve branch, and calcaneal nerves; whereas the saphenous nerve (cutaneous branch of the femoral nerve) innervates the skin and underlying tissue layers along the medial-posterior surface of the lower leg/ankle/foot area. Suitable candidate implant locations for nerve cuffs (which can serve as the IPC of the current invention) are shown proximate to individual nerves.
Figure 10A:
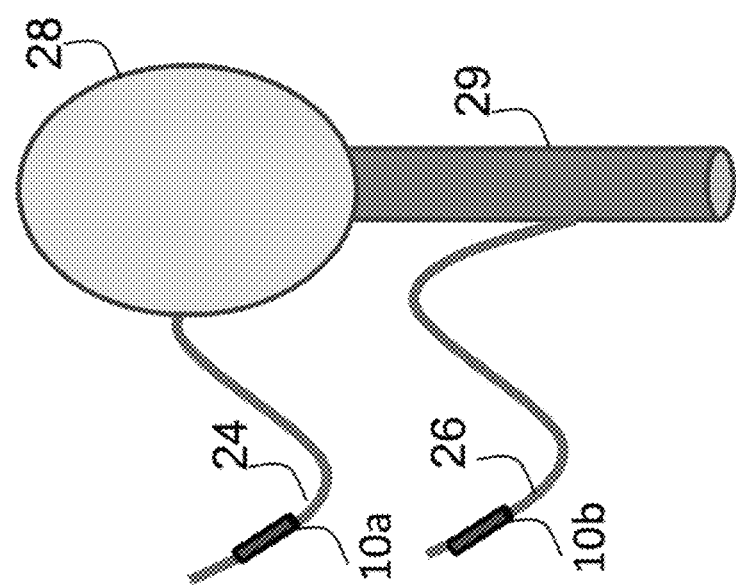
FIG. 10a is a schematic system view containing relevant neuroanatomical landmarks for electrical neuromodulation of the urinary bladder, with the urinary bladder and urethra innervated by the pelvic and pudendal nerves, respectively.

FIG. 10a and FIG. 10b show various embodiments of an enhanced nerve stimulation system, where selective activation of targeted nerves (e.g., pudendal nerve, pelvic nerve, posterior tibial nerve, medial plantar nerve, lateral plantar nerve, calaneal nerve, sacral nerve root and lumbar nerve root) can be achieved by placing an IPC 10 in close proximity to, in direct contact with, embedded within, or wrapped around, these nerve bundles. Depending on a specific therapeutic protocol, one or more IPCs can be used for enhanced transcutaneous nerve stimulation at one or more sites.

In FIG. 10a the urinary bladder 28 and urethra 29 are shown diagrammatically on the left side of the figure as innervated primarily by nerve targets such as the pelvic 24 and pudendal 26 nerves, the electrical activation of which can be enhanced by IPCs 10a and 10b, respectively. One embodiment of a system and method of selective pelvic or pudendal nerve stimulation may be achieved by providing therapy according to a therapy protocol to deliver electrical pulses using a stimulator that is at least one of an intravesicle or intraurethral electrode, or by using at least one electrode array. The stimulator would stimulate nerve targets for which IPC's have previously been implanted (e.g., pudendal nerve). The stimulator may be permanently implanted or temporarily inserted in similar manner as urethral catheterization (e.g., as in cases of spina-bifidda, neurogenic bowel or bladder dysfunction). Selective activation of a neural target which includes at least one subset of nerves within the pudendal nerve (e.g., dorsal genital nerve, nerve to urethral sphincter, and nerve to external anal sphincter) may be achieved by strategically implanting an IPC and stimulating an implanted electrode paired to the IPC using a pulse generator that is external to the patient. Therapeutic stimulation can also be provided using TENS or TMS from various locations such as on the posterior surface (above the gluteus maximus muscle). Potential clinical indications for the paired-use of an IPC and stimulation electrode can include pelvic floor disorders such as urinary retention, urinary incontinence, fecal incontinence, stress incontinence, and pelvic pain.

FIG. 10b shows the nerves innervating the lower leg and foot. The PTN descends down the posterior-medial aspect of the calf before dividing into the MPN, LPN, and calcaneal nerves. The saphenous nerve is a cutaneous sensory nerve that branches off the femoral nerve in the upper thigh. The nerve travels down the medial-anterior aspect of the leg, provides a sensory branch to the knee and continues down the leg to provide sensory innervation of the medial-posterior aspect of the lower leg. Suitable implant locations for nerve cuffs, which serve as the IPCs (10c-f) of the current invention are shown proximate to individual nerves (a cuff is not shown on the calaneal nerve to avoid cluttering of the figure). At least one stimulator 14 can be placed on the skin next to any of the IPCs in order to provide eTENS therapy. In the figure the stimulator appears just above the ankle, and is shown in an anterior portion of the ankle, rather than posterior, to avoid cluttering of the figure. Other locations for the IPCs can also be selected such as positioning an IPC at the level of, or below, a patient's knee in order to enhance stimulation of a nerve such as the saphenous nerve. A number of sites and methods for stimulating various lower limb nerves (which are suitable targets for some embodiments of the invention), and recording responses to the stimulation to measure neural response, are described in Chap 6, p. 125-145, of Electrodiagnosis in Diseases of Nerve and Muscle: Principles and Practice (2013), $4^{th}$ Jun. Kimura (ed), Oxford University Press).

Figures 14D, 14E, 14F:
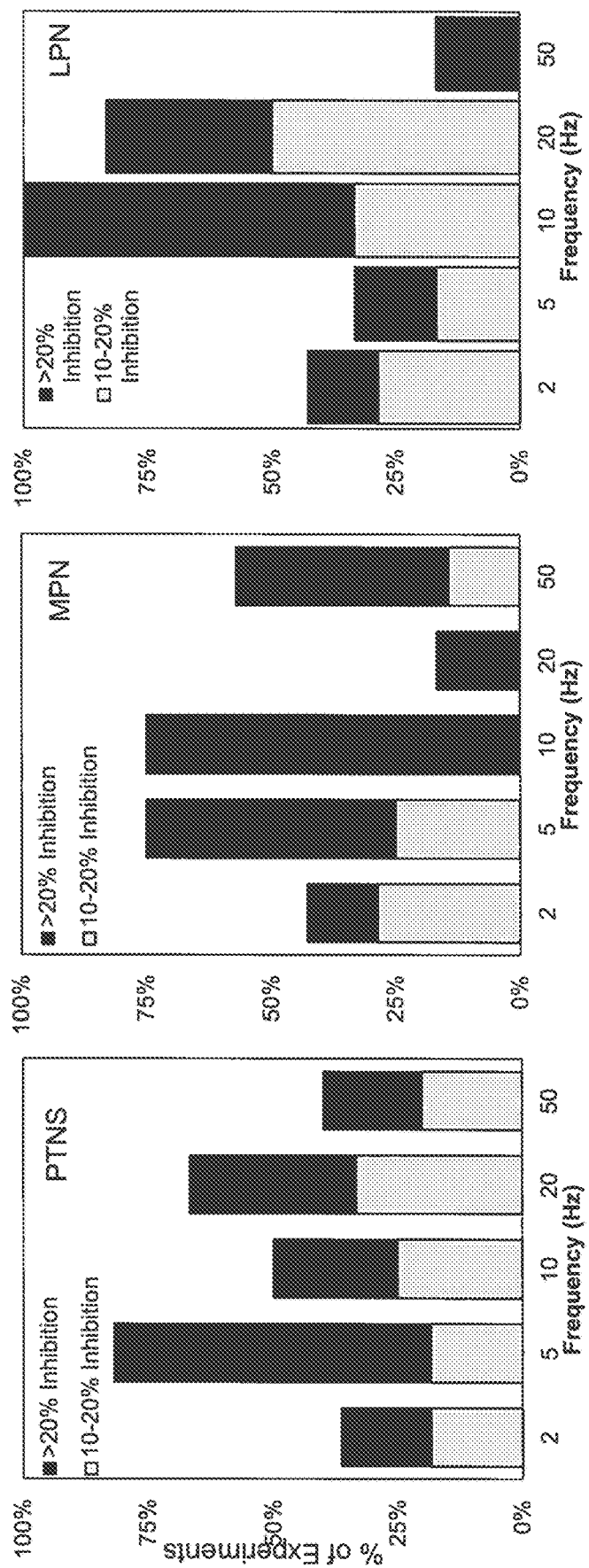
FIGS. 14d, e, f are graphs of summary data of percentage of experiments (total 11 rats) that exhibited a prolonged reduction in BRC (i.e. prolonged bladder inhibition) following each 10-minute stimulation trial of the PTN, MPN, and LPN in anesthetized rats.
Figure 15:
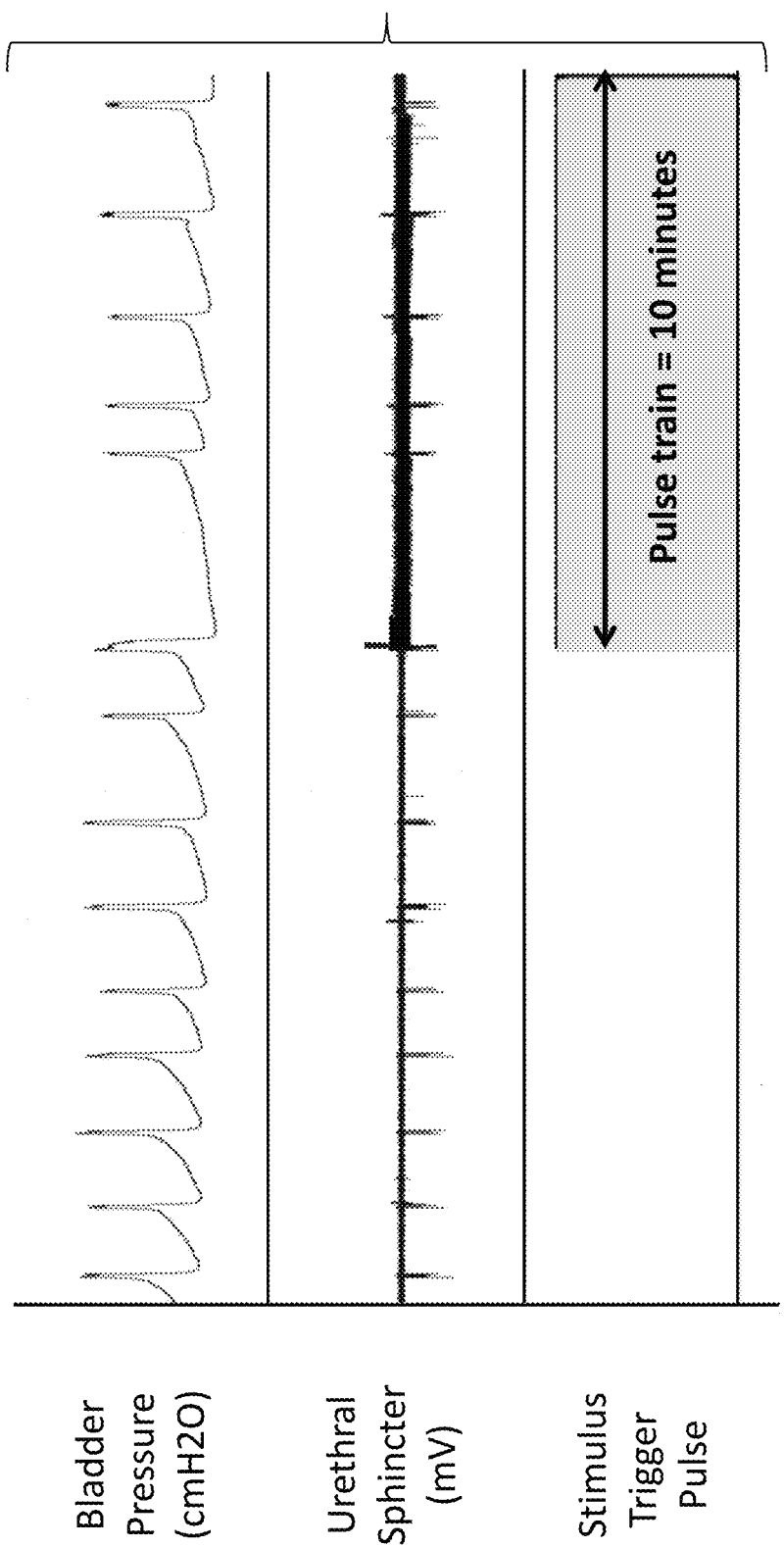
FIG. 15 is a graph of experimental data from an anesthetized rat, where electrical stimulation (0.3 mA, 5 Hz) of the Saphenous nerve (branch was accessed below the knee,) resulted in an acute 25% decrease in BCR during stimulation as evidenced by the top trace, while middle trade shows other recorded activity and the lower trace shows the duration of the pulse train.

The current clinical model of PTN stimulation for the treatment of bladder disorders is that by providing percutaneous stimulation of the PTN "trunk", stimulation is provided to the multiple nerve branches (e.g., LPN and MPN) that converge and pass through this nerve trunk. Stimulation of the PTN is viewed as an efficient manner of providing nerve stimulation in the treatment of OAB since one stimulation target can serve to stimulate multiple relevant nerves. The experimental results which are shown in FIGS. 13-15 were derived using a novel animal model that relies upon a continuous bladder-fill paradigm (repeated filling and voiding) that provides different results than other models of bladder function. This model and nerve branch stimulation paradigms of the experiments that were done, provide a new understanding of PTN stimulation and OAB treatment and show, for the first time, that selective stimulation of nerve branches can provide clinical benefit over full PTN trunk stimulation. For example, for a particular frequency the stimulation of the MPN and LPN both show larger inhibitory changes, than stimulating the entire PTN nerve trunk, in bladder contraction activity relative to a pre-stimulation baseline level. Selective PTN nerve branch stimulation may thus lead to larger therapeutic effects and a decreased number of non-responders. These findings, and the insight provided therefrom which supports the design of new systems and methods of treatment, are a main advantage of the current invention.

The novelty of the experimental finding presented here are further supported by the difference between these results and those reported by (Su et al, 2013) in which the bladder was maintained at a constant volume, whereas the model used here relies upon continuous filling and voiding of the bladder. This supports the idea that if there is no realistic type of voiding provided in the animal model, then the effect of the stimulation which are evaluated at various frequencies will have different effects, than those shown here.

Figure 11:
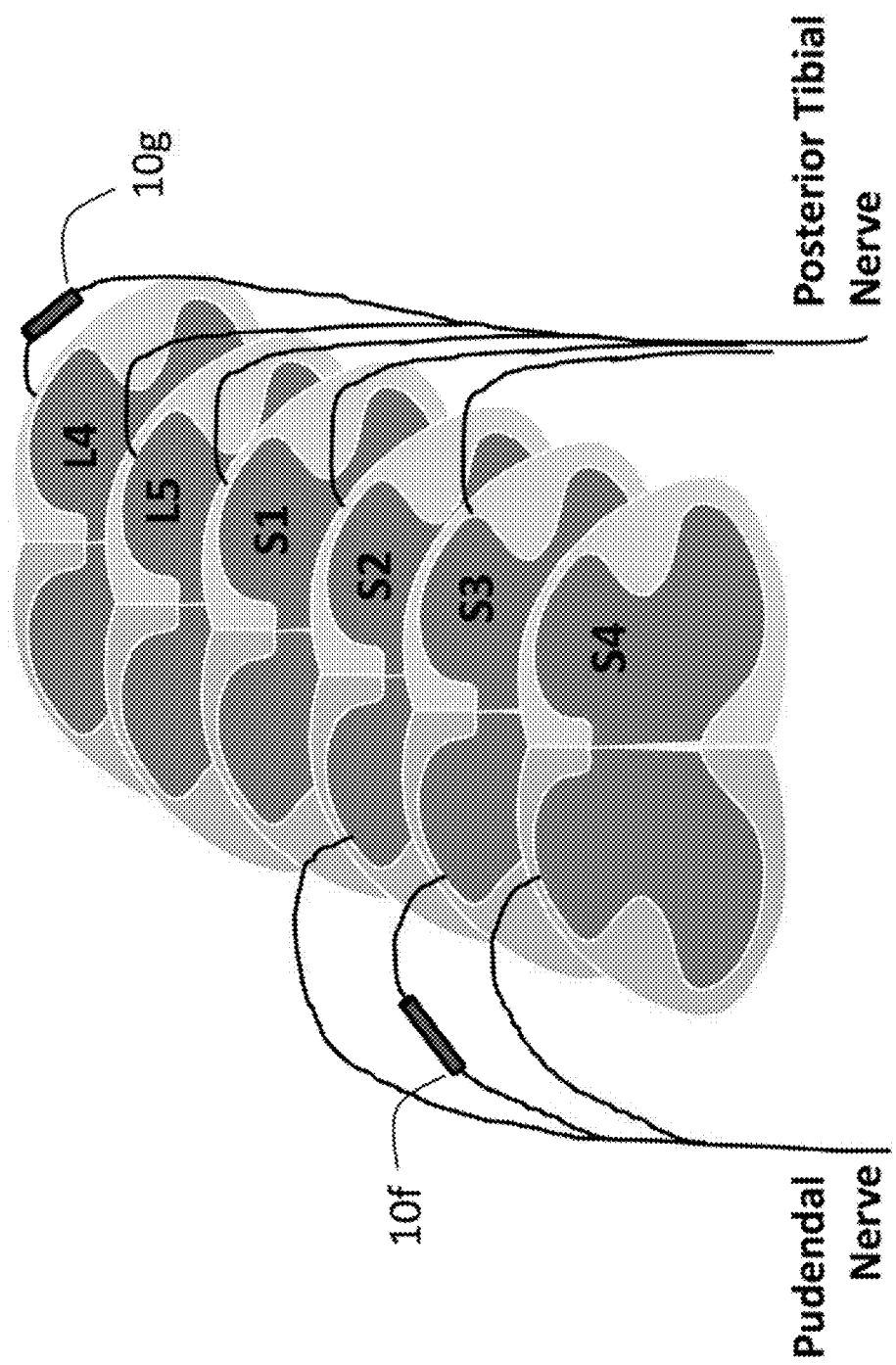
FIG. 11 schematically depicts the spinal nerve roots that converge to form the pudendal (S2-S4) and posterior tibial (L4-S2) nerves. Two surgically placed objects (e.g., nerve cuffs) are indicated as IPCs (10f and 10g) on the S3 and L4 roots, respectively.

FIG. 11 shows stimulation targets which are spinal nerve roots that converge to form the pudendal (S2-S4) and posterior tibial (L4-S2) nerves. Two surgically placed IPCs (10*f*-*g*) are indicated proximate to the S3 and L4 roots. In this example embodiment, the nerves near the IPCs are modulated by stimulators external to the patient such as on the patient's skin (i.e., lower back) superficial the IPC locations. When the IPCs are implanted as part of a therapy for the treatment of pain, then the IPCs can be implanted on one or more nerve roots (as well as on the spinal cord itself) relevant to pain signaling pathways in order to suppress the signals related to the pain.

Figure 12:
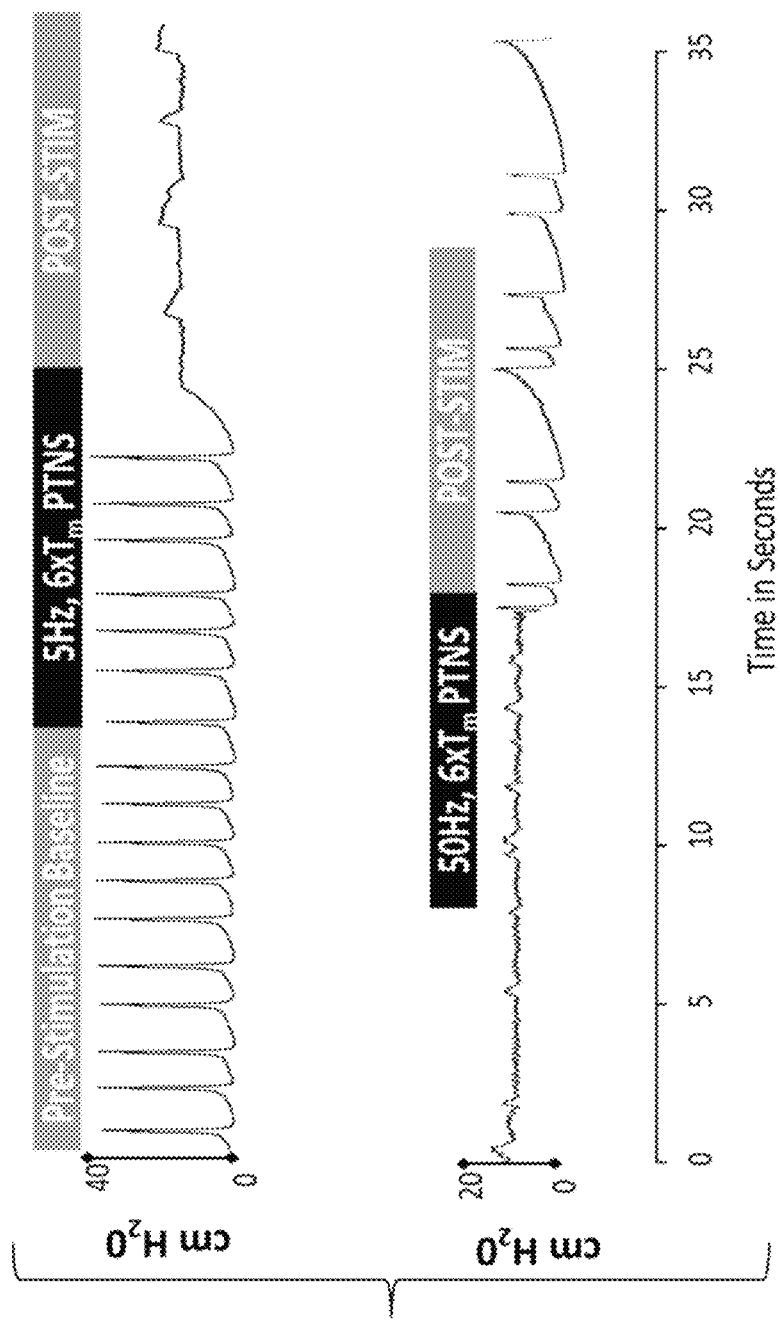
FIG. 12 is a set of graphs of experimental data that characterizes the effects of PTN stimulation on the bladder of urethane-anesthetized rats. At 5 Hz PTN stimulation (top trace) both acute inhibition during stimulation (black bar) and prolonged inhibition following stimulation (gray bar labeled as POST-STIM) were found. At 50 Hz PTN stimulation (bottom trace), only post-stimulation excitation (gray bar labeled as POST-STIM), was found.

FIG. 12 illustrates the results of an experiment in anesthetized rats that indicates that direct electrical stimulation of the PTN can modulate bladder function in a frequency-dependent manner. The experimental setup used to generate this data involved catheterization of the bladder dome in urethane-anesthetized rats. The catheter is connected, in series, to a pressure transducer and a syringe filled with saline. An infusion pump is then used to realize a novel "continuous bladder-fill paradigm", where repeated reflex bladder contractions are elicited (FIG. 12, top trace). The top graph shows a 10-minute train of electrical pulses delivered to the PTN at 5 Hz. In this example of 5 Hz PTNS, a slight but noticeable reduction in the bladder contraction frequency can be visually seen during the 10-minute stimulation trial (relative to the pre-stimulation baseline). This is followed by complete inhibition of the bladder that persists beyond the end of the PTNS trial. In contrast, the bottom graph shows recovery of bladder activity following a 10-minute trial of PTNS applied at 50 Hz. This particular example shows the abrupt transition from a flaccid (passively leaking) bladder before PTNS to one that generates robust sustained bladder contractions following this high-frequency PTNS. The bladder-excitatory effect remains persistent following the termination of PTNS. While the top trace shows an example of a stimulation protocol that can be used to decrease bladder activity, the bottom shows how the stimulation protocol can be used to modulate the bladder to increase contractions.

In this model, the PTN was surgically accessed and a bipolar stimulating nerve cuff electrode was implanted directly onto the nerve. The stimulation amplitude was set at 6 times the threshold required to evoke a foot twitch (i.e., the minimum amplitude that works for this experimental set-up, or "6×Tm"). Although not observed in this example, this bladder-excitatory response typically occurred during stimulation and the evoked activity continued after the end of the 10-minute pulse train into the post-stimulation period.

As already noted, the "continuous bladder-fill paradigm" used to obtain these data is novel over models of the prior art and the discovery that the continuous filling of the bladder causes the stimulation protocol to produce different effects than what occurs with models commonly used in the prior art. Accordingly, the stimulation-related results shown in FIGS. 12 and 13-15 may be absent from, in contrast with, and lead to different conclusions about the clinical efficacy of particular stimulation protocols, compared to results that have been found previously by others.

Figure 13A:
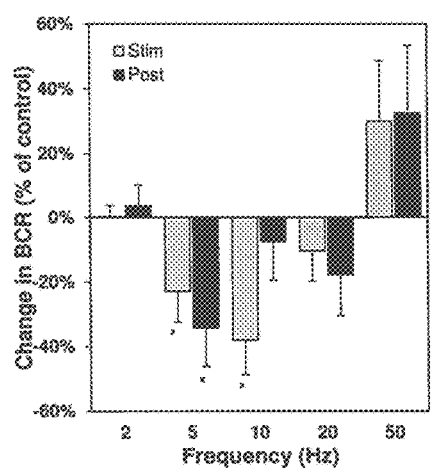
FIGS. 13a, b, c are graphs showing summary data of electrical stimulation of (A) PTN, (B) medial plantar nerve (MPN), and (C) lateral plantar nerve (LPN) in anesthetized rats (e.g. summarized using raw data such as that seen in FIG. 12). Bladder inhibition (defined by % reduction in bladder contraction rate (BRC) with respect to baseline) is observed during stimulation at lower frequencies (e.g., 5 Hz to 20 Hz), whereas bladder excitation is observed at 50 Hz for PTN and LPN stimulation.
Figure 13B:
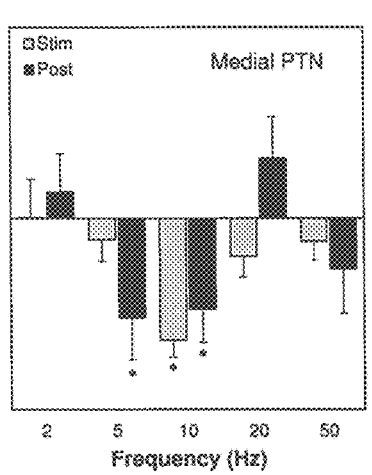
Figure 13C:
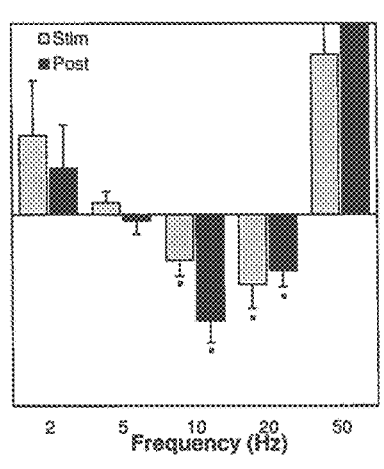

FIGS. 13*a*, 13*b*, 13*c*, shows the summary data from a set of 11 experiments that followed the same PTN stimulation protocol and "continuous bladder-fill paradigm" used in FIG. 12. There is a clear frequency-dependent modulation of the urinary bladder in response to electrical stimulation of the PTN trunk compared to selective nerve branch stimulation as shown FIG. 13*a* for the PTN, FIG. 13*b* for the medial plantar nerve (MPN), and FIG. 13*c* for the lateral plantar nerve (LPN).

FIG. 13*a* PTNS resulted in robust bladder inhibition at low frequencies, such as 5 Hz to 20 Hz; whereas bladder excitation is observed in response to stimulation at higher frequencies such as 50 Hz. It is important to note that each stimulation frequency range can exhibit unique PTNS-evoked responses. Stimulation at 5 Hz and 20 Hz elicits both acute and prolonged inhibition of the bladder; 10 Hz stimulation evoked primarily acute bladder inhibition; and 50 Hz stimulation elicits both acute and prolonged bladder excitation. Although using a stimulation protocol which provides at least one signal modulated within a range of approximately 5-20 Hz as therapy for bladder dysfunction may be utilized, in an alternative embodiment the stimulation protocol can be further tailored if one makes a distinction between results seen for modulation of bladder activity which resulted during stimulation with the results obtained after stimulation (labeled "post" in figure). It should also be noted that the acute response may be just as relevant as the post-stimulation response in the treatment of OAB when the duration of the stimulation is increased beyond the 10 minutes used here, and/or repeated periodically during treatment. However, it should also be noted that when the current system and method is used to provide acute modulation of a bladder condition then the acute response may be more relevant in determining therapy parameters of the stimulation protocol. Accordingly, based on these results, in some individuals, PTNS therapy which includes a stimulation protocol that provides at least one signal in either the 5 Hz or 20 Hz ranges for PTN stimulation may be suitable in a stimulation protocol used to treat idiopathic overactive bladder symptoms. Additionally, a stimulation protocol using a signal in the 10 Hz range for PTN stimulation could be suitable for the treatment of neurogenic bladder symptoms (e.g., spinal cord injury, multiple sclerosis, or diabetes). With respect to high stimulation frequencies, the data indicate that a stimulation protocol using a signal in the 50 Hz range (e.g., +/−10 Hz) for PTN stimulation could be suitable for modulating urinary retention (related to detrusor underactivity).

FIG. 13b shows summary data from experiments (same setup as FIG. 12 and FIG. 13a), where the MPN was activated by direct nerve stimulation. In these rat experiments, selective activation of the MPN evoked robust bladder inhibition at 5 Hz (prolonged) and 10 Hz (acute and prolonged). Although 50 Hz stimulation of the MPN failed to elicit a bladder excitatory response, 20 Hz stimulation appears to elicit a prolonged excitatory effect. In one embodiment, a method using an MPN stimulation protocol having at least one frequency selected from the range of 5-20 Hz can be used to treat OAB, while approximately the 5 to 10 Hz range may be preferred. This data suggests that—in lieu of stimulating the entire PTN—low frequency stimulation of the MPN is well suited for treating OAB symptoms. Additionally, a stimulation protocol using 20 Hz MPN stimulation may help with treating urinary retention. The inconsistency of this excitatory response at 20 Hz suggests that electrical stimulation of the PTN or other PTN branches (e.g., LPN or calcaneal nerve) may be a better candidate for successful mediation of this bladder excitatory reflex. In order to stimulate the MPN, the external stimulators, such as TENS electrodes which provide stimulation alone or in conjunction with IPCs can be situated along the medial-plantar surface of the foot, in regions near the large toe, or other suitable location. Percutaneous, optical, (ultra) sound-based, or other types of stimulation may also be provided using appropriately configured stimulators.

FIG. 13c shows summary data from experiments (using same setup as FIGS. 13a, 13b and FIG. 14a,b) where the LPN was activated by direct nerve stimulation. In these rat experiments, selective activation of the LPN evoked robust bladder inhibition at 10 Hz and 20 Hz (acute and prolonged), while 50 Hz stimulation (similar to PTN stimulation, FIG. 13a) elicits an acute and prolonged excitatory effect. This data suggests that—in lieu of stimulating the entire PTN or the MPN—low frequency stimulation of the LPN (10 Hz to 20 Hz) is suitable for treating overactive bladder symptoms, while 50 Hz MPN stimulation will help with treating urinary retention. In order to stimulate the LPN, in one embodiment, surface stimulation can be delivered along the lateral-plantar surface of the foot, regions near the smaller toes, or other suitable location.

FIG. 14a shows the summary data (from 11 rat experiments) of the positive response rate of acute bladder inhibition (defined as a minimum of 10% decrease in bladder contraction rate (BCR)) that resulted during nerve stimulation. This is expressed as the percentage of experiments that evoked changes in response to stimulation of the PTN, MPN, and LPN. Overall, the frequencies at which nerve stimulation resulted in statistically significant reductions in BRC FIGS. 13a, b, c yielded response rates in the range of 50% to 67%. Interestingly, 10 Hz MPN stimulation yielded an acute bladder-inhibitory response in every experiment, which suggests that this stimulation parameter could be used to maximize the patient response rate for treating OAB, and especially acute bladder symptoms such as urgency.

FIG. 14b shows the summary data (from 11 rat experiments) of the positive response rate of prolonged bladder inhibition (defined as a minimum of 10% decrease in BCR) that resulted following each nerve stimulation trial. This was expressed as the percentage of experiments that evoked changes in response to stimulation of the PTN, MPN, or LPN. Overall, the frequencies at which nerve stimulation resulted in statistically significant reductions in BRC (FIGS. 13a, b, c) yielded response rates in the range of 75% to 82%. Interestingly, 10 Hz LPN stimulation yielded a prolonged bladder-inhibitory response in every experiment, which suggests that this stimulation parameter could be used to maximize the patient response rate of PTNS therapy used for treating OAB, especially chronic overactive bladder symptoms.

FIG. 15 shows sample data that demonstrates the effects of saphenous nerve stimulation on ongoing bladder function. This study was performed in an anesthetized rat that utilized our "continuous bladder-fill paradigm". A 10-minute train of electrical pulses (pulse-width=0.2 ms, frequency=5 Hz, amplitude=0.3 mA) was applied to the saphenous nerve using a nerve cuff electrode. In this single stimulation trial, a noticeable decrease in BRC (approximately 25% decrease) was found that was indicative of reflexive bladder inhibition. This experimental evidence suggests that saphenous nerve stimulation could provide a therapeutic means of treating OAB either as a single nerve target or in combination with other neural substrates (e.g., PTN, MPN, LPN, pudendal nerve), each electrically activated according to effective stimulation parameters.

The experimental results which are shown in FIGS. 12-15 provide novel understanding of peripheral nerve stimulation for treatment of OAB. As shown in FIG. 13a, b, c, selective nerve stimulation can provide therapeutic advantages over full PTN trunk stimulation because, for example, at certain frequencies the MPN and LPN both show larger post-stimulus decrements in BCR relative to the pre-stimulus levels. Clinically, in humans, this may also lead to larger clinical effects of therapeutic stimulation, enable greater time between maintenance treatments, and may lead to a decreased number of non-responders. Moreover, combining the data of FIG. 13a, b, c with the data of FIG. 14a, b, c, indicates that selective MPN and LPN stimulation can lead, not only to larger physiological responses but can also benefit a greater proportion of patients, when compared to PTN trunk stimulation. Although the overall acute response to 10 Hz was about −40% BRC for both PTN and MPN, selective MPN stimulation showed a 100% response rate among all 11 experiments, suggesting that the MPN may provide successful therapy to a greater number of patients than PTNS. Similarly, combining the data of FIG. 13a, b, c with the data of FIG. 14d, e, f, indicates that group mean level of the overall post-stimulation (i.e., prolonged) response to 10 Hz was about −30% BRC for both MPN and LPN during the post-stimulation period. However, when compared to MPN stimulation, selective LPN stimulation not only showed a similar response rate for greater than 20% reductions in the BRC, but it also showed a minimum 10% reduction in BRC in all remaining experiments (i.e., overall 100% response rate). This suggests the LPN may be a superior target for more prevalently providing at least a minimum level of therapy in long-term treatment of OAB.

A number of additional conclusions can be drawn from combining the novel data of FIGS. 13a, b, c, 14a, b, c, and 14d, e, f. For example, the data suggest that treatment using PTN stimulation may provide inferior therapeutic efficacy than selective LPN or/and MPN branch stimulation as reflected in a lower total proportion of responders and a smaller physiological effect (e.g., prolonged at 10 Hz).

Secondly, a system and method of OAB treatment which uses a stimulation protocol that combines stimulation of at least two of PTN, LPN, and MPN targets may produce improved (size and prevalence of) results than using any of these stimulation protocols that utilize a single site. Thirdly, a system and method of OAB treatment which uses a stimulation protocol that combines stimulation of at least two frequencies, applied to at least one of PTN, LPN, and MPN targets may produce improved therapy, than using stimulation protocols that utilize a single site and single stimulation frequency. Additionally, treatment which uses a stimulation protocol of the PTN having a frequency such as 20 Hz, may modulate a nerve branch (e.g., MPN) in manner that causes increases rather than decreases in BRC (e.g., see FIG. 13b). In contrast, selective nerve stimulation of only one of the nerve branches may produce the desired decreased in BRC, without this type of unintended side-effect. These findings, as well as other insights based on these data, serve, in part, as the innovative, novel, and unobvious basis for a number of methods and systems of the current invention. In relation to these results, it is interesting to note that a common Uroplasty treatment uses a stimulation protocol having a signal with current level of 0.5 to 9.0 mA which is modulated at 20 Hz. The data of FIG. 13a suggests that 5 Hz, and possibly 10 Hz, may provide a larger effect of stimulation in the treatment of OAB.

An embodiment of electrically stimulating the saphenous nerve for treating chronic medical symptoms (e.g., overactive bladder) may involve the use of eTENS, where an IPC 10f is implanted on the nerve (FIG. 10b) and is electrically coupled with a surface electrode or stimulator 14. Other possible locations for surgically implanting an IPC may include subcutaneous locations at the level of (1) the knee, (2) upper thigh, (3) pelvic area, and (4) spinal nerves (L2 to L4). The stimulation parameters (amplitude, frequency, duty cycle, etc) applied by surface electrodes at these areas may be similar to those used clinically for PTNS therapy.

In another embodiment, conventional TENS may be used to electrically modulate this cutaneous branch of the saphenous nerve. The surface electrode may be placed on the medial aspect of the lower leg (between the knee and the medial meleolus), or may be placed on the medial-posterior aspect of the lower leg (between the medial meleolus and the plantar surface of the foot).

In another embodiment, implantable electrodes may be surgically placed to electrically modulate this cutaneous branch of the saphenous nerve. The possible locations for implanting such a device may include subcutaneous locations at the level of (1) the ankle, (2) the knee, (3) upper thigh, (4) pelvic area, and (5) spinal nerves (L2 to L4). The electrodes may be a single- or multi-contact (1) lead-type electrode, (2) cuff-type electrode, (3) helical or spiral type nerve electrode, (4) injectable pellet-type electrode, or (5) wire-type electrode. This device may be powered by an implanted pulse generator, external RF power source, TMS source or light source (e.g., visible, laser, infrared, or ultraviolet light) 2.

Figure 16:
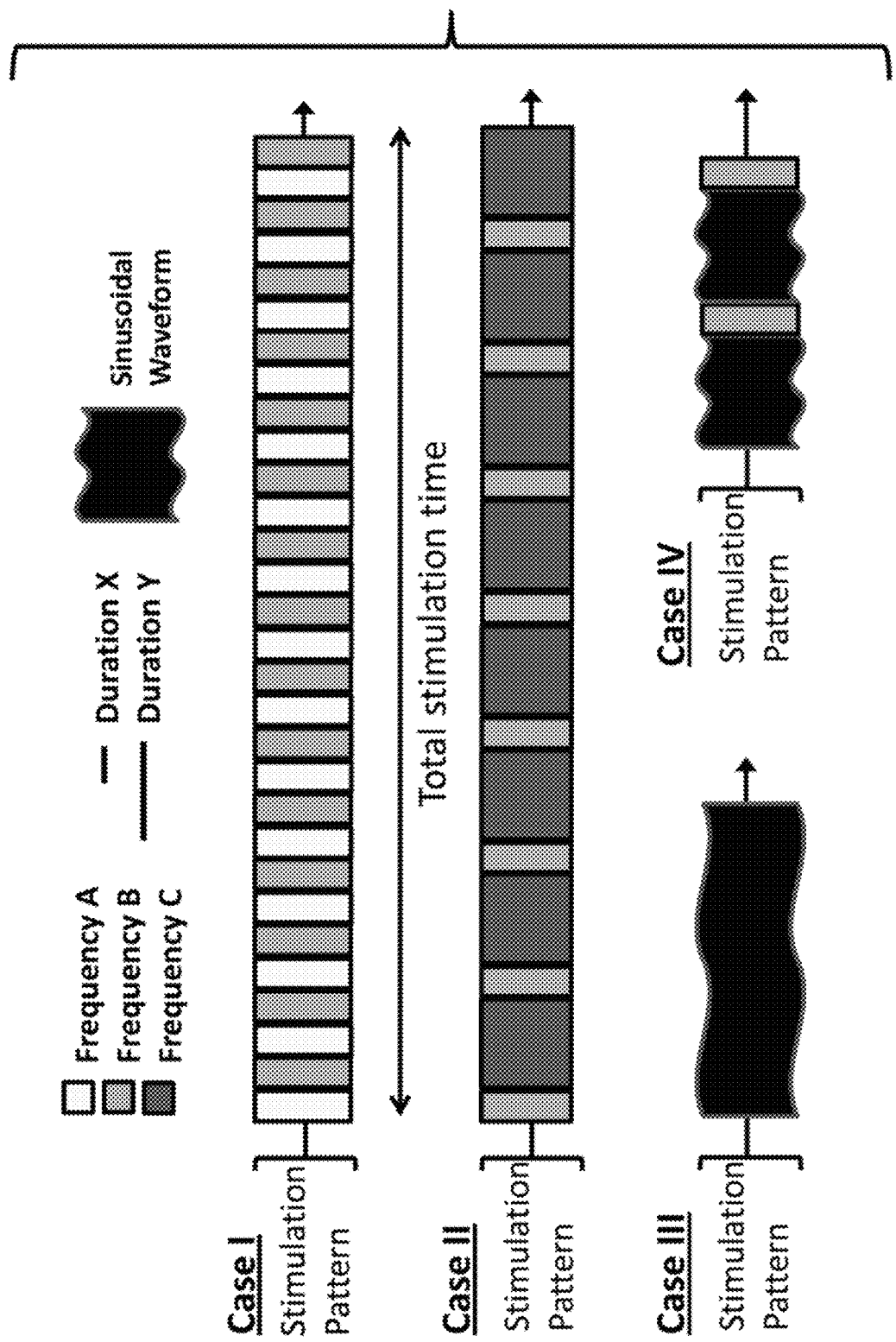
FIG. 16 shows alternative exemplary embodiments of different electrical nerve stimulation patterns that can be used with the present invention to improve various neuromodulation therapies.

FIG. 16 shows sample embodiments of various methods of applying electrical pulses to target nervous tissue. The example presented is based on experimental data (e.g., FIGS. 13-FIG. 14), which demonstrated reflex bladder inhibition when different stimulation frequencies were used. In one embodiment, a method may utilize more than one stimulation frequency in order to provide the advantage of increasing the number of patients that respond to stimulation therapy. A 'hybrid-frequency' stimulation method of activating nervous tissue is presented in cases I and II, where electrical pulses can be, for example, square or rectangular in waveform shape and can be applied in monophasic or biphasic fashion. In one embodiment, the stimulation protocol for OAB treatment requires alternating PTN stimulation at 5 and 10 Hz, MPN stimulation at 5 and 10 Hz, and/or the LPN stimulation at 10 and 20 Hz. Two or more sites may be stimulated at a particular time or the sites can be alternated. One example stimulation protocol can include three different stimulation signals modulated at different rates (A=5 Hz, B=10 Hz and C=20 Hz) and 2 different pulse train durations (e.g., X=1 minute, and Y=6 minutes). The two stimulation signals (e.g. A and B), can both occur for a duration of X (e.g., case I), or the two (or more) stimulation signals (e.g., B and C) can occur in an alternating manner with a duration of X and the other can occur with a duration Y (e.g., case II), which are different. For example, a clinically useful stimulation protocol may be used if a patient can tolerate the first stimulation pattern (B) better than the second stimulation pattern (C) in which Y can be made longer than X. Further to increase patient comfort a pause-duration, during which no stimulation occurs, can be inserted into any stimulation sequence. In addition to comfort, another issue is effectiveness. For example, the first stimulation signal (defined by the first stimulation signal set of parameters) may need to be provided for a longer interval than then second protocol before a desired effect occurs. Other values of the stimulation signal such as pulse width, rise time, waveshape, current and voltage level, in addition to total duration, may be adjusted due to factors such as subjective tolerance, stimulation site, nerve target, acute response to treatment, response to treatment over time, or due to patient data sensed from sensors which are assessed by a doctor or by an algorithm of the system.

In another exemplary method of improving PTN or MPN stimulation (case I), the stimulation protocol is comprised of an interleaved pattern of stimulation in which 1-minute trains of 5 Hz and 10 Hz pulses are delivered throughout a single clinical treatment session. The total stimulation time during a treatment session may be in the range of 30-60 minutes. In a second embodiment (case II), the stimulation protocol occurs by stimulating the LPN with a protocol that has stimulation parameters that define a stimulation pattern with interleaved pulse trains of 10 Hz for 1 minute, and 20 Hz for 6 minutes.

These stimulation paradigms may be delivered using TENS or TMS, with or without an IPC, percutaneous nerve stimulation, ultrasound and laser-based stimulation signals, and by a fully or partially external or implanted neurostimulator. In an embodiment the implanted component may consist of a multi-contact nerve cuff electrode, multi-contact lead-type array, or a multi-contact paddle-type electrode configuration.

The use of alternating stimulation protocols between two stimulation parameter sets that are designed to provide benefit can be applied to the clinical treatment of other disorders as well. For example, the treatment may include vagus nerve stimulation, deep brain stimulation, spinal cord stimulation, etc. The two or more alternating stimulation parameters can be adjusted for each individual patient in order to provide improved treatment. The adjustment may be done using stimulation parameters which were derived using a calibration or testing procedure that occurs before (after, or during) the treatment is provided, and which may also be carried out before each treatment session occurs.

In another embodiment (case III), electrical stimulation may a sinusoidal waveform that is applied to one or more cutaneous surfaces that best activate (1) the PTN, (2) MPN, (3) LPN, (4) calcaneal nerve, and/or (5) saphenous nerve. These areas may include the medial aspect of the lower leg, medial-posterior aspect of the lower leg, posterior surface of the foot, medial aspect of the glabourous surface of the foot, and the lateral aspect of the glabourous surface of the foot. The frequency of the sinusoidal signal may be tuned to, for example, 2000 Hz, 250 Hz, and 5 Hz. According to Koga K et al (Koga et al, Molecular Pain, 2005), these frequencies can preferentially activate Aβ, Aδ, and unmyelinated C-fibers, respectively.

In another embodiment (case IV), both pulse-type and sinusoidal waveforms may be combined to selectively target multiple nerve targets. With a single surface stimulator 14 placed on the medial-posterior surface of the lower leg (e.g., between the medial malleolus and the ankle) and an IPC implanted on the PTN 10e, a stimulating pattern of alternating sinusoidal and pulse-type waveforms is applied. The sinusoidal waveform may be applied at a frequency of 250 Hz to target Aδ-type fibers/receptors within the saphenous nerve, whereas electrical pulses are applied at 5 Hz to target the PTN (refer to FIG. 13a). The duration of each waveform (sinusoidal and pulse-type) may be 5 minutes and 1 minute, both 1 minute, or 1 minute and 5 minutes, respectively.

FIG. 17 shows one embodiment of the invention for the treatment of overactive bladder or urinary retention (i.e., detrusor under-activity) that comprises a treatment method which uses an eTENS system including the combination of an IPC 10e placed on the PTN trunk and a surface electrode 14 placed superficial to the IPC 10e. eTENS stimulation of a patient with an IPC placed on the PTN may be selected if an assessment 48 shows that this might provide suitable therapy. The assessment 48 may include using percutaneous stimulation of the PTN to determine if this is effective in treating a patient and/or produces a desired outcome. If stimulation of the PTN nerve trunk is deemed unsuitable as an outcome of the assessment (e.g., uncomfortable PTNS-evoked sensation or non-satisfactory treatment response by the patient), then alternative stimulation protocol can be assessed by repeating step 48. For example, stimulation of at least one of the MPN or LPN can be assessed, and an IPC can be implanted proximate to either the MPN or LPN if either of these provide sufficient therapeutic benefit. FIGS. 12-14f show data supporting that a stimulation protocol which uses the PTN may produce better or worse therapeutic results than stimulation of the LPN or MPN, and may be successful in patients who did not respond to PTN trunk stimulation. The assessment of the LPN or MPN can occur using a percutaneous or TENS stimulation protocol or may use light, sound, pressure, or other modality to stimulate the nerves during assessment 48. Assessment may also include evaluation of acute responses while the stimulation occurs, or post-stimulation responses which may occur minutes, hours, days or weeks after stimulation. Assessment may entail evaluation of a measure (e.g. bladder activity) in absolute terms or relative to a different period such as a subject's baseline, or comparison to age and sex matched population normative data. Assessment protocols can include use of bladder diaries, assessment of bladder contraction, and other patient data. Assessment can include filling a patient's bladder (e.g., using a transurethral catheter) and then asking the patient to rate a measure while stimulation is provided. For example, a visual analog scale can be used in which the patient rates bladder comfort from 1 (most comfortable) to 10 (least comfortable) or a longer term bladder diary may be assessed. The assessment protocols can also be used during the assessment of the treatment protocol as per step 38. During assessment 38, 48 or treatment 36, the placement of at least one surface stimulator 14 for the stimulation of selected PTN nerve branches could involve the plantar surface of the foot (and/or other suitable location such as toes, lateral or dorsal foot surfaces).

Due to the results of this assessment 38, 48 (or without such assessment), improved therapeutic efficacy may be provided using a stimulation protocol which includes the co-activation (either at the same time or different times) of targets selected from the group including the MPN, LPN, PTN, and pudendal nerve (e.g., dorsal genital) fibers, as is supported by the novel data shown in this specification. In a related embodiment, an additional stimulation may occur without an IPC, or with an IPC located in close proximity to the dorsal (clitoral or penile) nerve or the corresponding spinal roots (e.g., S3). Another therapeutic target involves electrical activation of the saphenous nerve. This can be stimulated directly by percutaneous stimulation, TENS, or as part of a system in which an IPC 14 is be implanted just under the skin surface and coupled to a TENS electrode 14. Supporting physiological data for this reflex pathway is provided in FIG. 15. In further embodiments, specific combinations of the PTN, PTN branches and/or the saphenous nerve may be implemented by surgically placing individual IPCs on each neural target and selectively activating each nerve using target-specific stimulation parameters. In some of these therapeutic embodiments, at least one implantable pulse generating device, may be used alone or in combination with the methods and systems of enhanced electrical stimulation.

In a further embodiment, the models of FIGS. 1a and 1c, are used to select characteristics such as the physical dimensions of, and approximate 3 dimensional locations of, at least one stimulator and IPC as well as stimulation protocols, during the assessment 48. An example of such a method is shown in FIG. 17 in which at least one stimulator is selected and set up for use with an IPC 32 and then used to provide stimulation to modulate tissue of the patient 8. The stimulation occurs according to the stimulation protocol selected in step 34. The stimulation protocol may define the stimulation parameters (e.g., either 5 Hz, 10 Hz, or 20 Hz stimulation) that are used to create at least one stimulation signal that is applied to the nerve target in order to modulate bladder activity. Other parameters of the stimulation protocol which is defined, adjusted, or selected in step 34 may include any characteristic related to the stimulation. The characteristic may be selected from the group of: voltage, current, duration of stimulation, frequency, duty cycle, bursting pattern, burst or non-burst pulse trains, shape of the stimulation pulses or waveforms, pulse width, pulse shape, pulse amplitude, polarity, and other parameters related to various waveform types that have been disclosed. The term stimulation frequency may also be understood to be repetition rate. Various parameters can be set for the stimulation signal and these other parameters may be adjusted in any step that discloses adjusting a stimulation frequency. Additionally, a stimulation protocol can be used in which more than one frequency of stimulation is provided either simultaneously, sequentially, or at different times (e.g. FIG. 16). The stimulation protocol may also be provided according to times of day, pre-programmed times, according to the preferences of the patient or doctor, responsively according to patient symptoms, sensed patient data, or otherwise. In a preferred embodiment the stimulation is intended to produce a desired effect which is to decrease bladder activity or otherwise treat a condition related to OAB. The stimulation protocol can be selected 34 accordingly.

In another embodiment of the invention, at least one selected stimulator 14 is used to provide high frequency stimulation in the 50 Hz range (e.g., +/−10 Hz) to a nerve target such as the PTN or LPN in order to augment bladder activity in a patient desiring treatment of a condition related to detrusor underactivity (e.g., urinary retention). In a preferred embodiment the stimulation is intended to produce a desired effect which is to increase bladder pressure in a sustained manner. The system and method can be achieved percutaneously, using a cutaneous electrode either with or without also implanting an IPC in order on enhance therapy, or otherwise. If an IPC is to be used with the patient 8, this can occur in step 30. The stimulator may be selected in step 32, as part of a fully external, implanted or partially implanted system. Step 32 can include implantation of a fully implantable stimulator and stimulation device. In step 32, the system may be realized by selecting a stimulator which is at least one coil that provides magnetic stimulation either directly to the nerve, or by way of an IPC. In another embodiment, an implanted stimulation device can convert a magnetic field provided by an external stimulator into an electrical field. In step 30, an IPC may be selected according to the stimulator that will be used. Stimulation can be provided for treatment, induction of treatment, treatment maintenance, in combination with other therapy (e.g., drug), or as part of a screening test procedure. At least a portion of the steps in FIG. 17 may be used to carry out an induction, maintenance, or screening protocol rather than an ongoing treatment protocol that is performed in isolation. For example, the treatment protocol can be done as a maintenance protocol in conjunction with periodic percutaneous treatment (as per one embodiment of FIG. 22*b*).

Different portions of the population will respond to particular stimulation parameters (e.g., stimulation frequency) better than others. The correct stimulation frequency for a patient may be derived, for example, using a method which starts with a first protocol (a candidate protocol selected in step 34), as shown in FIG. 17. The selected first protocol 34 can use an initial frequency such as 5 Hz. In the next step of the method that frequency is used to stimulate according to a treatment protocol 36. The results can then be evaluated 38 for a selected time interval. The step of assessing the treatment protocol 38 can include processing data from before, during, and/or after the stimulation occurs and can include a single assessment period or multiple which can span across, for example, minutes, hours, weeks or months. The assessment of the processed data can be done by a doctor, patient, or device of the system. The assessment may be both objective, such as accomplished using an algorithm on sensed data, or may utilize subjective parameters provided by the patient. Data collected for treatment assessment in step 38 may include storage of sensed data in a device memory, requesting that a patient input data into a system device such as a computer, smartphone, or keep a diary/log, or by any other manner of collecting data. The next step can include N iterations of adjusting the stimulation protocol parameters 44, stimulating again 36, and performing N evaluations of treatment in order to obtain treatment test results. The treatment test results can be calculated upon the assessment data which is collected during the assessment. For example, the results of the stimulation using at least 2 treatment protocols (changed in step 44) are compared. In the case where at least one treatment protocol produced a positive treatment result (a result that meets a treatment criterion), then a positive treatment result activity can occur 40.

One positive treatment result activity is that the stimulation protocol that produced the best improvement in the patient's condition can be selected for subsequent treatment 34 and applied 36 during subsequent treatments. Subsequent treatments may only include steps 32 to 36, or periodically the treatment protocol can be again assessed 38 to ensure that treatment is remaining effective. In the case of negative treatment result, then a negative treatment result activity can occur 42. Such an activity is to modify treatment protocol 44 and repeat stimulation 36. Alternatively, a negative treatment result can include IPC explanting (and implantation of an IPC in another location or an IPC with different characteristics), repositioning of an IPC, implantation of another IPC in order to attempt to improve the outcome by adding an additional stimulation site, or other surgical or treatment adjustment. A patient's demographics (age and gender), symptoms, and other patient data may also influence the success of certain stimulation protocol parameters (e.g., stimulation frequency range) in producing a therapeutic effect and may be used by the system and method in order to select at least one candidate protocol 34. The stimulation parameters used for treatment, or the test protocol used to determine at least one clinically effective stimulation parameter, can be selected and adjusted 34 according to patient data, patient demographics, symptoms, or other patient or disease characteristics. The method of FIG. 17 can be applied to the treatment of OAB, or any other condition, disorder, or dysfunction for which treatment may be sought (e.g., vagus nerve stimulation for treatment of headache).

The setting 34 and subsequent maintenance or adjustment of modulation parameters can occur similarly to the methods used in many wired embodiments and according to methods disclosed in the patents cited herein. For example, in some embodiments, the processor 58 may employ an iterative process in order to select modulation signal parameters that result in a desired response which is measured or observed in a patient. Upon determining that a modulation signal should be generated, the processor 58 may cause generation of an initial modulation control signal based on a set of predetermined parameter values of the treatment regimen. If feedback from a feedback circuit in the sensing or processing module indicates that a calculated measure reflects that a nerve has been suitably modulated (e.g., if an increase in a degree of coupling is observed using a correlation measure between measured activity and the stimulation signal, or a change between a non-stimulus condition to stimulus condition exceeds a threshold level criteria related to positive outcome 40), then processor 58 operate in a similar manner or operate according to a successful outcome operation. If, on the other hand, an evaluation 38 of the "feedback signal" suggests that the intended nerve modulation did not occur 42 as a result of the provided modulation signal or that modulation of the nerve occurred but only partially provided the desired result (e.g., movement of a patients tongue only partially away from the patient's airway while still allowing for unwanted blockage in a method which is used to treat apnea or aspiration), then processor 58 may change one or more parameter values 44 associated with the modulation control signal (e.g., the amplitude, pulse duration, etc.).

In the case where no desired tissue modulation occurred, processor 58 may modify the protocol 44, such as increase one or more parameters of the modulation signal periodically or otherwise until the "feedback signal" or calculated measure indicates that successful modulation has occurred. Further, in the case where tissue modulation occurred, but this did not produce the desired result, the processor 58 may attempt at least one other stimulation paradigm that has been defined in the treatment regimen in order to attempt to provide a different outcome. When a different outcome does not occur, then the treatment regimen may be configured to alert a patient or physician to this result or at least store this result in its memory. In one embodiment this alert may request that a patient move the external stimulator or assess its location in order to re-evaluate the suitability of the pairing between the stimulator and IPC, in order to insure that there is a sufficient degree of coupling between internal and external system components. For example, where stimulation of a nerve causes the tongue to move only partially away from the patient's airway, additional stimulation may be desired. However, because the tongue has moved at least a portion of the desired distance away from the airway, the stimulator may be moved closer or more optimally with respect to the IPC 10 to increase the degree of coupling. Accordingly, after this physical movement, the energy required to move the tongue a remaining distance to a desired location may require a smaller amount of power than what was supplied prior to the last stimulation-induced movement of the tongue. Based on a newly determined degree of coupling, the processor 58 or patient can select new parameters for the stimulation signal that is subsequently used.

In one mode of operation, which is an assessment routine, the processor 58 may be configured to sweep over a range of parameter values until desired nerve modulation is achieved. For example, the stimulus amplitude of the modulation signal may be ramped up to a point which is higher than that which would be used during stimulation, or may remain higher than any level that would be used in longer term stimulation. This may allow a patient, or a sensor which senses data from a patient, to easily measure an effect that indicates that the external and internal components are correctly aligned. After the assessment routine has confirmed correct alignment, the patient can then initiate therapy using the normal levels of the modulation signal. Alternatively, if the result does not indicate that modulation occurred, then the external device may be moved and the assessment repeated.

The stimulation provided to the nerve targets in FIGS. 10 and 11, or other targets stimulated during treatment, may occur using a system configured for using cutaneous electrodes to provide transcutaneous electrical pulses to a nerve or to nerve +IPCs which are surgically placed on, around, or near the intended nerve targets. Stimulation may also be provided by systems and methods designed to deliver electrical pulses using one or more of percutaneous electrodes, cutaneous electrodes, implanted electrodes, implanted stimulation devices powered by magnetic means, implanted electrodes powered by electrical means, and implanted electrodes powered by an implantable pulse generator. Further, the nerves may be modulated by electrical, magnetic and/or chemical means. Drugs may be provided by injection, orally, or otherwise, prior to, during, or after, electrical nerve modulation during treatment. Nerve activity may also be modulated by surgical, pressure, optical (e.g., laser stimulation), (ultra-)sound, genetic, or other means of influencing nerve activity during therapy. The stimulation can be provided chronically, acutely, periodically, or responsively by a doctor, patient, or device having sensing capability. For example, stimulation could be provided for 15 minutes each day, or may be provided in response to bladder pressure which is sensed by a sensor. Stimulation can be provided that is responsive to patient's needs. For example, a patient may use an external device to communicate with an implantable device and cause it to operate to provide stimulation 40 minutes after eating lunch in order to cause urination to occur while the patient is in the lavatory. Alternatively, or additionally, electrical pulses may be delivered using external stimulators at appropriate locations such as along the ventral (plantar) surface of the foot, where IPCs are implanted to enhance stimulation of PTN branches.

Treatment of Incontinence Related Disorders Using Pudendal Nerve Co-Activation

Some studies in anesthetized rats have only demonstrated reflexive bladder inhibition during PTN stimulation while failing to show an excitatory effect (e.g., Su et al., Am. J. Physiol. Ren. Physiol. 2012, Su et al., NAU 2013). These prior studies found that only 10 Hz PTNS was effective at inhibiting the bladder in rats. One difference between the experimental setups used in this prior art and that used to derive the results disclosed herein is the provision of continuous urodynamic bladder filling ("Continuous bladder-fill paradigm"). The prior art studies used an isovolumetric bladder model in which there is no fluid flow through the urethra during bladder contractions. In contrast, the continuous fill model used to generate the data of FIGS. 13-15, and elsewhere, shows that these unexpected bladder reflexes (both inhibitory and excitatory) are produced when both the PTN and pudendal nerve (urethral) afferents are simultaneously activated. A method of using this model to derive candidate stimulation parameters which can be used for treatment using simultaneous stimulation of two nerves is an aspect of the current invention.

Although the influence of PTN (Su et al., Am. J. Physiol. Ren. Physiol. 2012, Su et al., NAU 2013) and pudendal nerve (Peng et al., Am. J. Physiol. Reg. Int. and Comp. Physiol. 2008) afferents on bladder function has been shown individually, the combined effects of activating both pathways has not previously been demonstrated since the prior models do not provide for combined activation. The combined activation is more than just the sum of the multiple reflex pathways because the effects of stimulation, as well as stimulation at particular frequencies, using only 1 nerve is different than the case where other nerves are also activated. The novel model disclosed here, combined with the lack of success of other prior art models to yield similar data, allowed the discovery of this relationship which serves as the basis for some embodiments of the disclosed invention. The simultaneous stimulation has been shown to produce clinically effective stimulation in a model where the bladder is modulated by a first stimulation site (e.g, pudendal and or sacral, and or pelvic nerve) when this occurs with co-activation of stimulation of a second site (e.g., PTN or MPN or LPN). Further, by removing the modulation of the bladder by the first site, the stimulation at the second site becomes much less effective producing bladder modulation. These findings support the novel approach of modulating bladder function by co-activating PTN, LPN, and/or MPN as well as the pudendal nerve afferents in a patient suffering from a urological disorder. Accordingly, in one embodiment of the method shown in FIG. 17, at least one of the steps 30-36 can be adopted so that both the pudendal nerve and the PTN or PTN nerve branch are both stimulated.

In one embodiment, shown in FIG. 10*a-b* electrodes or IPCs are implanted around, or in close proximity to, nerves in the region of the foot as well as on or near 1) the pudendal nerve, either the urethral sensory or the dorsal genital nerve, 2) the posterior tibial nerve, and 3) the saphenous nerve. Up to three independent stimulation sources may be used to deliver electrical stimulation to these nerves. Further, in some embodiments at least three IPCs 10 may be surgically placed on or around spinal nerve roots that best represent the sensory afferents of the pudendal, posterior tibial, and saphenous nerves as illustrated in FIGS. 10a-b and 11. In one aspect of this latter embodiment, surface electrodes could be applied on the lower back, and more specifically may correspond approximately to the locations of the sacral and lumbar nerves. Stimulation can then occur using various setups including the use of external stimulators and IPCs 10 and/or at least one neurostimulator having at least one implanted component. Transcutaneous pulses can be delivered by two or more electrodes or a surface array of multiple-contact electrodes (e.g., two or more electrodes can be placed on the patient's back using the system of FIG. 18a), in which specific contact(s) can be used to selectively activate targeted spinal roots, with or without the use of IPCs.

In addition to stimulating the entire pudendal nerve at a particular stimulation site, the coactive stimulation may be applied to the any of the particular branch of the pudendal nerve (e.g., dorsal genital nerve or urethral sensory nerves), or to the pelvic nerve branches (e.g., bladder neck sensory nerve). Further, the co-active stimulation parameters for the nerve branches maybe the same, or different, as those just disclosed for the full pudendal nerve.

The timing of electrical stimulation of both pathways (e.g., PTN and pudendal) may be applied in a synchronous or asynchronous manner. The stimulation frequencies may also denote an "average rate" at which electrical pulses are delivered to the nerve. In addition to applying pulses with a constant inter-pulse interval (e.g., 20 Hz=50 ms inter-pulse interval), electrical pulses may be applied in bursts or varying duty cycles that will approximate the stated "stimulation frequencies".

Therapeutic electrical stimulation for OAB can be applied in varying doses (e.g., duration=5 minutes to 1 hour) and intervals (e.g., daily, twice-daily, or weekly) that both maximize therapeutic efficacy and patient comfort. For the treatment of urinary retention, electrical stimulation may be applied up to 30-minutes before and during the "anticipated time" to empty the bladder. Further, a sensor, such as an implanted sensor for measuring patient data related to bladder volume would facilitate the effective use of simultaneous (e.g., PTN +pudendal nerve) stimulation. A stimulation system having at least one implanted component and having sensing module of obtaining sensed data would be one suitable candidate system.

Based on the results of FIGS. 13-15, a further embodiment of treatment for bladder disorders may involve the stimulation of at least one of the PTN nerve branches (MPN, LPN) and/or saphenous and possible concomitant activation of the pudendal nerve (dorsal genital or urethral sensory). The ability to activate these excitatory and inhibitory bladder reflexes by selective PTN branch stimulation suggests that multiple combinations of neural pathways and stimulation frequencies can be utilized for improving therapy for bladder disorders. The ability to fine-tune the therapy for OAB or urinary retention patients can significantly improve overall therapeutic effectiveness (degree of improvement in bladder symptoms), increase the percentage of responders to therapy, and increase long-term patient compliance to treatment.

Based on the results of FIGS. 13-15, a further alternative embodiment of treatment for OAB involves providing a first stimulation signal in the 5 Hz range for the PTN, MPN, and/or saphenous nerve. The method can also include providing a second stimulation signal to provide simultaneous pudendal nerve stimulation. The second stimulation signal can be in a range from 5 Hz to 20 Hz, or 2 Hz to 50 Hz. The second stimulation signal can alternatively, or additionally, be used to stimulate a nerve target which is the sacral nerve and/or pelvic nerve (e.g., via S3). The simultaneous stimulation, for example, the setup of FIG. 11 showing IPC implanted to allow co-activation of both S3 and L4 nerves (e.g., at the nerve root sites, which may also be stimulated without the IPCs), can produce better therapeutic effects than that of either single nerve target in isolation.

Based on the results of FIGS. 13-15, a further embodiment of a system and method for treatment of OAB may involve providing 10 Hz stimulation of at least a first nerve target including the PTN or MPN or LPN or saphenous. A second stimulation signal can also be used to provide co-activation of the pudendal, sacral, and/or pelvic nerve stimulation. The second stimulation signal can occur at 1 Hz to 100 Hz, but more preferably between 2 Hz to 50 Hz.

A further embodiment of treatment for OAB involves providing a first stimulation signal of 20 Hz to at least a first nerve target which is the PTN, LPN or saphenous nerve. A second stimulation signal can provide approximately simultaneous co-activation of the pudendal nerve using 2 Hz to 25 Hz stimulation.

A further embodiment of treatment for OAB involves providing a first stimulation signal of 50 Hz to a first nerve target which is the PTN or LPN. A second stimulation signal can provide co-activation of a second nerve target which is the pudendal nerve stimulation at 2 Hz to 50 Hz. This embodiment can be used to increase the bladder activity of a patient.

A further embodiment of treatment for OAB involves providing a first stimulation signal of 20 Hz to a first nerve target which is the MPN. A second stimulation signal can provide co-activation of a second nerve target which is the pudendal nerve stimulation at 2 Hz to 50 Hz.

In another embodiment, a first nerve target (e.g., the PTN or MPN) is provided with stimulation that occurs periodically while simulation of a second nerve target (e.g., S3) is chronically provided such as by an implanted neurostimulator. Various stimulation protocols may be designed so that stimulation at the first and second nerve targets occurs at different or overlapping times. However, as has been disclosed, approximately simultaneous co-activation by stimulation of the second site augments the influence that stimulation at the first site has in modulating bladder activity. In the above embodiments, the stimulation parameters for the first site and second site, include stimulation parameters for the second site which are based upon the data of FIGS. 13-15 and selecting those frequencies which were found to provide larger modulation. Alternatively, different stimulation parameters can be used for at least 2 nerve targets which are stimulated.

Increased Therapeutic Benefits

Based on the results of FIGS. 13-15, a novel system and method of selectively stimulating the various PTN nerve branches may offer improved therapy as realized in a number of alternative embodiments. For example, a stimulating electrode that targets the tissue of, or proximate to, large toe (with a return electrode located on the medial surface of the foot, or elsewhere) can be used to activate the MPN; whereas a different stimulating electrode can be located to provide stimulation to a target near the three smaller toes to activate the LPN (with a return electrode located on the lateral surface of the foot, or elsewhere). The stimulators may be applied and held in place using conductive electrode cream as is often done with TENS, or may also be incorporated into an elastic band, or sock. The limited efficacy of transcutaneous or percutaneous PTN stimulation can be used to highlight the some of the benefits of selective PTN branch stimulation. During stimulation of the entire PTN, the medial and lateral plantar nerves as well as other nerves that converge in the PTN, such as the calcaneal nerve are all electrically activated.

Activation of the calcaneal nerve may not provide sufficient therapeutic benefits, but instead may cause great discomfort to a patient as a function of the stimulation parameters. For example, the unwanted electrical activation of such non-targeted nerve fibers can limit the total amplitude of the stimulation signal and thereby limit the sufficient recruitment of targeted fibers (medial or lateral plantar) needed for suppressing bladder symptoms. Further, even at larger amplitudes, the PTN stimulation modulation of bladder activity can be less than that provided by selective nerve branch stimulation. As demonstrated by Su et al (Am. J. Physiol. Ren. Physiol. 2012), there is an upper limit of the stimulation amplitude (shown as 4×Tm in rats), beyond which PTNS fails to suppress bladder activity. Selective nerve branch stimulation can provide advantages which enable TENS therapy to occur either at home or in the clinic, rather than requiring percutaneous stimulation to produce benefit.

Electrically stimulating more than one PTN nerve branch, as occurs with PTN stimulation, may cause certain nerve fibers to produce small effects, no effect, uncomfortable/painful side-effects, or effects opposite to that of the intended modulation (e.g., suppression) of bladder activity. For example, electrical stimulation of the entire PTN at 5 Hz produces post-stimulation inhibition which is similar to that seen when stimulating only the MPN (FIGS. 13, 14b) while having little or even an opposite effect via stimulation of the LPN. Selectively activating a specific nerve branch, rather than the entire PTN, may provide advantages such as producing less side effects, the ability to maximize the number of recruited nerve fibers, and greater treatment efficacy. Further, at higher stimulation frequencies, selective PTN branch stimulation may also provide an effective means of generating or increasing bladder contractions and thus improving voiding efficiency. The inability to empty the bladder is characteristic of what is called urinary retention, where among myriad factors the underlying pathology may involve detrusor underactivity. As an example in an anesthetized rat model, stimulation of the PTN at 50 Hz produces about a 30% increase in BRC as a % of control (pre-stimulation) while stimulation of LPN produces 130% increase (the response in FIG. 13C extends beyond the top of the graph). In contrast, stimulation of the MPN generally produces a decrease rather than increase in bladder activity at this higher stimulation frequency. These data suggest that bladder excitation by stimulation of the whole PTN is partially retarded by co-activation of the MPN (although the PTN response is not the simple net effect of modulation of PTN and LPN). As such, a system and method which uses a stimulator for providing at least one stimulation signal in the provision of selective activation of the LPN may improve the treatment of detrusor underactivity compared to PTN. Selective stimulation of individual PTN branches may be accomplished using percutaneous, TENS, magnetic and other stimulation methods as are disclosed herein.

The evidence presented here strongly supports the notion that selective PTN branch stimulation may provide a means of significantly increasing not only the percentage of patients that currently respond to PTN stimulation therapy (range=59% to 70%), but also improving the extent to which unwanted bladder symptoms are suppressed and abnormal bladder activity is treated. Selective PTN branch stimulation can electrically activate one nerve at a particular amplitude and frequency or to multiple nerve branches, either simultaneously or in an alternating fashion.

Lastly, it should be noted that the experimental results shown in FIGS. 13-15 were obtained using electrical pulses applied at 6 times the threshold for motor movement of the foot in anesthetized rats. Although this is significantly higher than what is used in humans (typically the threshold for foot twitch), the use of, and effects caused by, anesthesia may be partially responsible for such high stimulation amplitudes. The benefits of different stimulation sites and signals as defined in stimulation protocols that are used in humans will likely depend on the maximum stimulation amplitude that is well tolerated by individual patients.

Induction and Maintenance Therapy for OAB

FIG. 22c shows one embodiment of the current invention as a method of treating OAB that comprises combining a first step of providing a first treatment protocol 252 such as stimulating the PTN percutaneously during a first treatment interval, which may occur inside or outside of a clinic, and the second step of providing a second treatment protocol 256, during at least one second treatment interval, such as an additional therapy that may include at least one of selective PTN branch stimulation including, for example, LPN and selective MPN stimulation. The therapy provided during the second treatment protocol 256 is realized using either transcutaneous or percutaneous stimulation, and/or stimulation which utilizes an implanted device or IPC to improve transcutaneous stimulation. The second treatment protocol 256 can be provided concurrently, at approximately the same time, or within the same treatment session as the primary treatment protocol 252 (e.g., percutaneous stimulation in the clinic). Alternatively, the second treatment protocol 256 can be provided as maintenance therapy that occurs between first treatment protocol treatments using the first therapy 252 (e.g., clinically based percutaneous treatment sessions in a clinic). The additional therapy provided by the secondary treatment protocol 256 can be provided using an external device configured to provide different types of stimulation signals (e.g., a TENS device, in the patients home). The provision of secondary therapy 256 can also be provided other stimulation signals and modalities such as RF-based stimulation, light/laser based stimulation, sound/ultrasound based stimulation, or other modes of stimulation that use various technologies as are disclosed herein. The provision of secondary therapy 256 can be implemented using an IPC which is used in conjunction with an external stimulator to provide an electrical, ultrasound, or laser stimulation signal other type of enhanced nerve stimulation, as disclosed herein. The secondary therapy 256 can comprise a secondary stimulation protocol that stimulates cutaneously located nerves (e.g. saphenous) while the first therapy protocol provides a first therapy that stimulates deeper nerves (e.g. PTN). In addition to providing the first and second stimulation treatments, in one alternative embodiment, the effects of these treatments can be assessed 254, 258 and used to adjust at least one of the treatment protocols. For example, if therapy does not meet at least one therapy criterion then a treatment such as the second treatment can be adjusted by changing the stimulation protocol according to at least one of the following: changing from LPN to MPN stimulation, changing from MPN to LPN stimulation, and changing a characteristic of the stimulation signal that is used. Alternatively, the patient response to the first stimulation protocol can be used to adjust the second stimulation protocol 256 (arrow E). For example, if percutaneous treatment of the PTN is found to produce a large therapeutic response at a particular frequency, then that same frequency can be used in the selective nerve branch stimulation. Alternatively a different frequency range can be selected for the secondary stimulation protocol. As shown in FIGS. 22c (arrows C and D) the primary and secondary treatment protocol may simply be provided in an interleaved fashion. When the secondary treatment protocol 256 is home based, it may be repeated several times before the first (clinic based) protocol 252 is again repeated. The secondary treatment protocol can be home based and can be provided by the patient one or more times each day, one or more times each week, or as infrequently as one or more times each month, depending upon such factors as the patient response to treatment. Regardless of whether the secondary treatment protocol is provided in a clinic or at home, this may occur during stimulation sessions that each range from 30-90 minutes. The primary and secondary treatment protocols which define the provision of the first and second treatments 252, 256 may include stimulation parameter that define, for example, duration of treatment, inter-treatment intervals, and the stimulation signal, target nerves, and method of providing stimulation to a target nerve. These stimulation parameters can be adjusted according to the patient or doctor based upon an assessment of the patient response. The assessment of the patient response to treatment which occurs in steps 254, 258, and 260 can include assessment of patient data, and can be used to adjust the stimulation treatment protocols in various manners. For example, assessment of the patient response can lead to increasing or decreasing the interval between stimulation treatment, changing stimulation parameter such as those related to voltage, stimulation site, and duration of each treatment.

Additional embodiments for Therapy for OAB

In one embodiment, a method and system for improving nerve stimulation treatment efficacy in a refractory patient, who has been assessed 254 as not responding sufficiently to a first treatment protocol which is TBN treatment, comprises administering a second treatment protocol 256 which is a combination therapy. The combination therapy can comprise combining stimulation of the TBN with stimulation of one of the LPN or MPN (or LPN can be combined with MPN). The stimulation is at least one of transcutaneous, with or without an IPC, percutaneous, or may be provided by an implanted device. The stimulation may be, for example, electrical, magnetic, optical or (ultra)sonic. Because the LPN and MPN can provide different efficacy than TBN stimulation, the combination therapy stimulation may produce larger and more consistent results than any of these alone. Rather than applying this combination treatment to a refractory patient, the therapy may simply be applied to a patient. The combination therapy may occur at the same time, at different times, and one may occur unilaterally, or one stimulation signal can be applied to the left side of body while the other is applied to the right. When this combination therapy is accomplished by one device 50, the device should be provided with a signal generator that is able to provide at least two independent stimulation signals to stimulate two therapy targets of a patient to implement either monopolar or bipolar therapy at each site. Alternatively, a signal generator module 62 may contain two or more pulse generators, each of which is configured to provide selected stimulation protocol to a nerve that is being treated by the device 50, according to combination therapy defined in a therapy protocol.

Because combination treatment may produce unknown or unwanted efficacy, the system and method of treating an patient with bladder dysfunction can comprising administering stimulation treatment with a first stimulation protocol which is TBN stimulation for a first period 252, and if assessment of response to the stimulation 254 suggests that the stimulation is not effective, an alternative second treatment protocol is selected 256 and used to provide at least one of LPN or MPN. Alternatively, the first stimulation protocol can comprise treatment of the LPN, and then a second protocol stimulates TBN or MPN if the first protocol is found not to be effective. The first stimulation protocol can also be of the MPN, which is then replaced by a second stimulation protocol that includes LPN or TBN stimulation if this is not found to be effective.

Systems and Methods for Providing Nerve Stimulation

Figure 18A:
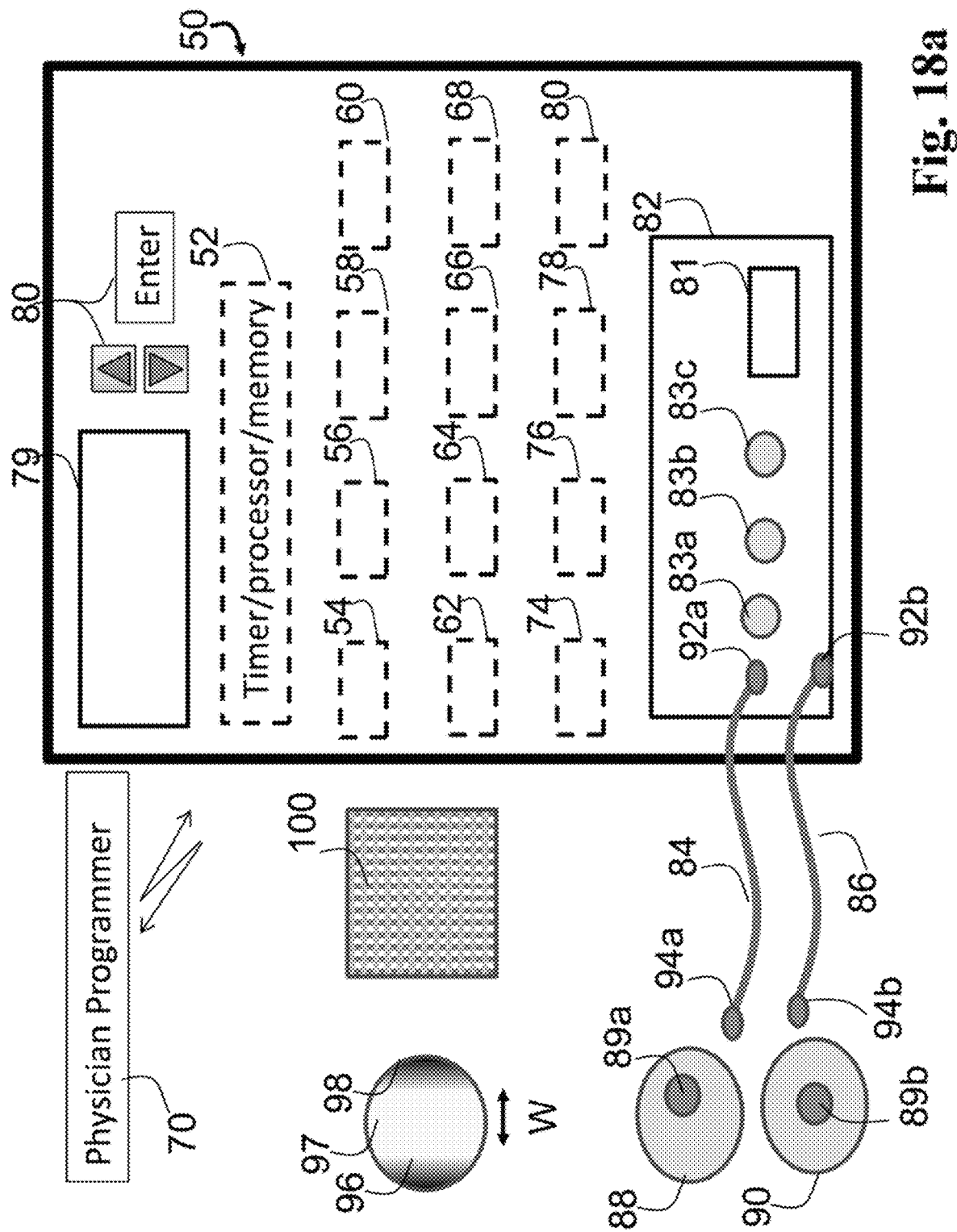
FIG. 18a is a schematic diagram of a tissue stimulation system which may be used to realize the current invention including the provision of tissue stimulation.

FIG. 18a shows a nerve stimulation device 50 for realizing the methods and systems of the current invention. The device 50 is illustrated with modules and components which can be included, omitted, or adjusted in various embodiments. The device 50 comprises a control module 52 having control circuitry for controlling the various modules such as the stimulation module 54 and sensing module 55 according to stimulation protocols and parameters stored in the protocols and parameters module 66. The control module 52 has a timing module 56 including a real time clock and a timer, a processing module 58 including at least one processor for operating software, information and parameter settings that are stored in memory module 60 and which allow for control of device 50 operation. The stimulation module 54 controls a waveform generator/signal processor module 62 that contains circuitry for generating pulses or arbitrary waveforms including alternating current (AC) and/or direct current (DC) signals to be used by electrical, magnetic, optical, sonic, ultrasonic or other types of stimulators to provide stimulation signals to the patient. The sensing module 55 contains circuitry for conditioning and analyzing sensed data and can also for providing power to, and/or communicating with, sensors. An AD/DA module 64 allows for conversion of input and output signals as well as amplification, digital signal processing, filtering, conditioning, and also contains safety circuitry to ensure patient safety. The AD/DA module 64 may also contain circuitry for multiplexing signals across different sensors or stimulators. The apparatus 50 also includes a communication module 68 for providing wired and/or wireless communication with other devices (e.g. an IPC which has communication circuitry to communicate with the apparatus, a physician programmer 70 or patient external device (EXD) 72. The communication module 68 can communicate with a computer at remote medical facility (which may serve as a second type of physician programmer 70' that allows device communication and programming to occur remotely) either directly, or via the EXD 72, using wireless communication such as a Bluetooth or WiFi connection. All wired or wireless communication can be realized at least partially using the internet, a local area network, and may also include means for magnetic, radiofrequency (RF), optical, sonic, and/or other modes of communication with other devices. The communication module 68 and/or EXD 72 may include circuitry and routines for establishing WiFi, Bluetooth, cellular, magnetic, RF, electrical, optical, sonic or other types of communication can contain communication/interface ports 82 for connection using USB, Firewire, and the like. The communication module 68 of the device 50, as well as communication circuitry which may be provided on a stimulator 14 and/or IPC 10 may use near field, far field, induction, magnetic resonant induction components, coils, antennae, and/or rectenae, optical sensors and stimulators, sonic stimulators and sensors, etc. to provide for successful communication of data or power signals between any external and internal components of a particular embodiment of the invention. The apparatus 50 also has a power supply module 74 which can include components such as a battery, AC and DC converters, circuitry related to the conversion or provision of power, and can provide a power cord for connecting to a wired power source through at least one of the communication/interface ports 82.

The communication module 68 can work in conjunction with the user interface module 76 which contains hardware and software for presenting information to a user (e.g. patient or physician) and obtaining information from the user. Although the device 50 may communicate with a physician or patient programmer 70,72, such as may be realized by a smartphone or tablet computer, the device 50 may also have at least one signaling module 78 with related circuitry and control a display 79 for presenting visual data and contain a speaker for presenting auditory signals (or the speaker can be a Bluetooth enabled sound system with an ear transducer that uses the communication module 82). The device 50 can also contain patient interface module 80 with controls such as nobs, switches, etc. to allow a user to provide input, such as through a menu guided system, as well as adjust operation of the device by manually adjusting nobs related to the operation of the device.

Both the control module and the waveform generator module may be configured with safety hardware and software routines, including calibration routines to calibrate the apparatus 50 and to ensure proper functioning. The control module allows stimulation programs to be implemented according to protocols stored in the device memory or according parameters that can be adjusted by a user's manual input obtained by the patient interface module 80.

The device 50 may use a first stimulator conduit 84, a second stimulator conduit 86, to communicate signals to a first stimulator 88 and second stimulator 90. In one embodiment, the conduits may comprise single or multi-stranded electrically conductive, insulated lead wires and the stimulators may be electrically conductive cutaneous electrodes. The first conduit 84 has a first end connector 92 that may contain a plug that electrically couples to a first stimulator interface port 83a of the input/output interface 82. The first stimulator 88 is preferably able to be secured to the second end connector 94 of the stimulator conduit 84 using a stimulator connector 89a. The stimulator connector 89a may be an adaptor such as a metallic snap that is configured to connect with the second end connector 94a.

The second conduit 86 also has a first end connector 92b and a second end connector 94b. The first end connector 92b of the second conduit 86 electrically couples to a second stimulator interface port 83b. The second stimulator 90 can be connected to the first end connector 94b of the second conduit 86 using an electrically conductive connector 89b.

Additional wire interface port 83c is shown (as well as additional ports not shown), and may allow additional stimulators to be used. Additionally, rather than stimulators, the interface ports 83 can be connected to sensors. Further, when the stimulators are cutaneous electrodes, then the electrode can serve as both stimulator and sensor at different moments in time. In other words a stimulation electrode 88 can serve as sensor when the sensing module rather than stimulation module is operational for a specific port during a period when sensing occurs.

The interface ports 83 may each be configured to connect to conduits having several independently operable wires, and the stimulator connectors 89 may be configured to receive such multiple inputs. For example, a conduit may be realized as a ribbon cable that terminates in an end connector 89 having multiple contacts and may also be plugged into an interface port 83 which is configured to operate multiple contacts simultaneously or sequentially. For example, rather than having a single conductive surface of one polarity, a stimulator may be realized as an bipolar electrode having a positive contact 96, and a negative contact 98, which may be separated by non-conductive surface 97. In a preferred embodiment the non-conductive surface would have a width that was the same width "W" as that of an IPC of the current invention. Further, as is known in the art, a stimulator can be configured as an electrode grid or array 100 having multiple contacts arranged in a grid or otherwise, each of which is connected to a unique contact of a connector 89 and conduit 84. Individual contacts on the grid may be used to electrically stimulate the patient using the multiplexing and control circuitry of the device 50 to provide for spatially different stimulation patterns. The electrode grid may also incorporate optical elements, such as LEDs, which can assist with visualizing a stimulation shape and aligning an active surface of the electrode grid with a desired area of skin 20 of a patient 8. The provision of a visual indication of the pattern of stimulation may only occur at the beginning of a treatment session when a user or medical technician is adjusting the shape of the waveform to be used during the subsequent provision of treatment or can also occur during treatment.

The width of the non-conductive surface 97 of the stimulator can be set to provide improved stimulation by the IPC. For example, the data of FIG. 3A to FIG. 8B, support a method of one embodiment of the invention, in which for Step 1 the width of the IPC that will be implanted should be set approximately according to the depth at which it will be implanted (i.e, the distance from the stimulator to the IPC). In step 2 a physical characteristic of at least one stimulator (e.g., the distance between two stimulators or two active plates of one stimulator, or the location of an edge of the stimulator) can then be set according to at least one physical dimension (e.g. width or location of an edge) of the IPC in order to provide for improved activation of the target nerve. In step 3, treatment is provided to the IPC using at least one stimulator.

Figure 18B:
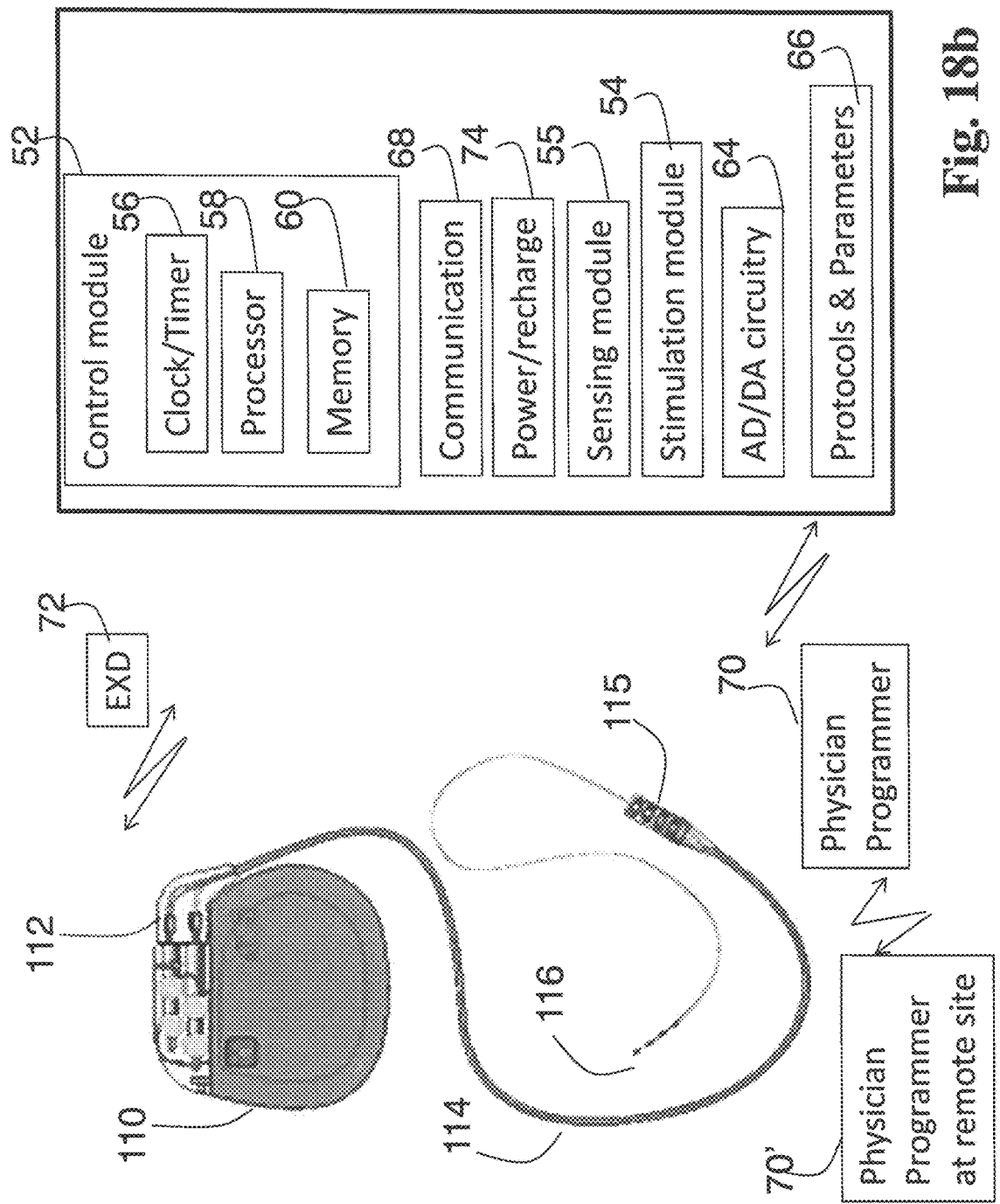
FIG. 18b is a schematic diagram of a tissue stimulation system including an implantable electrical stimulation system which may be used to realize the current invention.

The modules described for the apparatus 50 are for illustration purposes only and the device used by the system can be realized with less than or more than the modules of FIG. 18a or 18B. For example, rather than having a protocols and parameters module 66, the information related to stimulation protocols and parameters can be simply stored in the memory module 60. Similarly, rather than having a stimulation module 54, a waveform generator module 62, and an AD/DA module 64, equivalent functionality can be realized a stimulation module which contains these modules and all other necessary hardware and or software required to provide stimulation signals. In the device 50, some disclosed components may be omitted and the various modules may communicate with, and share, resources of other modules. Any of the modules of the device 50 shown in FIG. 18a, can be realized partially or fully in the physician/patient programmer 70 or EXD 72. The modules may be realized within a housing of the device 50 or some may exist outside the housing and communicate with wired or wireless manners.

The apparatus 50 may be realized as a portable or desktop instrument. Further the system can be implemented, at least in part, as customized hardware that plugs into a port of an smart-phone or tablet computer or which communicates with the smartphone or computer so that some of the modules shown in FIG. 18a are realized by the smart phone or computer.

Additionally, the system can use a set or subset of stimulators that are incorporated into the housing the device 50 itself rather than being connected to the device 50 by wires. In one example of this type of embodiment the stimulators can be configured as re-usable electrode stimulation plates rather than disposable electrodes. The apparatus 50 may also use percutaneous stimulators including needle electrodes. The apparatus 50 may be realized using electrical stimulators distributed by Uroplasty and Electrocore and Emkinetics for providing various types of stimulation including electrical and magnetic stimulation. Further, in alternative embodiments of the invention, the stimulators can be configured to work with IPCs or implantable active components (IACs) which are magnetically driven. Stimulators can be coils which induce magnetic fields in and around the implantable components and/or in the tissue itself.

The transcutaneous tissue stimulation system can contain a signal generator for generating a stimulation signal. The signal generator can provide a stimulation signal that is appropriate for at least one modality of stimulation such as electrical, magnetic, (ultra)sonic, optical, thermal, or other method of stimulating tissue directly, in combination with an IPC, or IAC. At least a first stimulator is also provided and is coupled to said signal generator. The first stimulator is adapted to be positioned adjacent to a patient to provide a signal to modulate target tissue in the patient. In an embodiment in which an IPC is used, at least a first IPC is located adjacent to or contiguous with a target tissue for enhancing the modulation of said target tissue by the signal provided by the stimulator. The stimulator and IPC can be paired so that modulation of tissue is enhanced relative to the modulation that occurs in the absence of the IPC.

In the case where the stimulator provides either transcutaneous magnetic or transcutaneous electrical stimulation, the IPC is configured with at least a portion that is electrically conductive. A device that is configured to provide magnetic stimulation to tissue, having a stimulator that is at least one stimulation coil, is disclosed in U.S. Pat. No. 8,052,591 entitled "trajectory-based deep-brain stereotactic transcranial magnetic stimulation", in US2013/0317281 entitled transcranial magnetic stimulation for improved analgesia", in U.S. Pat. No. 6,453,204 entitled "Magnetic electrode for delivering energy to the body", in U.S. Pat. No. 8,676,324 entitled "Electrical and magnetic stimulators used to treat migraine/sinus headache, rhinitis, sinusitis, rhinosinusitis, and comorbid disorders", in US2014/0247438 entitled "Systems and methods for vagal nerve stimulation", and in U.S. Pat. No. 8,435,166 entitled "Method and Apparatus for magnetic induction therapy", and may be realized as part of the system of the current invention. When at least one magnetic coil is used to provide a magnetic field, the signal generator of the signal generator module 62 may serve as an impulse generator capable of powering the at least one magnetic coil.

In the case where the stimulator provides ultrasonic stimulation, the IPC is configured with at least a portion that is responsive to the ultrasonic stimulation signal. For example, the IPC can be configured with a portion that has physical characteristics (size, density, shape, structure) that allow it to absorb or reflect, or resonate with the sound energy more than human tissue in order allow the IPC to vibrate and thereby modulate the activity of adjacent nerve tissue. A device that is configured to provide ultrasonic stimulation to tissue is disclosed in US20140194726 entitled "Ultrasound Neuromodulation for Cognitive Enhancement", in WO 2014127091 entitled "Transcranial ultrasound systems", in US20110270138 entitled "Ultrasound macro-pulse and micro-pulse shapes for neuromodulation", and in US20110190668 entitled "Ultrasound neuromodulation of the sphenopalatine ganglion", which uses at least one stimulator which is an ultrasound transducer coupled to a signal generator of the signal generator module 62, may be realized as part of the system of the current invention.

In the case where the stimulator provides optical stimulation, the IPC is configured with at least a portion that is responsive to the optical (e.g., laser) stimulation signal. For example, the IPC can be configured with a portion that has physical characteristics (size, shape, structure, reflectance, absorption) that allow it to absorb or reflect the optical energy more than human tissue in order allow the IPC to modulate the activity of adjacent nerve tissue. A device that is configured to provide optical stimulation to tissue is disclosed in U.S. Pat. No. 8,715,327 entitled "Baroreflex modulation using light-based stimulation", which uses stimulators which are light sources such as diodes, and may be realized as part of the system of the current invention.

When the IPC is used in conjunction with electric, magnetic, sonic, or light based stimulation, it may be realized as a nerve cuff, a solid rod, a hollow rod, a mesh structure, or other structure that allows the IPC to enhance the modality specific energy that is supplied by at least one transducer.

The methods and systems for providing enhanced transcutaneous electrical stimulation provided by the IPC, relative to what occurs without the IPC, is termed "eTENS". When the stimulator and paired IPC utilize ultrasonic tissue stimulation this is known as termed "eUltrasound", the modality is light it is termed "eLaser", and when the modality is magnetic fields that are applied to tissue targets, which may or not also require transmission of the magnetic field through the cranium, it is known as "eTMS".

A method of providing transcutaneous nerve tissue stimulation can comprise operating at least one signal generator of the signal generator module 62 for generating at least one stimulation signal and operating at least a first stimulator coupled to said electrical generator of the signal generator module 62, and positioning the stimulator adjacent to a patient to provide a signal to modulate a tissue target in the patient, and implanting an IPC adjacent to or contiguous with a target tissue for enhancing the modulation of said target tissue by the signal provided by the stimulator. In this manner, the stimulation signal provided by an electric, magnetic, optical, or ultrasonic transducer may cause the modulation of tissue to be enhanced relative to the modulation that occurs in the absence of the IPC.

In overall concept there is a method of providing treatment of a patient's pelvic floor disorder which includes the establishment of a neurostimulator which is configured to provide one or more stimulation signals to one or more stimulators positioned external to the patient and preferably on the skin surface of the patient. A shaping element is coupled to the one or more stimulators by direct or indirect coupling. The field shaping element adjusts the shape of at least one stimulation field of the stimulation signal or stimulation signals to target stimulation of a nerve. The neurostimulator is then activated to provide a shaped stimulation to the nerve in a lower limb of the patient with the shaped signal having a stimulus characteristic configured to treat the pelvic disorder.

FIG. 34*a* shows a lower surface of an embodiment of a stimulation grid 100' which makes contact with the patient's skin and comprises an electrode array arranged in a first column of stimulators 528*a*-528*e*, second column of stimulators 529*a*-529*e*, and third column of stimulators 530*a*-

530*e*, each having 5 rows of stimulators. Alternatively, a grid 100' may be comprised of as little as 3 stimulators which allows for at least 3 different patterns of stimulation to occur. The stimulation grid serves as a field shaping element of the system which can change characteristics of the field such as field shape and the current density. Each stimulator of the grid has a non-conductive surface 97' and a conductive surface which serves as an electrode 88', although this is only shown labeled for stimulator 528*a* to avoid cluttering of the figure. Rather than being arranged in rows the stimulators may also be arranged in a non-regular geometric pattern and may have different spacings between the electrodes and further the stimulators can each be of a different shape and size. The stimulators of the stimulation grid 100' are formed within or attached to a non-conductive material (e.g., vinyl, foam, rubber, silicone-materials, polymers, neoprene, polyethylene naphthalate, co-polymer plastics) which may be laminated and can have an adhesive film on its lower surface to allow the grid to be stuck to the patient's skin. Accordingly, the conductive elements are each separated from the other by electrically non-conductive surfaces. FIG. 34*b* shows the upper surface of the stimulation grid 100', which has a electrical connection for providing one or more one stimulation signals using a multi-stranded conduit 85, which provides conduits 85*a*-85*e* to the stimulators of the first column 528*a*-528*e*. Conduits 85*a*-85*e* connect to the conductive surface 88' of each stimulator 528 and also provide conduits which power an optical element 95*a* (e.g. LED) which serves as an indicator that the corresponding stimulator below it is active. In the figure optical elements 95*b*-95*e* are not shown for each of the stimulators 528*b*-528*e*, and the elements labeled in the figure for the first column of stimulators are also not illustrated for the $2^{nd}$ and $3^{rd}$ columns of stimulators to avoid cluttering of the figure. In an embodiment, each set of two stimulators (e.g. 528*a* and 528*e* or 529*a* and 529*e*) may provide a single stimulation channel having both an anode and cathode which are connected of a stimulus generator. Alternatively, two stimulators serve as a single channel and are connected to the same generator (e.g., 528*a* and 529*a* serving as anode and 528*e* and 529*e* serving as cathode). Further, a single stimulator (e.g. 528*a*) may have two stimulators (528*e*, 529*e*) which serve to provide the return path of the stimulation signal.

In an embodiment, the conduit 85 is connected on its proximal side to an interface port 83*c* of the input/output interface 82 which provides selectable powering of the stimulators and optical elements of the grid 100'. In an embodiment the device 50 also adjusts the brightness optical element 95 in proportion to the strength of the stimulation signal that is provided by the corresponding stimulator 528*a*. Further, color schemes may be implemented, such as if the stimulator is used by the device 50 as an anode then the diode is one color (e.g., red) while an anode is a different color (e.g. white).

In embodiments, a method for shaping a field includes operating a field shaping element configured for adjusting the shape of the stimulation field and the field shaping element includes a shaping electrode grid 100'. The grid contains at least three grid elements having fixed positions (which can be a subset of any of stimulators 528, 529, 530), and at least two are selectively activated to provide at least two different stimulation patterns. The stimulator is realized as one of the grid elements or may be separate from the grid and operated in collaboration with the stimulator. All three grid elements can be provided upon a non-conductive flexible backing to provide a fixed geometry of stimulation. A field shaping element can be configured for adjusting the shape of the stimulation field of at least one stimulator using a plurality of at least two additional electrode stimulators, and field shaping includes defining a set of at least two stimulators to be selectively activated to provide a stimulation pattern as part of the stimulation protocol stored in the memory of a neurostimulator or as selectively adjusted by a user at the time of treatment.

In an embodiment, a field shaping element is configured for adjusting the shape of the stimulation field of a stimulator using a shaping electrode grid that has least three grid elements, and at least two sets of grid elements are selectively activated during treatment to provide at least two patterns of stimulation and optical indicators provides a visual indication corresponding to the shape of the stimulation field. In an embodiment "activated" indicates the stimulator is configured to supply at least a portion of an electrical stimulation signal. For example, a first stimulator acts as the active electrode and one of the two remaining electrodes serves as the complementary electrodes of the circuit. Alternatively, electrode stimulators 2 and 3 can both serve as the complementary electrode for the same active electrode. The shaping electrode grid may be divided into a plurality of electrically conductive elements each of which is selectively and programmatically attached to at least one output connector of a signal generator during operation to shape the field that is provided to a patient. For example, a set of shaping parameter values are defined for the at least 3 grid elements of an electrode grid, and these are stored in memory of a stimulation device 50, and retrieved as part of the stimulation protocol to provide a selected stimulation field shape during treatment. When an electrode grid is used with an IPC, then a set of conductive contacts can be selectively activated to cause alignment between an edge formed by the selectively activated electrically conductive elements and a portion (e.g. edge) of the IPC. As shown in FIG. 18*b* the apparatus that provides the electrical stimulation to tissue near the IPC may be realized by an implanted device 110 such as a deep brain stimulation device or spinal implant device. The implanted device 110 has all the electronics normally provided in a modern implantable stimulator including components to provide for control 52, stimulation 54, communication 68, timing 56, and power supply 74. Sensing capacity may also be provided via a sensing module 55. The implanted device 110 will have ports 112 for securely connecting to an electrical conduit 114 (which may have an intervening connection member 115 to connect various types of implantable electrode conduits) and for communicating pulse waveforms along the length of the conduit to at least one stimulator 116 such as stimulation electrode which contains at least one contact, but often multiple contacts, to enable bipolar stimulation to occur. In FIG. 18*b* there are multiple contacts at the distal tip of the conduit 114. In an embodiment of the invention where at least one IPC is used with the implanted device 110, the IPC would preferably have a length that was set proportionally to the inter-contact distance between two of the contacts of the stimulation electrode 116, and preferentially this the IPC length would be the same as the inter-contact distance. Further it would be preferable for the edge of at least one IPC to be aligned with the edge of one of the stimulation contacts, at least in the case of bipolar stimulation. In the case of monopolar stimulation (e.g., tip to can) the electrode contact may be made to be longer than the length of the IPC.

The implanted deep brain stimulation device or spinal implant device may be any approved device on the market, such as the Restore™ Neurostimulator, which can adjust the stimulation in the treatment of chronic pain based upon factors including a patient's posture (e.g. sitting to lying down, from lying down to standing up). The apparatus may be realized by a device such as the InterStim0 System for Sacral Neuromodulation, the ReclaimTM deep brain stimulation system for treating obsessive compulsive disorder, the Neuropace system for providing responsive neurostimulation to the brain in the treatment of epilepsy, or vagal nerve stimulation systems provided by Cyberonics for the treatment of, for example, epilepsy and depression.

Figure 19:
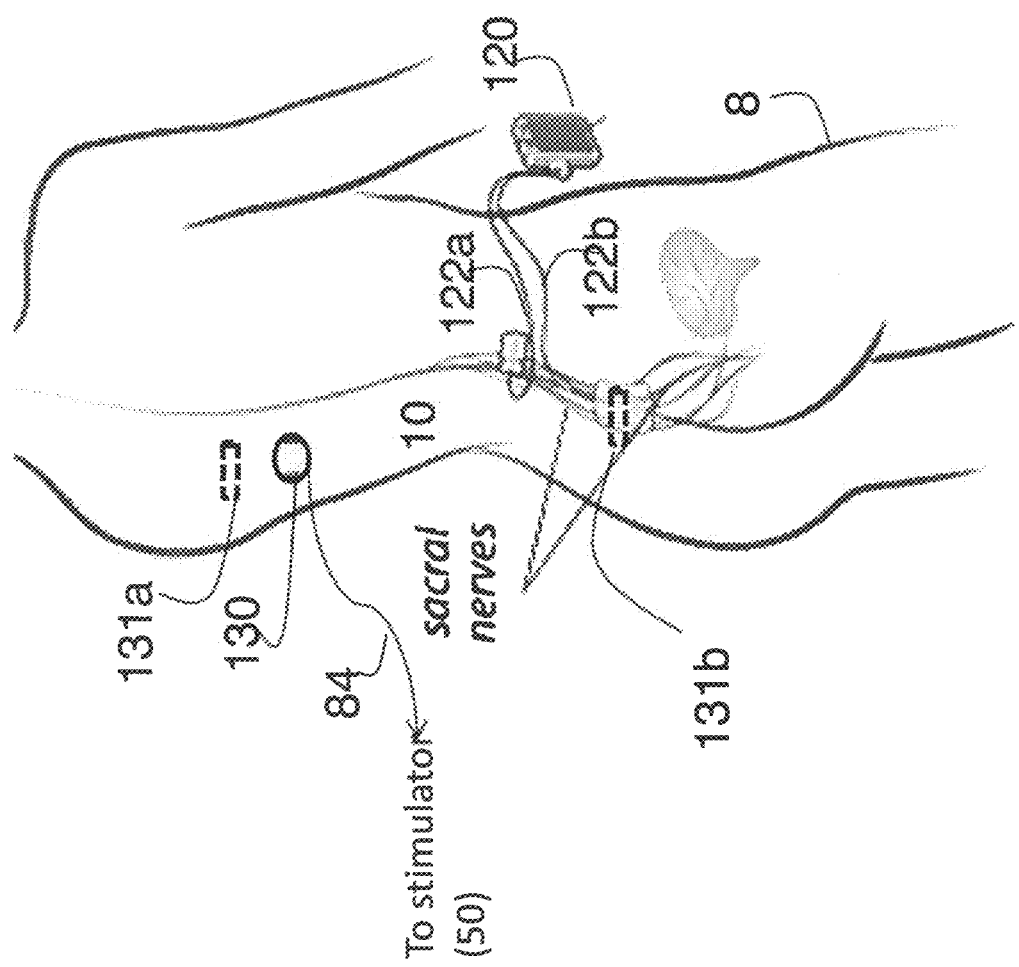
FIG. 19 is a schematic diagram of an alternative nerve stimulation system which may be used with transcutaneous stimulation and transcutaneous connections to realize the current invention.

FIG. 19 shows a schematic of an external electrical nerve stimulator 120 which may be used with either cutaneous or percutaneous connections to realize the current invention. For example, the stimulator can provide for percutaneous stimulation to electrodes 122a, 122b to stimulate the nerves (e.g. sacral) of a patient. The stimulator can also be used with cutaneous electrodes placed superficial to one or more IPCs implanted on or near the sacral nerves of a patient. The IPC of the current invention may be placed near the stimulation electrode contacts and may be of a selected shape, orientation, and distance from the stimulation electrodes, according to the principles and innovative models of the current invention, so that target nerves may be stimulated while minimizing or preventing the activation of nearby nerves which are not targets of the stimulation.

A method and system of differentially activating one or more subsets of neural pathways can provide the advantages of (1) improving modulation of a selected therapeutic outcome, (2) decreasing at least one stimulation-evoked side effect, (3) providing concomitant, but unique, stimulation related to each of a plurality of IPCs in order to provide for selective modulation of physiological responses associated with specific somatic or autonomic nerves, such as areas along these nerves (4) providing concomitant, but unique, stimulation to inhibit one or more physiological responses associated with somatic or autonomic nerves where IPCs have been implanted, (5) providing a mixture of stimulation which serves to both activate and inhibit different physiological responses (direct or reflexive) associated with either somatic or autonomic nerves or both, and (6) provide for improved selective modulation of specific motor responses and response pathways. In one embodiment, selective nerve activation is achieved by managing the relationship between the physical dimensions (e.g., physical dimensions such as length) of one or more IPCs to approximate those dimensions of one or more corresponding stimulators. This relationship can follow principles derived using, for example, the results of FIG. 4 to FIG. 8.

Figure 20A:
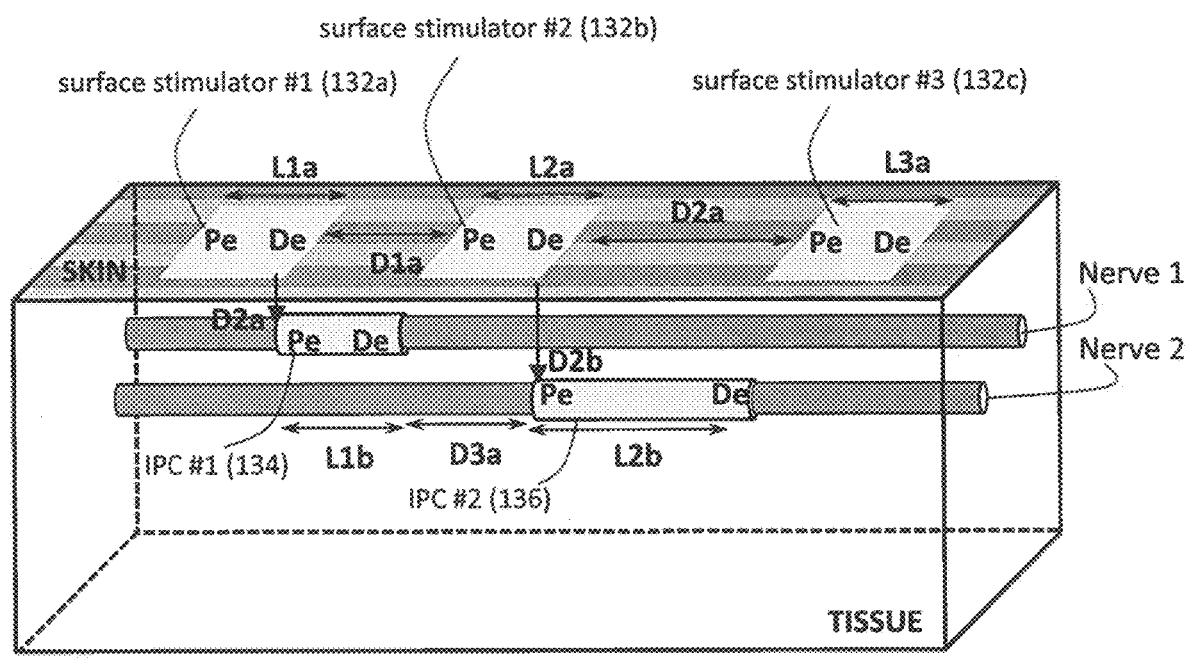
FIG. 20a is a schematic diagram of an embodiment of a system for selective (eTENS-based) activation of multiple nerves using a bipolar stimulation paradigm.

FIG. 20A shows embodiments of a system configured selective activation of multiple neural targets (labeled Nerve 1 and Nerve 2). The system (or a model representing the system) can be comprised of two or more IPCs placed in close proximity to, or around, nervous tissue targets to assist in providing selective activation of a single or plurality of nerves (or nerve branches) located within the body (e.g., muscle, connective, and fat tissue). This strategy can be implemented by using bipolar electrodes, where the IPC lengths (L1b, L2b) are approximated by the distance between the surface stimulating electrodes (D1a, D2a). All electrodes and IPCs are positioned along the length of the nerve in relation to proximal end (Pe) and distal end (De) of each system component. The depths of the IPCs from the skin surface (D2a, D2b) may be varied. The system can enable the activation of a single nerve bundle using a given set of stimulation parameters (e.g., particular amplitude, frequency, pulse width, bursting pattern, duration, waveform, and duty cycle), or modulate two or more different neural pathways with different sets of stimulation parameters. Surface stimulators 1, 2 and 3 can be independently operated, or stimulator 2 can be a common return for stimulator 1 and 3.

Figure 20B:
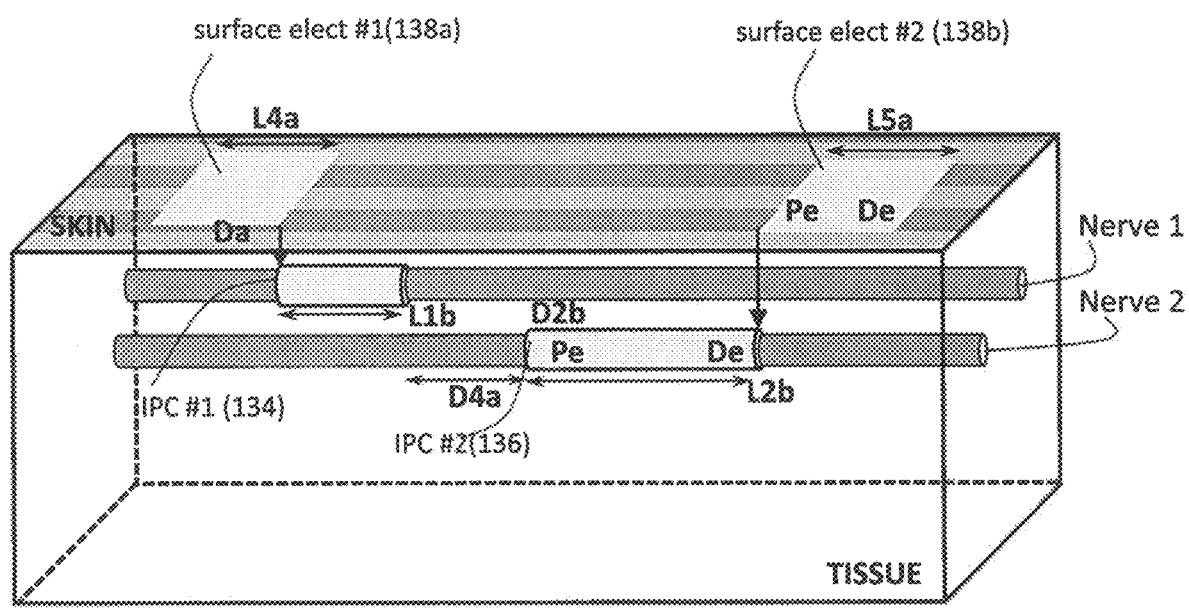
FIG. 20b is a schematic diagram of an embodiment of a system for selective (eTENS-based) activation of multiple nerves using a monopolar stimulation paradigm.

FIG. 20B shows another embodiment of selective nerve activation by eTNS through the use of monopolar stimulating surface electrodes 138a 138b. The physical dimensions of each IPC 134,136 and the corresponding "paired" electrode (138a and 138b, respectively) are selected to match in order to provide selective eTNS (i.e., improved neural excitability of independent neural targets). In this case, the lengths of the two passive IPCs 134, 136 (realized as nerve cuff form factor placed around nerves 1 and 2) are L1b and L2b, respectively. Selective activation of each individual nerve 1 and 2 (via enhanced neural excitation) is achieved by applying electrical pulses (transcutaneously) through surface electrodes 1 and 2, where selective enhancement is achieved by matching the edges of the IPC +stimulator pair. The length of the stimulator may be smaller or equal or greater than that of the IPCA stimulator-IPC pair can be matched so that the pair operate to provide enhanced stimulation according to the principles of the current invention. The stimulation parameters delivered through each surface electrode will, in turn, primarily result in the corresponding generation of action potentials in each respective nerve. In an example monopolar embodiment, at least the proximal edge ("Pe") distal edge ("De") of the IPCs are preferably aligned with the corresponding edges of the surface electrodes. Correspondence, in the lengths of the stimulator and IPC "pair" a well as the alignment of the edges of the IPC and surface electrode, can be an important factor for achieving selective activation of individual nerves in certain monopolar and bipolar embodiments. Improved enhancement of TENS is achieved by aligning the edges of each IPC and surface electrode (refer to FIG. 6).Although in the figure L1a and L1b appear about the same length, L1a may be larger or smaller than L1b (i.e., stimulator length may be >or <compared to IPC length)

In another embodiment, selective nerve activation is achieved using a system of multiple IPCs in which only one edge of the IPC is aligned with the proximal edge or distal edge of the stimulating surface electrode. All the physical parameters of the stimulation system can be stimulated using the models disclosed in this invention in order to determine improved implementations within individual patients.

Figure 21:
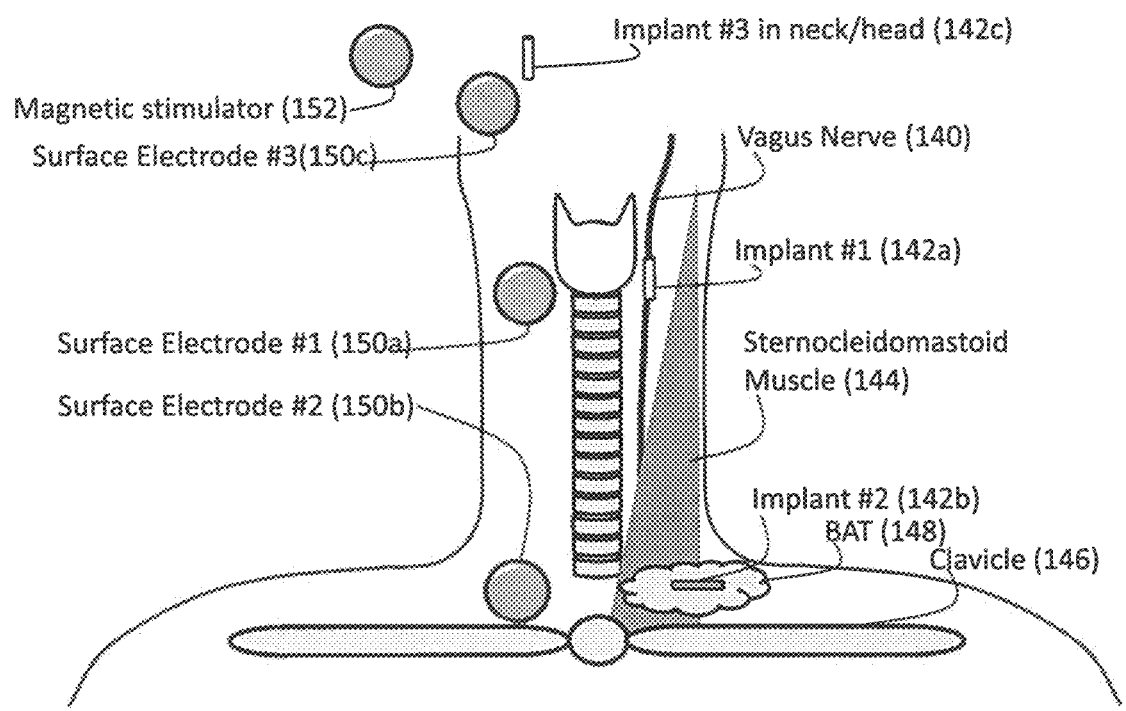
FIG. 21 is a schematic diagram of the enhanced transcutaneous nerve stimulation (eTNS) system for electrically activating nervous tissue at sites in the neck and upper chest which are relevant to modulating nerves that reside in these areas.

FIG. 21 shows a schematic of the system for electrically activating nerves of the head, neck and upper chest, such as those of the autonomic nervous system. For example, the system may be implemented for stimulating the vagus nerve 140 for treating epilepsy, depression, or respiratory disorders using IPC #1 142a. Additionally, or alternatively, a second IPC 142b may be implanted to activate sympathetic nerves within brown adipose tissue or "BAT" 148 (e.g., at a supraclavicular location) to treat obesity. Surface electrodes 1 150a and 2 150b are illustrated contralateral to the corresponding implanted IPCs in order to avoid cluttering of the figure, but would typically be located ipsilateral and appropriately aligned with the IPCs.

In this example, selective activation of either the vagus nerve 140 or nervous tissue within the BAT 148 can be achieved by stimulating electrode 1 150a or electrode 2 150b, respectively. In a monopolar configuration the return surface electrode (anode or cathode) for either electrode 1 or electrode 2 can be placed on an anatomically appropriate location. Such a candidate site is one where electrical stimulation causes minimal physiological or sensory activity at the return electrode site. An appropriate candidate location for the return electrode may include the upper or lateral hip area. Alternatively, electrical stimulation can be delivered in a bipolar fashion, where each surface electrode is bipolar (with 2 contacts of opposite polarity) and are preferably placed such that at least one edge of each electrode is aligned with one of the two edges of each IPC (analogous to the alignment of IPC #2 with stimulator #2 in FIG. 20A).

Using the systems illustrated in FIG. 21, a method of BAT stimulation may comprise placing a pair of surface electrodes laterally, with respect to the position of the IPC, whereas vagus nerve stimulation could comprise the placement of a pair of surface electrodes both rostral and caudal to the IPC. In another embodiment, two IPCs can be surgically positioned bilaterally (e.g., to stimulate left and right cervical vagus nerves). Activation of vagus nerve, or the autonomic nerves located within the BAT, can be achieved in a monopolar fashion as in the case where one surface electrode is placed over the left IPC and the second (i.e., return) electrode is placed over the contralateral IPC. Each pair of surface electrodes serves as the positive (i.e., anode) and negative (i.e., cathode) stimulators. Each electrode can be positioned on a non-conductive foam pad, and each contact can be connected to an electrical source of the respective polarity.

In an alternative embodiment, the IPC #3 142c may be placed in the upper throat or locations in the head, face, or ears to treat disorder such as obstructive sleep apnea and headache as will be disclosed. Additionally, a magnetic stimulator 152 may induce a field in tissue near the IPC which, in conjunction with the IPC, allows for selective activation of a tissue target.

Active and Distributed Embodiments

In one embodiment the principles of the current invention, can be used to configure and improve a stimulation router system (SRS), such as that described in U.S. Pat. No. 8,332,029 entitled "Implant system and method using implanted passive conductors for routing electrical current" to Glukhovsky, which is assigned to Bioness Inc. For example, the "pick-up electrode" of the SRS may be configured for receiving a field provided by at least one selected stimulator in a manner according to the current invention. For example, the SRS may have a component that has physical dimensions and alignment with at least one external stimulator according to the principles of the current invention.

In an alternative embodiment of the invention, the IAC can be configured as part of an implanted stimulator that obtains its power from a magnetic stimulator and is provided with circuitry to convert the magnetic to electrical energy (even though the magnetic stimulator 152 and IPC #3 142c of FIG. 21 uses a passive IPC, an alternative embodiment may use a stimulator 152' that is configured to work with an IAC having active components 142c'. Either system design may be relevant to methods such as that illustrated in FIG. 22b which, in one embodiment, uses an IPC for a selected duration in order to determine if a (typically larger) device should subsequently be chronically implanted in the patient, such as an implantable chronic vagal nerve stimulator. For example, a portion of the systems and methods of the current invention, such as those related to screening, can be realized using a system akin to the magnetically powered neurostimulator disclosed in US App. 20130310895 entitled "Neurostimulator system apparatus and method" or the magnetically powered neurostimulator disclosed in US App. 20120101326 to Simon et al, entitled "Non-invasive electrical and magnetic nerve stimulators used to treat overactive bladder and urinary incontinence".

The generation of electric fields that are designed to penetrate intervening tissue may be provided by surface (or implanted) stimulators which may also be configured to generate an electric field with field lines extending generally in the longitudinal direction of one or more nerves to be modulated. In some embodiments, the stimulators may be spaced apart from one another along the longitudinal direction of a tissue target such as a nerve to facilitate generation of such an electric field. The electric field may also be configured to extend in a direction substantially parallel to a longitudinal direction of at least some portion of the tissue or nerve to be modulated. For example, a substantially parallel field may include field lines that extend more in a longitudinal direction than a transverse direction compared to a nerve. Orienting the electric field in this way may facilitate electrical current flow through a nerve or tissue, thereby increasing the likelihood of eliciting an action potential to induce modulation. Accordingly, the orientation of at least one IPC may also be oriented along the length of a nerve in order to remain effectively paired with at least one stimulator to provide for enhanced stimulation of the nerve.

Tissue Modulation for Screening and Treatment.

In one embodiment an IPC 10 may be configured for implantation in a subject in a location that permits the modulation of target tissue which is a nerve 12 situated such that intervening tissue exists between the IPC 10 and the nerve 12. Intervening tissue may include muscle tissue, connective tissue, organ tissue, or any other type of biological tissue. The location of IPC 10 does not require contact with nerve 12 for achieving effective neuromodulation. However, placement of the IPC 10 located directly adjacent to nerve 12 is preferred for effective neuromodulation, such that no intervening tissue exists. During an implantation procedure different locations can be tested for the IPC 10, and different amounts of stimulation can be provided to the IPC 10 in order to assess various aspects such as suitability of various stimulation protocols, implant sites, response to stimulation, or effectiveness of therapy. Additionally, different candidate locations for the stimulator may also be assessed. The IPC and stimulator "pair" can be sequentially tested and adjusted (e.g., moved,) until a suitable location is found which will provide sufficient stimulation of a tissue target such as a location which has been shown to achieve a therapeutic result. Additionally different sizes, shapes, and numbers of IPCs and stimulators may be assessed during the implantation procedure.

A stimulator 14 can be configured to be used at a location external to a patient 8, either directly contacting, or close to the skin 20 of the patient (e.g. if the stimulator provides a magnetic field to issue close to the IPC, or to the IPC itself, then the stimulator does not have to reside upon the skin itself). The stimulator 14 may be configured to be affixed to the patient, for example, by adhering to the skin 20 of the patient via adhesive, or may use a band or other securing mechanism that serves to hold stimulator 14 in place. The stimulator 14 should be placed so that it is paired with the IPC by being suitably positioned, oriented, angled, and/or configured with physical dimensions so that the IPC effectively provides enhanced modulation as intended. The physical dimensions of at least one IPC and at least one stimulator may be adjusted or selected according to the approximate distance that will exist between these two system components during stimulation of a subject.

In different embodiments, the suitability of locations for both the stimulator and the IPC may be determined according to various methods and components which are disclosed. For example, when the IPC contains communication circuitry, suitable placement of the stimulator may be confirmed by communication between the stimulator and the IPC. Although oriented towards magnetic inductive stimulation, methods and systems for allowing external stimulators and implanted components to communicate (in order to indicate suitable placement of the stimulator relative to the implanted components) are relevant, for example, in US App #20130079843, to Mashiach, entitled "Apparatus and methods for feedback-based nerve modulation." In one embodiment, a processor 58 of the stimulation device 50 may be configured to automatically determine the baseline physical range between a stimulator 14 and IPC 10. For example, a signal can be supplied when the processor 58 detects that a primary antenna (or coil) of the stimulator 14 and secondary antenna (or coil) of the IPC 10 are within range of each other. In such an embodiment, when processor 58 detects a sufficient degree of coupling between a primary and secondary antenna, then the processor 58 may monitor the coupling range and provide a signal that indicates when the coupling remains within an acceptable range.

Screening

As a screening method there are several advantages which eTNS has over using percutaneous stimulation (PNS). Once the IPC is implanted, its effect can remain very constant with respect to increasing the activating function of a particular portion of nerve proximate to the IPC. In the case of PNS, the needle must be inserted and correctly positioned within the subcutaneous space at the beginning of each stimulation session. The eTNS can allow a screening period to occur at home and/or in the clinic because the patient does not need to undergo repeated piercing of the skin. Accordingly, the eTNS allows patients to undergo screening/treatment procedures which may involve nerve stimulation several times during the day, or which occur daily over a several month period, all of which would be very difficult to implement if clinical visits were needed. Further, if the screening method uses a stimulator that is affixed to the person's skin in order to stimulate the patient during normal daily-life activities, perhaps for several hours each day, then the eTNS approach provides significant advantage over PNS and various other alternative approaches since it can occur for long periods of time without inconveniencing the patient. Further, since implantation of a very expensive, chronically implanted neural stimulator (with battery) is considered pretty invasive, the quick and easy implantation of an IPC may be desired by many patients and doctors in order to determine proper therapy course. This may be especially true when the IPC is embodied as a simple, inexpensive, conductive cylinder cuff, The eTNS also offers advantages over devices which require a temporary wire to be situated transcutaneously since the IPC approach can deter the chance of infection due to skin opening. When used with screening, the IPC may be configured as a nerve stimulator electrode that can be connected to an implanted device in the case where treatment course subsequently determines that a fully implantable and chronic stimulator is warranted.

Two different IPCs can be used in either screening or treatment therapy. FIG. 22A illustrates a method of implanting a first 200 and a second 202 IPC of lengths L1 and L2, and then situating at least a first and second stimulator 204 so that it is possible to stimulate a first IPC and second IPC, respectively. After the components are paired, treatment can be provided by the two paired stimulator-IPC pairs 206.

FIG. 22B illustrates a method of using enhanced transcutaneous nerve stimulation (eTNS) as a method of screening treatment candidates (patients) who might benefit from various types and modes of neuromodulation therapy (e.g., fully implanted systems). In one embodiment, the method comprises the step of implanting, within the patient, at least one conductive implant proximal to an anatomical target of the patient 210. The target is selected as a candidate therapy target which will be assessed during the steps of the method. The next step 212 is to provide at least one stimulation signal to the patient from a stimulator located outside of the patient according to a screening protocol. There is also step of assessing the patient response to the provision of the stimulation signal provided in accordance with the screening protocol to produce a screening result 214. The screening result can be calculated from a comparison of data before and after stimulation, or may include an assessment of data from before, during, and/or after the stimulation takes place. The screening result can be calculated on data from a single stimulation session or from multiple stimulation sessions during which either the same or different stimulation parameters were used. In the screening method, if the screening result is positive then at least one positive screening outcome activity is performed 216. Alternatively, if the screening result is negative then then performing at least one negative screening outcome activity 218. Positive results may be obtained when screening results are compared to at least one screening criterion and the data are able to successfully pass at least one screening criterion. Negative results may be obtained when screening results fail at least one screening criterion. Examples of positive and negative screening outcomes are now provided.

The method may include, for example, a positive screening outcome activity 216 which includes implanting a fully implantable stimulation system in the case where the patient met at least one screening criterion. The positive screening outcome indicates that a fully implantable system is indicated, since the result of a patient positively responding to the transcutaneous and/or eTNS stimulation is interpreted to mean that the patient is a good candidate for a fully implantable, or relatively more invasive, stimulation system.

An alternative positive screening outcome activity 216 is to not implant a relatively more invasive, stimulation system. In this case, the fact that a patient met at least one screening criterion is interpreted as indicating that the patient does not require the implantation of a fully implantable, or relatively more invasive, stimulation system. Accordingly, depending upon the intention of the screening test, a positive result may indicate either that a fully implantable system is warranted or that a transcutaneous or eTNS system is sufficient.

Additionally, the clinical determination of the appropriate intervention for a patient may include a series of screening tests. Initially, standard TNS is tested and based upon the results of that test, an eTNS may then be provided, and based upon the eTNS testing, the either the eTNS may be selected, a fully implanted system may be used, or no system may be implanted (since the patient did not respond to either TNS or eTNS). Further, if both TNS and eTNS fail to result in a patient meeting at least one screening criterion then a different mode of therapy may be warranted, such as implanting a brain stimulation system since vagal stimulation did not produce sufficient changes.

The method may include, for example, a negative screening outcome activity 218 which includes implanting a fully implantable stimulation system in the case where the patient failed to respond to the screening protocol. In this case, screening is negative by failing to meet at least one screening criterion. A negative screening outcome may result in the patient being provided with a different type of therapy, may indicate that drug therapy should be simultaneously provide, may indicate that an IPC location should be changed and the screening protocol redone, may indicated that the screening parameters should be adjusted before the screening test is tried again, or may indicate alternative treatment paths.

In one embodiment, a negative screening outcome activity 218 includes classifying the patient as a non-responder and seeking another modality of treatment. Alternatively, a negative screening outcome activity includes changing the stimulation protocol and repeating the screening regimen. The change in the stimulation protocol 220 may include a change in stimulation site where the implant is located. In the case that more than one IPC was implanted changing the stimulation protocol may simply entail changing the location of the external stimulator in order to stimulate a different IPC or in order to stimulate a different set of IPCs. The change in the stimulation protocol may include a change in stimulation site where the external stimulator is located. Alternatively, the change in the stimulation protocol may include a change in stimulation signal used to provide the stimulation including at least one of the following stimulation parameters stimulation strength, frequency, inter-stimulus interval, duration of stimulation, number of treatment stimulations provided within a day, week, or monthly period.

The results of the screening tests may, of course, be interpreted in terms of the larger clinical picture of the patient and information such as history of response to pharmaceuticals, the patients age, symptoms, preferences, and issues related to comfort may all play a role in determining how the results of the screening test are interpreted. There may be several screening criterion used in a screening test, and these may be interpreted in combination. For example, a first screening criterion may be smaller than a second screening criterion. A patient may pass a first screening criterion, indicating that the patient is responsive to, for example, vagal nerve stimulation, but may fail to pass a second screening criterion suggesting that an implanted system rather than a TNS system is required, or that an eTNS rather than TNS system is required.

The screening test may be useful as a measure which serves as an inclusion criterion in a clinical trial. For example, only patients who respond to an eTNS therapy may be considered candidates for a permanently, and fully implanted vagal nerve stimulator. In this manner, a clinical study for a permanent vagal nerve stimulator will not include patients who have failed to show a response to eTNS and thereby the trial may be able to show a larger treatment effect.

The external stimulator used in the screening may be at least one electrode which is temporarily attached to the patient, or may be at least one magnetic stimulator located outside of the patient. The magnetic stimulator may be configured to provide stimulation either directly to tissue, or to operate in conjunction with an IPC that is configured to receive magnetic energy.

In one embodiment, a method of screening patient or eTNS, can comprise the steps of providing at least one stimulation signal 212 to the patient from a stimulator located outside of the patient according to a screening regimen, assessing the patient response 214 to the provision of the stimulation signal provided in accordance with the screening regimen to produce a screening result; and assessing the screening result 214 as positive or negative. In the case where the screening result is positive 216 then the method includes performing at least one positive screening outcome activity, while if the screening result is negative then the method includes performing at least one negative screening outcome activity 218. In the case of a negative results, the method includes implanting, within the patient, at least one IPC proximal to an anatomical target of the patient, the target being selected as a candidate therapy target and configuring the stimulator to provide stimulation to the implant. The stimulator used during the screening procedure can be a transcutaneous electrical stimulator or a transcutaneous magnetic stimulator. In the case of a brain disorder, the stimulator can be a transcranial magnetic stimulator. The at least one implant comprises at least one passive IPC having at least one electrical conductive surface. In one example, the treatment may be sought, for a patient with a cortical pathology, the IPC can be located within tissue that is at least 2 inches from the surface of the cortex, and the stimulator may be a magnetic stimulator designed to provide stimulation to a patient's cortex.

Regardless of the screening test which is performed, the test results can be computed upon a patients subjective assessment of symptoms or upon evaluation of measured data such as physiological data including electrical brain activity, cardiac activity, blood pressure, a measure of the eye such as pupil dilation, HR, or other features which may be used to assess the patient as has been disclosed herein. When the test results are computed upon measured data, sensing 55 and processing 58 modules may provide for the data collection and assessment.

Implantable Component Designs.

A number of illustrative IPC designs are shown in FIG. 28 to FIG. 31 of this application. Some IAC designs, such as that seen in FIG. 33 can be powered by a device that uses magnetic or RF means to power the IAC of the stimulation system, as is disclosed in US 20130085545, entitled "Electrode Configuration for Implantable Modulator" and US 20130079843 entitled 'Apparatus and methods for feedback-based nerve modulation', both to Mashiach Although, unlike various embodiments of the IPC of the current invention, the Mashiach technology relies upon conversion of electromagnetic signals for all of the embodiments of his invention, some of the principles for the electrode design disclosed by Mashiach are relevant to the systems and methods of the current invention both for implementations that use electromagnetic signals and for those that simply use electrical signals provided from an external stimulator in the eTENS embodiments.

The IPC 10 may include one or more structural elements to facilitate implantation, orientation, and securing of the IPC 10 into the tissue of a patient 8. The securing element(s) 518 may include, for example, elongated arms, flaps, suture holes, surgical mesh, biological glue, hooks or spikes of flexible carrier which serve to anchor the IPC to tissue. The elements can facilitate alignment of the IPC 10 in a desired orientation within the patient and can provide attachment points for securing the IPC 10. In an embodiment, IPC 10 may include an elongated arm 540 having a first extension 542a and, optionally, a second extension 542b. The Extensions 542a and 542b may aid in orienting IPC 10 with respect to a target. Extensions 542 may be configured to enable the IPC to conform at least partially around soft or hard tissue (e.g., nerve, bone, or muscle, etc.) beneath a patient's skin. The IPC 10 may be constructed in various shapes, and can have additional or different structures in different orientations. The IPC 10 may be formed with a generally triangular, circular, or rectangular shape, or a shape that is determined based upon a particular target in patient (and can be designed based upon imaging data or measurements of a particular patient). In some embodiments, the shape, size, orientation, and characteristics of the IPC can be adjusted and selected to facilitate orientation of the IPC 10 with respect to factors such as a particular tissue to be modulated, the shape of the stimulator, and the distance between the stimulator and IPC.

Figure 33:
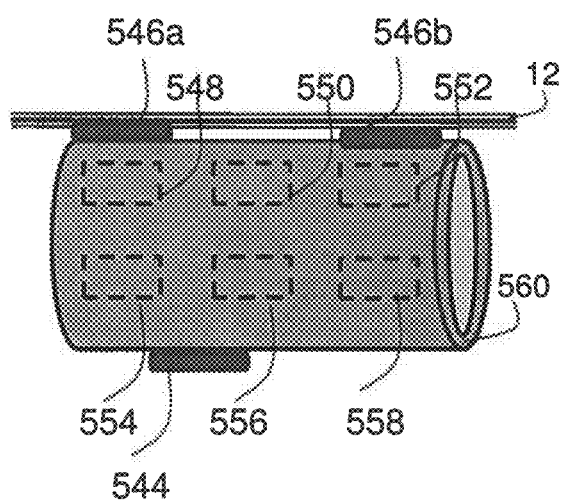
FIG. 33 is a schematic view of an embodiment of an implantable component for use with an external stimulator.

FIG. 33 shows components such as an antenna and/or coil 544, electrodes 546*a*, 546*b*, and circuitry related to power conversion 548, communication 550, safety 552, ID such as an RFID chip 554, memory for storing protocols and information 556, and control 558 may be mounted on, attached to, or integrated into the implantable active component (IAC), and contained within the IAC housing 560, when housing is provided. Various circuit components and connecting wires may be used to connect circuitry to the IAC electrodes 546. To protect various IAC components from the environment within a patient's body, the IAC and its components may include a protective coating. In some embodiments, the protective coating may be made from a flexible material to enable bending of components such as the electrodes. The encapsulation material of the protective coating may also resist humidity penetration. In some embodiments, the protective coating may include silicone, polyimides, phenyltrimethoxysilane (PTMS), polymethyl methacrylate (PMMA), Parylene C, liquid polyimide, laminated polyimide, polyimide, Kapton, black epoxy, polyether ketone (PEEK), Liquid Crystal Polymer (LCP), or any other suitable biocompatible coating. In some embodiments, the protective coating may include a plurality of layers, including different materials or combinations of materials in different layers.

The IACs and IPCs 10 may have circuitry and including electrodes made of conductive materials, such as gold, platinum, titanium, or any other biocompatible conductive material or combination of materials. The IAC/IPC including its housing, may be fabricated with a thickness suitable for implantation under a patient's skin. An IAC/IPC 10 may have a maximum thickness of less than about 4 mm or less than about 2 MM, and the conductive components of the IPC may have a thickness of only 0.02 mm, as supported by the data of FIG. 7.

Alignment Strategies.

Figure 24A:
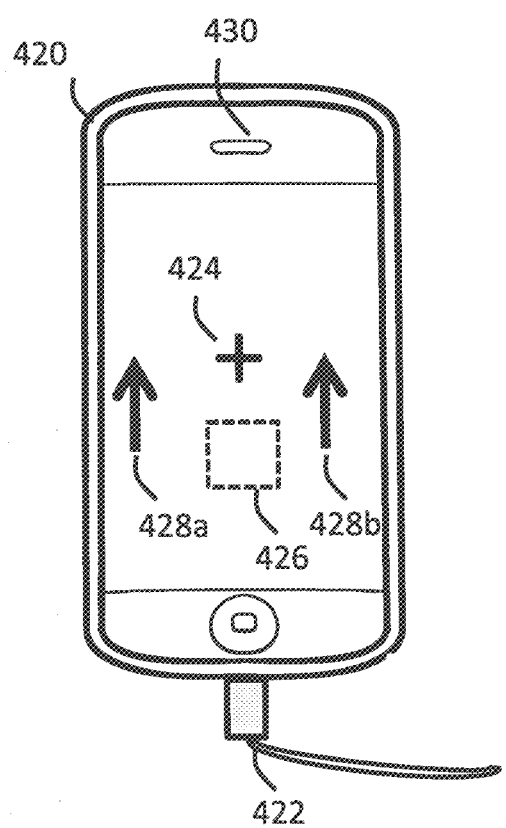
FIG. 24a is a schematic diagram of an embodiment of a controller for a portable TNS system.
Figure 24B:
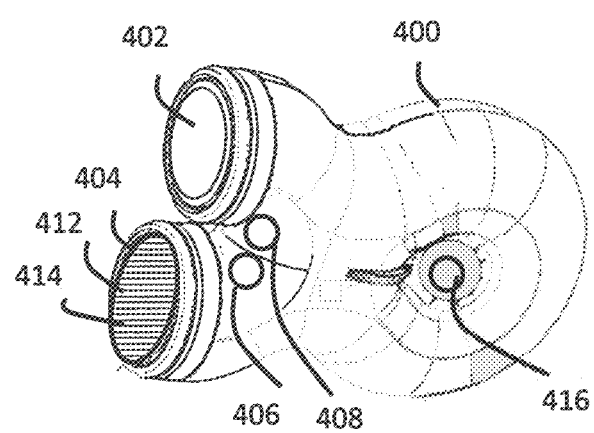
FIG. 24b is a perspective schematic view of a portable TNS system.

Some of the benefit of the current invention rely on the IPC correctly aligned with at least 1 external stimulator. FIG. 24*a* shows a controller for controlling a stimulator deice 400 shown in FIG. 24*b* that may be used by the current invention and which is approximated by the GammaCore tissue stimulator. The device 400 can have all the components disclosed in, for example, US App 20130066392 to Simon, entitled "Non-invasive magnetic or electrical nerve stimulation to treat or prevent dementia". Alternatively, the stimulator device can be implemented in distributed tabletop form such as the device 50 disclosed in FIG. 17. In one embodiment, two stimulators 402, 404 are provided on the stimulator device 400 which can each be comprised of conductive plates each of which can serve as anode or cathode. Additionally, in alterative embodiments of the current invention, the surface of the plates 402, 404 may be divided into separate regions which may be active or inactive. For example, plate 404 is shown as comprising a number of horizontal contact surfaces 412 each of which may be individually activated and which may be separated by non-conductive surfaces such as ridges. Only a portion of the horizontal contacts 412 may be activated (i.e., used to provide a stimulation signal) in order to determine the functional shape of the stimulator. Further, the horizontal surfaces 412 can be adjustably activated (by the patient or otherwise) so that these line up well with at least one implanted IPC 10. Additionally, the horizontal surfaces 412 can be activated to provide for at least one bipolar electrode.

In one embodiment, a camera 406 is provided which can show the user if the device 400 is positioned correctly. For example, the device 400 can use its communication module 68 to communicate with a tablet or smartphone 420 that has been configured to operate software related to positioning the device 400 during use. This can occur using a wireless medium such as Wi-Fi or can occur using a physical cable 422 that connects the smartphone to the device 400, using the port 410. During operation, the device 400 sends the video data to the smartphone which displays images so that the user can see what area of skin is being stimulated.

In one embodiment the user may be tattooed with a permanent or temporary symbol such as the "+" symbol which serves as a location marker 424. In another embodiment there are at least 2 tattoos in order to more accurately align the device. In a further embodiment the tattoos are electroconductive and allow for at least one sensor on the device 400 to issue a signal when a stimulator or sensor of the device 400 is in contact with the tattoo since this could be designed to establish a closed electrical circuit. The stimulator then projects or displays a box visual alignment signal 426 where the field would be located. Visual signals can be superimposed onto the screen such as navigation arrows 428*a* and 428*b* which can indicate to a user how to position the device 400 before delivering stimulation. In other words, the users would attempt to make sure the +symbol resides within the box before, and during, stimulation. Further, rather than having a "+" symbol, the device 400 can also provide a location guidance module 408 which may comprise circuitry and routines for assisting in aligning the system components and may also contain an NIRS sensor and/or laser. The "x" location marker 424 may be generated by software which can optically, or otherwise, detect the position and/or orientation of the IPC 10. A speaker 430 on the smartphone may also issue auditory guidance cues such as "Please move the stimulator slightly up" or a continuous train of beeps that increase in frequency as the edges of the both surface electrodes and the IPC become well aligned.

In an embodiment, the stimulator 400 can use the visual image data collected by camera 406 in order to activate only certain regions of the stimulator plates 402, 404 in response to the data so that the regions which are activated on the stimulators are adjusted to improve the alignment and placement of the stimulation field relative to at least one subcutaneously placed IPC.

In an embodiment, the device 400 can communicate with a tablet or smartphone 420 that has been configured to operate to allow a user to modify the stimulation parameters or protocols. Even though the device 400 may be provided with controls situated on its housing in to adjust the stimulation, some patients such as elderly or physically handicapped patients may not be able to provide for accurate manual control of the stimulation. Using a smartphone or other type of controller which is not disposed within the housing of the device 400, but rather is connected in a wired (accessory port 416) or wireless manner may allow patients to have greater control over the stimulation parameters in a more user friendly manner.

In an Embodiment, the Gamma Core can have an accessory port 416. The accessory port can serve to connect to at least one additional electrode/stimulator. For example, a stimulator or sensor such as a disposable electrode can be attached to a wire that plugs into the accessory port 416. The device 400, can then stimulate from either only stimulator 402 or 404 combined with the electrode which is located more distally. This may be useful, for example, if the device 400 is configured not only for stimulation but also for sensing which occurs before, during, or after the stimulation. In this case, the electrode can be placed so that a measured dipole is recorded as larger than would occur if using 402 referenced to 404 for both stimulating and sensing, since these may be on the same side of the dipole. In the recording of cardiac or EEG data, this can provide for improved measurement. One example, of how this could be used is if the device 400 stimulated the vagus nerve while also recording cardiac activity using two or more electrodes which connected to the accessory port 416. Another benefit is that if the device is used to stimulate the temple of a patient, at least one of the two rigid stimulators 402, 404 can be used to stimulate the temple of a subject, while the distally located electrode may be situated at the back of the head in order to cause the stimulation signal to travel from the fixed stimulators to the electrode (i.e. from the front to the back of the head or vice versa), which may ensure a greater transmission of the signal in to the patient's brain than may occur using the two fixed stimulators located proximal to each other.

In one embodiment, the port 416 could be used to record signals from a surface electrode, which could provide feedback signal (e.g., a measure such as foot EMG) which can be used for aligning the stimulator with the IPC implanted on the PTN. In another embodiment, the EMG electrode can be placed over the larynx to measure vagus nerve activation during eTNS.

In one embodiment the device 400 is configured as a device having at least one fixed stimulator 402 or 404, and at least 1 electrode that is flexible and which may be located at least 5 inches away from the fixed stimulator 402, 404. The at least one fixed electrode may be at least 2 fixed electrodes as in the device 400 shown in FIG. 25. Further, when the flexible electrode is used, only 1 of the 2 fixed stimulators 402,404 may be selectively activated.

Figure 24C:
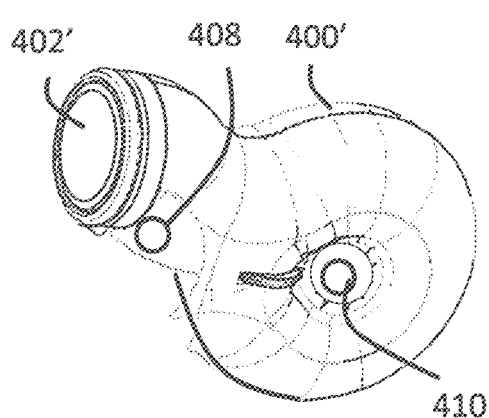
FIG. 24c is a perspective schematic view of a stimulator for providing tissue stimulation using at least one stimulator.

FIG. 24c shows an alternative embodiment in which a portable device 400' that has been configured to provide a laser-, ultrasonic-, electric- or magnetic-based stimulator 402'. Although the stimulator portion of the figure appears fixed, the stimulator may be adjustable. For example, within the housing there may exist movable magnetic coils which may be angled. Further the coils may be replaceable and adjustable (e.g., a Hemholtz coil may be replaced with a figure-8 coil).

Figure 24D:
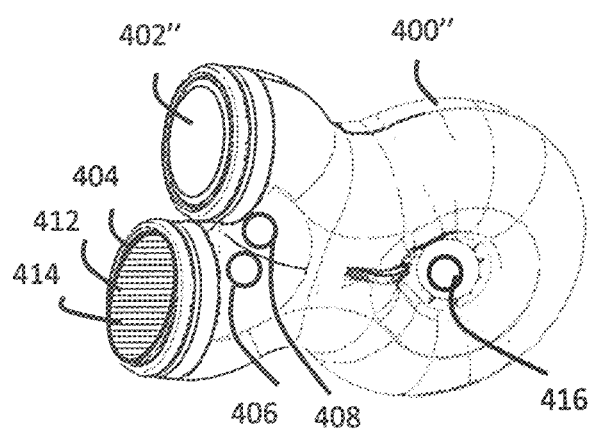
FIG. 24d is a perspective schematic view of a stimulator for providing tissue stimulation using two stimulators.

FIG. 24d shows an alternative embodiment in which a portable device 400" that has been configured to provide a light, ultrasonic, electric or magnetic stimulator 402". The device 400" may be configured with at least one adjustable stimulator, such that the angel or other characteristics of a stimulator may be adjusted in relation to a particular target +IPC combination so that they are well paired. In one embodiment, a method for providing transdermal stimulation therapy to a subject comprises positioning a device 400" with stimulator 402" over at least one of the top or bottom surface of a patient's foot near an IPC located near a tissue target, and providing a stimulation signal through a skin surface to stimulate the target nerve. In one embodiment of the method, the IPC is located near the big toe of a subject and the tissue target is the MPN. In another embodiment, the IPC is located near the three smallest toes of a subject and the tissue target is the LPN.

Figure 25A:
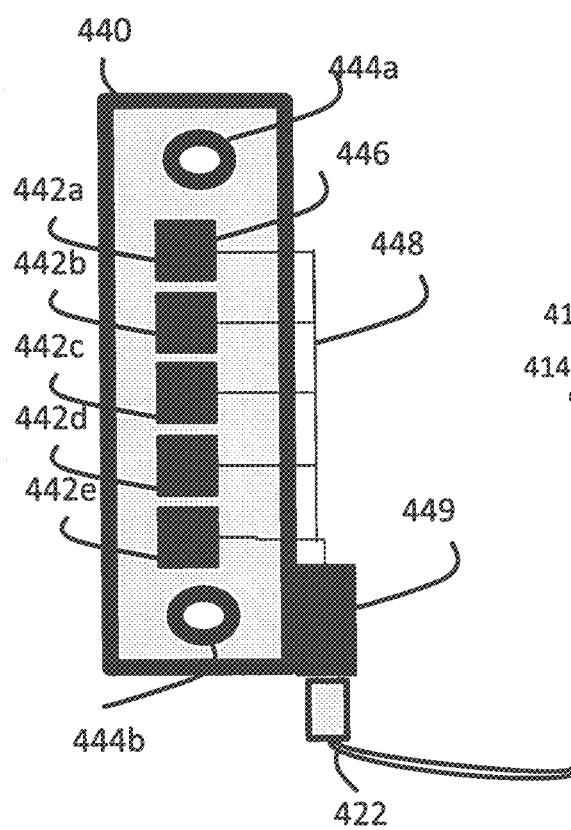
FIGS. 25a-b is a schematic view of an alternative embodiment of a portable TNS system and a multi-contact array stimulator.
Figure 25B:
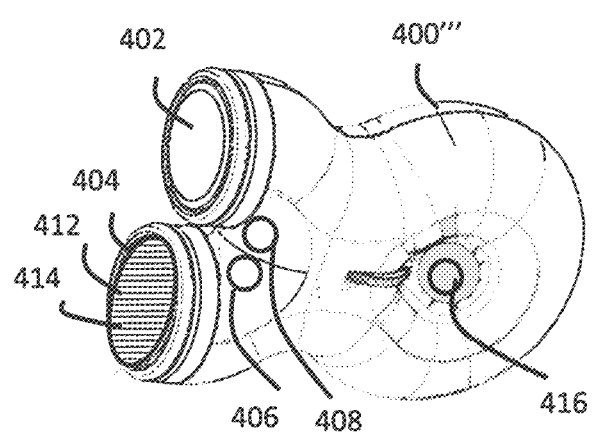

FIG. 25a shows one embodiment having a cutaneous, multi-contact array stimulator 440 that may be used, with the device 400''' shown in FIG. 25b, for example, during nerve stimulation. The array 440 has a series of contact electrode stimulators 442a-e, all of which may be independently activated. If only contacts 442a and 442b are used to provide a stimulation signal then this would produce a smaller functional terminal than if 442a-e were all stimulated. Additionally, subsets of 442a-e can be used to stimulate an IPC of smaller or large length, by allowing a patient or doctor to control which contacts are used during the provision of therapy or by having these defined or determined as part of a stimulation protocol. The stimulating array 440 may also consist of one or more alignment loops 444a, 444b which can be used to achieve improved alignment with the subcutaneously located IPC. For example, a patient may have permanent or temporary tattoos placed according to the location of the IPC, such that the holes (444a, 444b) can be used to accurately visualize these anatomical markers on the patient. The figure shows the top side of the stimulating array 440, where the substrate can be fabricated using a flexible and electrically non-conducting material such as silicone elastomer or nylon. The bottom side will simply have the surface contacts 442a-e and an adhesive surface which is configured to be attached to a subject's skin. Electrical connections 448 run from each contact 442a-e to a port 449, which connects to a plug on cable 422 so that the stimulator 400 can be controlled and powered from the accessory port 416. The subset of the electrode contacts 442a-442e which are used can be controlled by the device 400, either via manual adjustment, by selecting a particular stimulation protocol, or using a graphical interface such as a schematic that is presented on the smartphone, wherein a user may activate 1 or more of the electrode contacts by tapping each virtual electrode of the schematic shown on the smartphone.

In another embodiment a physical landmark, such as at least one bead, may be affixed to the skin or implanted under the skin in order to assist with the correct placement of the device 400 or a stimulator 402, 404. The landmark may provide tactile, visual, or other indication which assists in correctly positioning the external stimulators with respect to at least one implanted IPC.

Controlling and Shaping the eTNS Field

Figure 26A:
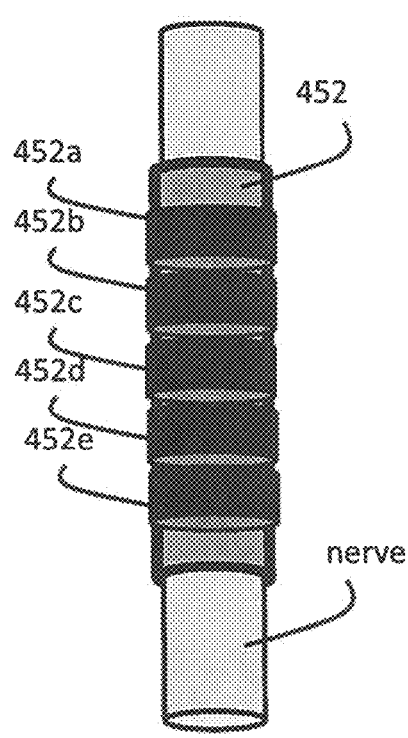
FIG. 26a is a schematic view of an embodiment of a multi-contact stimulator array and a multi-contact IPC array.

In another embodiment, the stimulating array 440 may be coupled to an IPC that also consists of multiple, electrically-conducting elements that are equally-spaced with inter-contact 442a to 442e distances along one or more targeted nerves (FIG. 26a). By aligning the one of the opposing ends of the transcutaneous stimulating electrode contacts 442a to 442e with a corresponding edge of the IPC array 452 of electrically-passive contacts 454a to 454e of the surgically placed IPC array (452), improved modulation of neural activity may be achieved. Improved modulation may be provided by, for example, independently modifying the activating function (e.g., enhanced neural excitation) at multiple locations along a single or multiple nerve(s). Transcutaneous electrical stimulation through all contacts may maximize the overall activation of targeted nerve fibers. Alternatively, when the spacing is sufficient, or the stimulation signals are provided at different times, each passive contact 452a to 452e can be used to activate fibers at a different stimulation frequency. In this manner, one or more contacts may be used to promote the generation of unidirectional nerve action potentials, or to selectively activate only smaller diameter fibers. The latter two methods can be achieved by various means such as using high frequency stimulation, DC current, or quasitrapezoidal pulses (e.g., Fang ZP and Mortimer JT, IEEE Trans BME 1991; Kilgore K M and Bhadra N, Med. Eng. Biol. Comp., 2004).

Figure 26B:
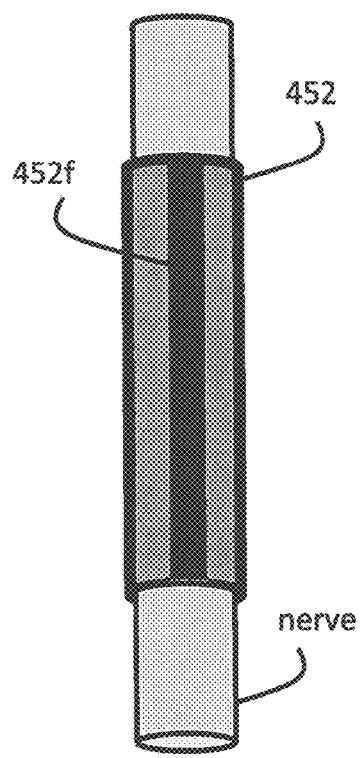
FIG. 26b is a schematic view of an embodiment of an IPC, in which the conductive material is limited to a single conductive strip.
Figure 26C:
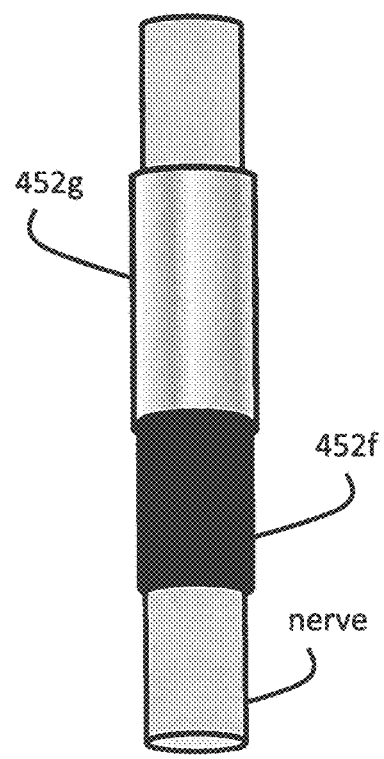
FIG. 26c is a schematic view of an embodiment of an IPC, where an insulating material is applied to the external surface of the conducting material.

In another embodiment, the IPC may be configured to selectively activate a subset of fibers or particular nerve fascicle located within a compound nerve trunk. Examples of such nerves may include the vagus nerve, sciatic nerve, pudendal nerve, posterior tibial nerve, and femoral nerve. This type of spatially selective electrical activation of such subsets of nerve fibers is achieved by designing a hollow cylindrical IPC (such as in FIG. 26b) that consists of a low- or non-conductive substrate material 452 and a strip of high-conductive material 452f along the length of the IPC. This embodiment will selectively enhance the excitability of nerve fibers in close proximity to the strip 452f, while adjacent fibers located in closer proximity to the less conductive material 452 will exhibit a decreased or no change in excitability. With prior knowledge of multiple targets (e.g., fascicles within a nerve trunk), multiple conductive strips 452f may be strategically placed around the IPC. The strips may also vary in width (around the nerve circumference) and thickness.

In another embodiment, enhanced neural activation can be further improved by applying an electrically insulating layer to the external surface of a hollow cylindrically-shaped IPC. The extent to which the insulating layer covers the externally exposed surface may be partial (e.g., one quarter or one half of the cylindrical IPC) or complete (entire surface). This effect can be further enhanced by also applying this insulating layer to the inner surface of the IPC. A key area that must remain electrically exposed to the surrounding environment includes the circumferential edges at both ends of the IPC. This method of enhancing neural excitability works in conjunction with the preferred design of external (e.g., transcutaneous) stimulating electrodes (FIG. 20a and FIG. 20b).

Figure 27:
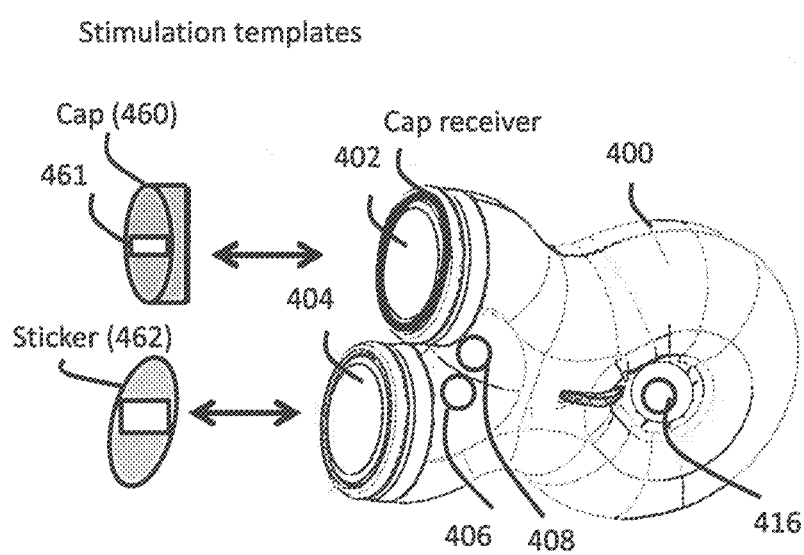
FIG. 27 is a schematic view of a further embodiments of stimulation templates.

Another manner of shaping the field provided by the stimulator is to provide at least one field shaping element such as the stimulation templates shown in example embodiments of a cap 460 and a sticker 462 of FIG. 27. A benefit of using a stimulation template is to achieve improved nerve modulation by aligning at least one edge of the stimulator and an edge, or other region, of an IPC. Even without an IPC, a shaped field can provide improved nerve recruitment compared to using the larger field produced by the entire surface of the stimulator 402, 404. A shaped field may change the current density, field shape, and path through tissue, to improve ability of an externally applied stimulation signal to reach, or selectively stimulate, a target nerve. Templates allow a user or doctor to adjust field parameters such as constraining the shape of the field.

The stimulation template serves as a stimulation mask which provides both at least one first portion that serves as an energy barrier and at least one second portion that allows the passage of the stimulation signal energy. In FIG. 27, an example embodiment is shown wherein the cap 460 provides a non-conductive barrier within which resides a conductive portion (or opening) that allows energy to pass and which may be referred to as a "silhouette" 461. The stimulation template shape is defined by a) the shape of at least one active region (i.e. the silhouette) having a geometry that shapes the energy of the stimulation signal that passas therethrough or otherwise provides for transmission of stimulation signal energy and b) the shape of at least one inactive region such as a non-conductive region or region that otherwise attenuates, diverts, or reflects energy so it does not enter into the patient along a path that would normally occur in the absence of the stimulation template.

Further, the stimulation template may be shaped according to data that is obtained in various manners such as visually by measurement, during the implantation operation, or by using imaging data, or by using data related to a physical dimension of the IPC, or by using subject feedback during a testing routine that determines the desired area on the surface of the patient's skin where stimulation should be provided. An advantage of this approach is to help align the edge of a stimulator with an edge, other portion, of the IPC. As illustrated, a cap stimulation template 460 can be used to shape the field provided at the cutaneous location by having a silhouette 461 or "cut out" that only permits part of the stimulator 402 surface defined by an outline of conductive region to stimulate a subject's skin. The area outside of the shape of a defined conductive region is non-conductive which deters transmission of energy to the skin. The cap stimulation template 460 may be attached to the device 400 by means of a cap receiver component provided as part of the device housing which is shaped to physically engage with the cap stimulation template 460. In an alternative embodiment, a sticker stimulation template 462 may be used with the stimulator surface 404, having an adhesive on one of its two surfaces such that it can be temporarily affixed to the stimulator surface 404. Rather than using adhesive, the sticker or cap template may be formed, at least in part, from a magnetic material having a non-conductive biocompatible coating on its surface. This design uses magnetism to provide temporary securing to and removal from the stimulation surface 404 (which may be formed of a metallic or magnetic material or the housing of the neurostimulator may similarly be magnetic). In a further embodiment the sticker stimulation template may be affixed to the patient's skin rather than the stimulation surface.

In embodiments of the cap or sticker stimulation template, the thickness of the material should provide a "depth" that is sufficient to allow for electroconductive gel to be applied within the conductive region silhouette 461 so that this retains the gel while the remainder of the surface of the template remains dry and non-conductive. In an embodiment, the cap or sticker is non-conductive and formed from plastic, rubber, or other suitable non-conductive material which can be firm or flexible. The silhouette 461 may be further configured with a slight ridge that extends from the stimulation template surface in order to assist in retaining the gel within the shape of the silhouette 461. Further, the gel may be relatively "loose", similar to the conductive gel often used during ECG recording, or may be more of a conductive paste that is firmer, such as hydrogel materials or pastes which are more firm such as those used in EEG procedures, in order to keep the electrodes in place on the scalp. Conductive mediums such as hydrogels can maintain a specific shape and can be manufactured with shapes that allow a good fit within the silhouette 461 to provide improved specificity of the shaped field. Rather than a single conductive region, a stimulation template may define several conductive regions 461. Further, when two stimulation templates are used, one can be used to define one or more anodes and another used to define one or more stimulation contacts each of which serves as a cathode.

In embodiments, and not to be limited by theory, stimulation templates are intended to provide advantages including serving as a spatial filter that shapes the stimulation field geometry and changing current density or path within the patient. The stimulation template provides a barrier to energy transmission (by reflecting, absorbing, blocking, redirecting, or otherwise dampening energy) for a portion of the stimulation signal located outside of a defined geometry while permitting energy to pass within a defined geometry. In an embodiment, an optical stimulation template is formed to permit optical energy—that may include single or multiple wavelengths—of a specific shape to reach nervous tissue and lead to generation of nerve action potentials. In the case of electrical stimulation, the non-conductive barrier will limit/decrease stimulation of the skin adjacent to the surface outside the intended geometry, while the conductive portion 461 (e.g. opening filled with a conductive medium) allows energy to pass from the stimulator to the skin. In an embodiment, a magnetic stimulation template is formed from a conductive material (e.g., metal alloy, conductive mesh), covered in a non-conductive film (e.g., silicone) or plastic layer, with at least one gap or cut out region ("opening") permitting passage of a magnetic field. In an embodiment, a sonic stimulation template is formed using a material that reflect or absorbs sound energy and a "window" that permits a sound energy field to travel from the transmitter into the tissue below skin of a patient. In embodiments, the surface of the stimulation templates that flanks a patient's skin comprises individual portions each having a thicknesses. For example, the thickness may be determined using imaging data to adjust the shape of the template in relation to the specific anatomy of a patient. This modulates the stimulation field so that it is customized to provide targeted activation of a nerve. For example, the stimulation template may formed using a 3-D printer based upon calculations which use MRI, ultrasound, or other imaging data of a patient's leg. The template's design serves to absorb, reflect, direct, or otherwise shape the energy of the stimulation field produced by one or more stimulators so that this is increasingly focused on, and limited to the region of a nerve target, and sufficient to cause nerve activation, while decreasing stimulation of non-target tissue. The stimulation template shape can be designed to deter unwanted muscle stimulation.

In an alternative embodiment, a stimulation template can be formed upon the surface of a stimulator using a non-conductive and biocompatible coating such as silicone. For example, when the housing of a neurostimulator, such as an IAC having active components 142c', serves as an electrode then normally the entire housing serves as a stimulator. By using a stimulate template, only the selected region of the housing which is not covered by the coating is exposed and is able to stimulate tissue. Further, since electroconductive silicone materials have been recently developed, a stimulation template can be formed using both conductive and non-conductive geometries of silicone material, with at least one conductive region defining the geometry of a stimulation area that serves to steer and/or shape the resulting stimulation field(s).

In an embodiment, establishing a field shaping element includes a stimulation template which is an adhesive element or sticker 462 or cap 460 that has an electrically conductive region 461 while the remainder isformed of a non-conductive material that serves as an electrically non-conductive region. The electrically conductive region 461 has a predetermined shape that permits passage a stimulation signal to occur as a predetermined pattern. The adhesive element has a pair of opposing adhesive surfaces for releasable attachment to the skin of a patient (lower surface of adhesive element) and a stimulator surface (upper surface of the element), or at least one of the surfaces is adhesive.

In an embodiment, a method of providing treatment of a pelvic floor disorder comprises providing a neurostimulator 400 that configured for providing a stimulation signal to at least one stimulator 402, 404 located external to a patient. The method includes establishing a field shaping element such as 460 or 462 that is coupled to (or incorporated into the operation of) the stimulator (functionally or physically) in order to allow collaboration therebetween. The field shaping element is designed to permit adjusting of the shape of one or more stimulation fields associated with a set of one or more stimulation signals. This allows the advantage of providing improved targeted stimulation of a target nerve. The method further includes operationally activating the neurostimulator 400 which is positioned and/or otherwise adapted to provide a stimulation signal to a target nerve in a lower limb of a patient with a pelvic floor disorder. The stimulation protocol is defined with stimulus signal characteristics (e.g., a modulation rate previously shown to provide symptom relief) that are configured to treat the pelvic floor disorder. Treatment can include providing relief for at least one symptom associated with the disorder. The target nerve can be a nerve in the lower limb including the saphenous nerve or PTN and the pelvic floor disorder is an overactive bladder disorder. The stimulator 402, 404 can be an electric or magnetic stimulator or may be a light or sonic-based stimulator. When the stimulation template formed of an electrically non-conductive material portion and the silhouette 461 is formed of an electrically conductive material portion then the electrically non-conductive portion limits the region of the stimulator surface 402 that stimulates a portion of the skin of the patient.

In embodiments the field shaping element is a stimulation template that has at least one adhesive surface that is at least partially electrically non-conductive to limit the stimulation field. Rather than using adhesive, the template can be realized as a surface that is positioned between the stimulator and the patient and which restricts at least one shape, location, and/or strength of the stimulus waveform that is transmitted into he subject from at least one stimulator in order to advantageously affect the shape of the stimulation field in the tissue of the patient with respect to successfully provide nerve modulation or improve its selectivity. Additionally, the stimulation template can be formed from at least two layers that are electrically non-conductive for at least a portion of their geometry which flank an electrically conductive layer sandwiched therebetween. Similarly, an electrically conductive material may have both an upper side and a lower side (facing a stimulator and patient, respectively) wherein each side is coated with a non-conductive film for at least a portion of its surface which limits the shape of the stimulation signal.

In an embodiment, the stimulation template can have a predetermined shape that provides for the passage of energy as function of a physical dimension of an IPC (or IAC). For example, establishing at least one field shaping element includes a stimulation template that has a portion (e.g. 461) that is adapted to be shaped according to the patient's anatomical data. The shape of a transmission window (located within a non-conductive surface) that allows energy to pass has a shape that approximately aligns an edge of the window with an edge (or other region) of the IPC and/or a region of a nerve. The stimulation template can be shaped according to imaging data of the patient which may include imaging of the IPC location and shape. Or, alternatively, the template is adapted to be configured according to assessment of the patients feedback provided during a procedure that determines an area on the surface of the patient's skin where stimulation is determined be successful in stimulating a target nerve and the template is shaped to promote a similar field shape during subsequent treatments.

IPC Component Designs.

The IPCs used in the disclosed invention may have many shapes and forms. The embodiments shown in FIGS. 28-30 show some illustrative embodiments with the understanding that the elements of the IPC can have many shapes, dimensions, and sizes. The illustrative IPCs may have additional features not shown here.

Figure 28A:
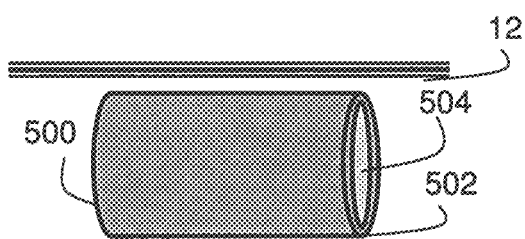
FIGS. 28a-e show schematic views of further embodiments of IPCs.
Figure 28B:
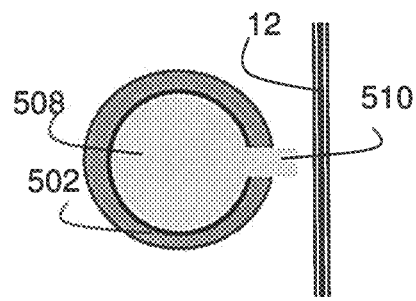
Figure 28C:
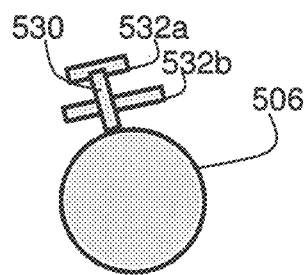
Figure 28D:
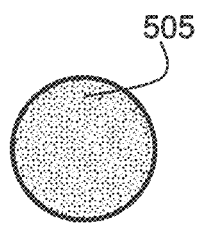
Figure 28E:
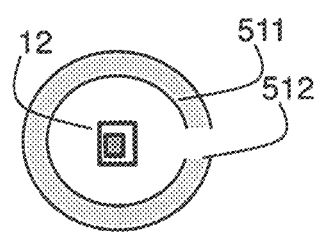

FIG. 28a shows an IPC 500 which is a rod having an outer sheath 502 that may be comprised of an electrically non-conductive material or conductive material and inner portion 504 that is conductive. One possible advantage of this embodiment maybe that the electrical current provided by a stimulator would travel through the conductive portion and the conductive edges may serve as 2 points which may increase activation of the adjacent nerve tissue, on each edge of the IPC, to stimulate nerve 12 with enhanced nerve stimulation. FIG. 28b shows an alternative embodiment in which the outer sheath 502 insulates the majority of the conductive portion 508, but a conductive lip 510 extends outside of the sheath and stimulates the nerve 12 which is shown oriented perpendicularly to the IPC. This may be a preferred orientation/configuration when the purpose of the stimulation is to provide a nerve block in a specific portion of the nerve 12. FIG. 28c shows an embodiment of the IPC in which it is simply a conductive rod 506 (going into and out of the page). FIG. 28d shows a rod which is made of a mesh material 505 which serves to decrease the surface area of the IPC and may thereby serve to increase coupling with its paired stimulator. FIG. 28e shows an embodiment where the IPC is a hollow conductive cylinder 510 which is wrapped around the nerve 12, as may be seen with conventional nerve cuff designs. The cylinder has an opening 512 which allows it to accept tissue into an inner portion so that the cylinder may surround a tissue target such as a nerve 12.

Rather than being a conductive rod, an IPC can be a conductive cylinder, or may be a conductive thread (similar to conductive wire suture such as that which may be secured to tissue near a target nerve), a mesh, a biocompatible conductive gel that is able to maintain its shape (such as a conductive gel, a flexible, organic, composition of conductive polymers patterned onto slices of hydrogel that may be surgically implanted near the target nerve or into a receptacle having a pocket for accepting the gel), a plurality of conductive particles (which may be injected into the target nerve, tissue around target nerve), suitable micro- or nano-based materials that allow both biocompatibility and suitable conductivity, as well as different types of conductive nerve cuff electrodes.

Figure 29A:
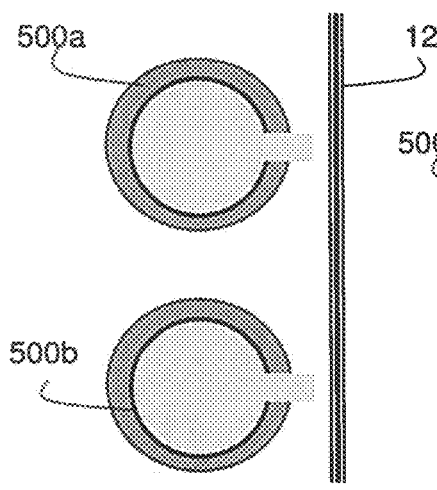
FIG. 29a, b, c show schematic views of still further embodiments of IPCs.
Figure 29B:
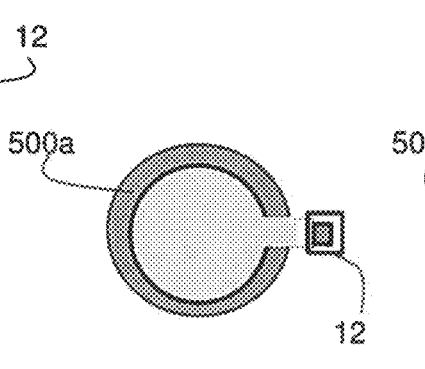
Figure 29C:
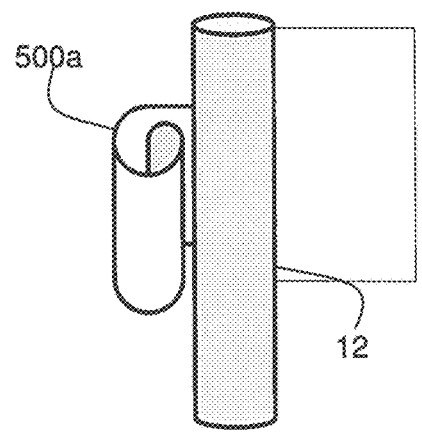

FIG. 29a shows 3 IPCs situated at different locations on a nerve 12 which is located perpendicularly to their lengths, where the first IPC 500a has a different length than 500b in order to allow 2 different stimulators to differentially stimulate the 2 portions of the nerve while providing stimulation treatment. FIG. 29b shows an IPC which is aligned in the same plane as the nerve in order to provide stimulation along the length of the nerve (both the IPC and nerve are going into and out of the page). FIG. 29c shows an IPC fabricated such that it coils itself into a hollow cylinder at rest, where the inner diameter is approximately equal to the diameter of the nerve 12. This self-sizing property would provide an intimate interface between the IPC and the nerve, and also prevent nerve compression by the IPC following implant (e.g., due to nerve swelling).

Figure 30A:
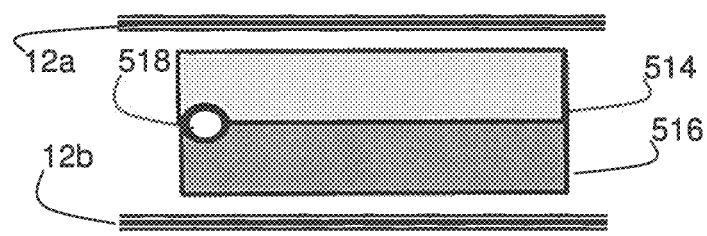
FIGS. 30a-d show schematic views of additional embodiments of IPCs.

FIG. 30a shows an IPC with both a conductive portion 514 and a non-conductive portion 516, which may also be realized by a portion of the IPC which is coated so as to not allow electrical coupling with a stimulator. In an embodiment, the non-conductive portion coating may only reside on half of the IPC, such as serving to coat the underside of the IPC (when the stimulator is located at the top of the page). In the case where the IPC is situated between two nerves where one is the target 12a, and the other is non-target adjacent nerve 12b, then the partial shielding may prevent, or deter, the non-target nerve from being effected by the eTENS. Accordingly a stimulator situated at the top of the page, or positioned at the angle of the viewer looking into the page, would preferably provide stimulation to nerve target 12a, while the non-conductive portion 516 would insulate the field from the non-target tissue area 12b. At least one suture hole securing element 518 may be provided on the IPC to allow the IPC to be affixed to tissue in the area of nerve.

Figure 30B:
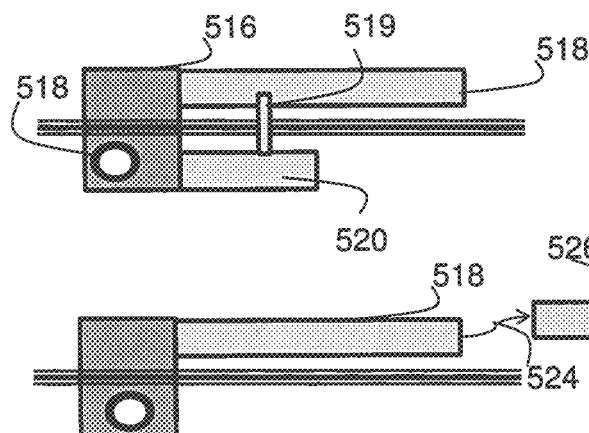

FIG. 30b shows an IPC with at least a first portion 519 and second portion 520. This allows the nerve to be stimulated if the stimulator is aligned with an edge of portion 519 or 520. An advantage of this embodiment is to increase the chance that the stimulator will be approximately aligned with at least one edge of the IPC. A conductive element 521 may serve to electrically connect the two conductive portions 519, 520 so that if the first portion influences an electrical field in proximate tissue, the conductive element 521 may allow the IPC to extend this influence to tissue proximate to the second portion 520 of the IPC.

A stimulus router system (SRS, developed at the University of Alberta) is another example of an implanted device that achieves a minimally-invasive means of electrically activating the peripheral nervous system. The SRS consists of a metal disk 524 (termed the 'pick-up terminal') that is physically connected via lead wires to an implanted nerve electrode. The pick-up terminal is surgically placed just under the skin surface and 'captures and re-routes' electrical pulses applied by an external cutaneously applied electrode. Thus, the nerve electrode is powered by means of a transcutaneous coupling mechanism. The system is currently undergoing clinical feasibility testing. This system is essentially identical to conventional nerve stimulation systems, except for the absence of an implanted pulse generator. Instead of an implanted electrical source, this approach utilizes an external stimulation device and at least one subcutaneous pick-up terminal, which solves the power/control issue at the cost of other potential issues related to long-term use of the SRS. Further, the effectiveness of the SRS system may be compromised by non-optimal design of its surface electrode +pick-up terminal coupling mechanism. The methods and systems of the current invention can be used to improve the SRS system.

Figure 30C:
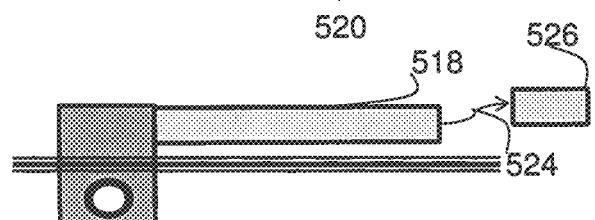

FIG. 30c shows an embodiment of an IPC in which a first conductive component 518 is attached by a flexible conductive element 524 to an electrode 526 located away from the first conductive component. In one case the first conductive component 518 serves as a "pick-up" electrode which can then relay electrical energy to a more distal location. If the first conductive element 518 or electrode 526 is located directly under the skin then this embodiment may approximate an SRS system. However, as the pick-up electrode moves away from the skin then the principles and guidelines of the disclosed invention related to eTENS can be used to pair the IPC with the stimulator in more efficient manner. For example, aligning the edges of the stimulator with the conductive component 518 or electrode 526, or modifying the shape of a stimulator and a paired conductive component 518 and according to the distance between the two system components, as well as other factors, has been disclosed. By following the principles of the invention the distance between the stimulator and IPC may be made much greater than previously understood while still providing sufficient stimulation of target tissue to achieve therapy.

Additionally, a tube or nerve cuff created from, or having at least a portion comprised of, a non-conductive material may be used to insulate non-target nerves from electrical fields while a conductive IPC is used to increase target nerve responsiveness to stimulation. An IPC can be configured with non-conductive portions (e.g., "shield-flaps" 118) which are deployed/situated during implantation to shield non-target nerves from responding to stimulation.

Figure 30D:
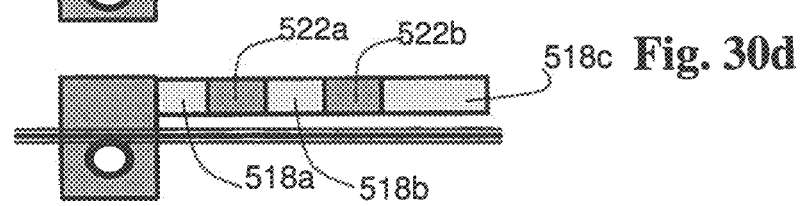

FIG. 30d shows an embodiment of the IPC in which there are several portions with a particular attribute 518a, 518b, 518c (e.g. the attribute may be electrically conductive) which are interspersed by portions without that attribute 522a, 522b (i.e. non-electrically conductive). This design can be used either to stimulate different portions of a nerve or to increase the probability that at least one stimulator edge will align with an edge of a conductive portion in order to increase coupling according to the principles of the current invention. Instead of conductive and non-conductive portions the particular attribute may be sonically resonant to energy provided by, for example, an ultrasonic transducer (the resonant portions can absorb more energy when they are driven at a frequency that matches a natural frequency, or harmonic, of vibration of the stimulator energy). Since acoustic resonance is a form of mechanical resonance, then any stimulator source that produces energy of a frequency that matches the natural frequency of the IPC portion with that particular attribute 518a, 518b, 518c may be used. In one embodiment, the resonant portion of the IPC may be a solid or hollow rod that resonates at a frequency provided by the stimulator. In another embodiment, the portion with a particular attribute 518a, 518b, 518c is configured to either reflect or absorb light in order to enhance the stimulation of adjacent tissue. For example, the portions may be reflective and may be angled such that light energy sent from a transmitter is reflected by the portions onto a specific area of tissue to be stimulated.

Figure 31:
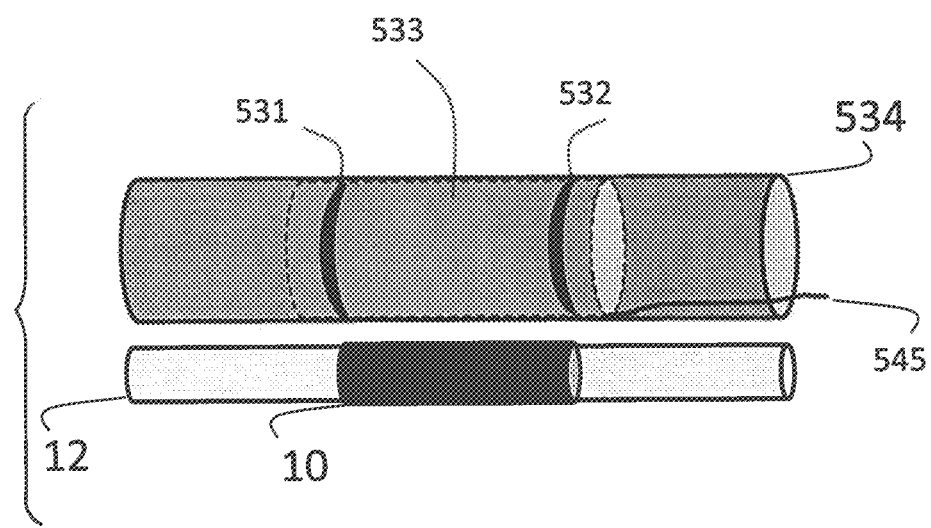
FIG. 31 is a schematic view of an embodiment of an IPC, which is used to achieve enhanced nerve activation by trans-vascular electrical stimulation.

FIG. 31 shows an intravascular stimulator that is connected by a lead wire to an external stimulator. By providing stimulation through a vascular stimulator to an IPC positioned on a nerve, stimulation of the nerve may be enhanced.

Figure 32:
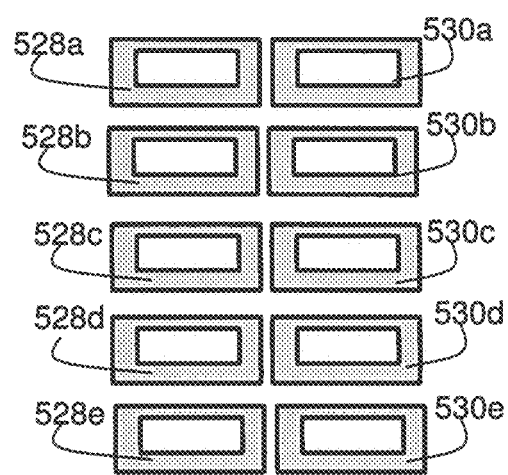
FIG. 32 is a schematic view of a still further embodiment of an IPC.

FIG. 32 shows two arrays of surface stimulators 528a-e and 530a-e. The stimulators are located on a patient's back and at least one stimulator is paired with an implanted IPC located proximate to a spinal nerve. By activating stimulators 528a and 530a the stimulation signal provide can be modulated by at least IPC located within the patient. Alternatively, by activating selected pairs of stimulators of the array, such as 528a and 530b, the stimulation signal can follow a different pathway when providing stimulation to at least one IPC in a patient. In the embodiment of FIG. 32, each of the stimulators can be connected to a device 50/400 which is able to independently activate the stimulators in order to provide patterns of stimulation according to a therapy protocol stored in the device, or which can be controlled by the patient using manual controls to selectively activate each stimulator.

Clinical Applications

The current invention can be applied in numerous therapies that utilize any form of tissue stimulation.

The enhanced transcutaneous nerve stimulation methods and systems of the current invention can be used for neuromodulation therapy. One embodiment involves electrical stimulation of peripheral nerves that are located in relative close proximity to the skin surface. Some examples of suitable anatomical targets include the occipital nerve, vagus nerve, recurrent laryngeal nerve, sacral spinal nerves, pudendal nerve, posterior tibial nerve, and thoracic/lumbar nerves (lower back). One or more nerve targets can be used to treat acute/chronic pain, lower urinary/fecal dysfunction, epilepsy, depression, dysphasia, and other disorders as is well known. In some of these therapeutic embodiments, an implantable device may be used to provide enhanced electrical stimulation therapy. For example, an implanted system can stimulate the sacral nerve, and an enhanced nerve stimulation system is used to stimulate the PTN.

The enhanced nerve stimulation may also be used to treat patients who are refractory to drug therapy or conventional transcutaneous stimulation therapy. It may also be used in combination with drug therapy to enhance the therapy or in order to improve the responsiveness of refractory patients.

Embodiments of the present disclosure may be for use with patients having specific conditions which are modulated by electrical stimulation. Embodiments may be used with any patient who desires nerve modulation of the brain or body. In addition to use in patients with obstructive sleep apnea, migraine, headaches, hypotension, hypertension, addiction, eating disorders, etc., embodiments may be used in many other areas. Application can include, but not be limited to: brain stimulation (e.g., treatment of Parkinson's, and depression); stomach muscle stimulation; treatment of obesity; back pain; incontinence; overactive bladder; menstrual pain, and/or any other condition that may be affected by tissue modulation.

Embodiments of the disclosed invention can be used in rehabilitation therapies, such as functional electrical stimulation (e.g., chronic spinal cord injury or stroke), that are used to restore lost or impaired function. Examples include rehabilitative strategies involving stimulation provided to modulate upper and lower extremity function, trunk stability, and swallowing. For example, in dysphagia, the IPCs of the current invention could improve the reliability an external stimulator to stimulate muscle in a targeted manner in order to deter aspiration.

The disclosed invention can also be used for improving conventional brain stimulation and deep brain stimulation (DBS) therapy. One embodiment involves therapy that is enhanced by surgically implanting one or more IPCs on target tissue in physical proximity to an implanted DBS electrode. The IPC is implanted in a target location to enable suitable electrical activation of a target area and decreases the effect of any sub-optimal placement of, or migration of, a DBS electrode. The IPC may be less likely to migrate because it is not connected to a pulse generator. The IPC may be used with a DBS stimulator which is operated in a bipolar mode or unipolar mode. In the case of bipolar mode, the IPC is preferably the same size as the distance between adjacent electrode contacts of a DBS lead that is providing stimulation. In the case of monopolar stimulation, the IPC size may be defined as a function of the distance between the monopolar electrode and either the IPC or the implanted medical device that is providing the stimulation signal (and serving as the inactive electrode). As an example of monopolar stimulation, the return electrode may be set similar to the cut surface of the leg, furthest from the stimulating electrode (see FIG. 1a). This novel system and method can compensate for poor electrode placement that may alternatively require relatively higher stimulation amplitudes. An advantage is less frequent battery replacement and also deterring habituation.

Reduced stimulation amplitude can also decrease stimulation-evoked side-effects and stimulation of non-target tissue.

Nerve Stimulation for Modulation of Weight and Treatment of Obesity.

As reviewed by Yoneshiro et al (Recruited brown adipose tissue as an antiobesity agent in humans, 2013), Tam et al (Brown Adipose Tissue, Mechanisms and Potential Therapeutic Targets, 2012), and Broeders et al (Endogenous ways to stimulate brown adipose tissue in humans, 2014), brown adipose tissue (BAT) has arisen as a promising mechanism in modulating weight and intervening in disorders such as obesity. Modulation (e.g., activation, re-activation, or recruitment) of BAT using a stimulator and at least one IPC, implanted in a relevant tissue target, may be used to protect against the onset of obesity and related metabolic disorders by modulating fat distribution and level. BAT modulation under the current invention, may also be used for weight modulation, treatment of obesity and its co-morbidities, such as diabetes and hypertension, and modulation of mechanisms involving metabolic control, food intake and processing, as well as sensations fullness. Since BAT may play a role in modulating thermogenesis, lipolysis and oxidative metabolism, enhanced modulation of BAT activity, using an IPC of the current invention, can improve modulation of these other processes. The electrical stimulation provided by the IPCs of the current invention may be used to improve transcutaneous stimulation of tissue in combination with BAT interventions such as temperature and diet.

Since the vagus nerve mediates peripheral signals to the central nervous system, connecting to sympathetic nerves that innervate BAT, vagus nerve stimulation using an IPC and external stimulator can be used to modulate BAT activity, to affect energy expenditure, basal metabolic rate, body mass index, and body fat. Vagus nerve stimulation, using the systems and methods of the current invention, can be used for approximately chronic, acute, or periodic treatment. For example, the stimulator may be an electrode that is stuck to the patient's neck for long periods of each day or at night, during sleep.

Using the IPC in order to provide increased selectivity of the vagus nerve stimulation from an external stimulator is an improved manner of providing therapy to modulate a patient's weight, sympathetic nervous system activity, and parasympathetic nervous system activity. Since white adipose tissue (WAT) and BAT communicate with the brain via sensory nerves and the IPC can be implanted on selected sensory target nerves. Implanting the IPC and using a stimulator to stimulate the vagus nerve may be used to treat any disorder for which other types of vagal nerve stimulation are otherwise used.

FIG. 21 shows a schematic of a nerve stimulation system which includes at least one IPC which is implanted at a site that is appropriate for modulating neural activity related to Brown adipose tissue regulation, such as distribution, growth, or function. In one embodiment, IPC #2 is surgically placed within the BAT, in close proximity to the autonomic nerves innervating the adipose tissue located in the supraclavicular area. The dimensions of both the IPC and surface electrode are adjusted such that the stimulation thresholds for activating the autonomic nerve fibers are reduced (i.e., increased neural excitability). The stimulation system can be modified to accommodate the electrical activation of BAT in other anatomical locations (e.g., perivascular, paraspinal, renal, and sub-scapular areas). In another embodiment, the metabolic or physiological activity of BAT can be modulated by electrical stimulation using IPC #1 surgically implanted to stimulate the vagus nerve. FIG. 21 shows an IPC implanted around the cervical vagus nerve and using surface stimulators to deliver electrical stimuli. Alternative methods of delivering electrical stimuli may include placing the stimulating electrode within the carotid vein or artery (within the cervical area), such as to achieve transvascular nerve stimulation.

Modulation of weight and/or appetite may also be provided by electrical nerve stimulation of dermatome T6 and areas related to T1 to T12. For example, Ruiz-Tovar et al (Percutaneous electrical neurostimulation of dermatome T6 for appetite reduction and weight loss in morbidly obese patients, 2014) showed electrical stimulation of dermatome T6 was able to provide for both appetite reduction and weight loss. In an embodiment of the invention a patient may be selected 46 who is desirous of weight modulation. As shown in FIG. 17, at least one tissue target can be selected and/or assessed 48 as suitable. At least one IPC can be surgically implanted on, or adjacent to, at least one tissue target 12 shown in FIGS. 1a-1c such as target tissue in the T6 area (e.g., T6 related skin areas, thoracic spinal nerves, dorsal roots) 132 of FIG. 19. The IPC can be attached to vertebrae, nearby dura or pia tissue, enticulate ligaments or other structure which is deemed appropriate 48 to maintain the IPC in a proper location. At least one stimulator 130 shown in FIG. 19, may be cutaneously positioned 32 to provide stimulation to tissue adjacent to the IPC. The stimulation of tissue 36 may then be presented by a nerve stimulation device 50 according to a regimen which provides for therapy to be delivered according to the stimulation regimen 36. The stimulation may then be presented 36 according to a regimen which provides for therapy to be delivered. Results may then be assessed 38 and the therapy continued according to the regimen 40, or adjusted 44 if that is deemed to be appropriate 42.

IPCs can be implanted to provide neuromuscular electrical stimulation (NMES) of targets that may be used to modulate energy expenditure and promote weight loss. Hsu et al, (Effect of neuromuscular electrical muscle stimulation on energy expenditure in healthy adults, 2011) showed a linear dose-response relationship existed between NMES stimulation intensity and increased energy expenditure. Since IPC use allows cutaneous stimulation intensity level to be functionally higher with respect to the tissue target (i.e. the tissue target is more responsive to electrical signal provided by a stimulator) this can permit lower stimulation intensity while obtaining an effect normally requiring larger amplitude stimulation without the IPC due to intervening tissue. Tissue targets for IPC implantation may be the abdominal muscles, gluteal maximum, quadriceps, etc.

The IPC of the current invention can be implanted in an auricular region and used with a stimulator top provide modulation of auricular nerve tissue targets that can be used to modulate various medical conditions or create desired changes in patients. For example, Schukro et al (The effects of auricular electroacupuncture on obesity in female patients—a prospective randomized placebo-controlled pilot study, 2014) showed auricular stimulation can be used to promote weight loss. At least one stimulator may be cutaneously positioned to provide stimulation to tissue adjacent to the IPC, for example, to provide electrical auricular acupuncture. In one embodiment the IPC can be placed proximate to targets including the intermediolateral nucleus or the splanchnic nerve or various projections of the spinal nerve that provide afferent or efferent connections to tissue and organs that modulate weight, appetite, and metabolism and a stimulator can be suitably situated to provide enhanced stimulation of those targets in order to modulate states or conditions of a patient.

Modulation of Facial Nerves for Treatment of Disorders Such as Headache.

One application of the invention is related to surgically positioning the IPC in the facial region to stimulate the facial, intermediate, and/or cranial nerves. The system and method can include at least one IPC implanted on, around, or proximate to, at least one of a vidian nerve (VN), a greater petrosal nerve (GPN), a deep petrosal nerve (DPN), or a branch thereof, of the person. At least one stimulator can be used to apply an electrical signal to a target near the IPC such as the VN, the GPN, the DPN, or a branch thereof. In one embodiment, the electrical signal used to stimulate a nerve target near the IPC can be provided by at least two cutaneous stimulators, with at least one of the electrodes being positioned on the person's face or head. In the treatment of migraine or headaches, the enhanced nerve modulation (e.g., inhibition) provided by the IPC and a matched stimulator is used to reduce the sensation of pain or to block a process related to the generation of the migraine. An implanted device 110, shown for example in FIG. 18*b*, may be used in combination treatment with an IPC and external stimulator to provide enhanced transcutaneous stimulation on an acute basis when additional therapy is needed. For example, pain sensation or migraine treatment may require subcutaneous implantation in the back of the neck, near the hairline of a subject, or behind the ear of a subject, to modulate the occipital nerve, greater occipital nerve, lesser occipital nerve, and/or the trigeminal nerve.

Modulation of Bone Growth, Decay, and Strength.

In the current invention as shown in FIG. 18*b*, a patient may be selected 46 who is desirous of receiving treatment to treat or prevent bone loss or promote both, growth, strengthening. At least one IPC can be surgically situated in or adjacent to a target area 30 so that target tissue, such as bone (e.g., spinal vertebrae), is stimulated. At least one stimulator may be both selected and cutaneously positioned 32, based upon the characteristics of the IPC, including the position of the IPC relative to the stimulator, to provide stimulation according to selected stimulation parameters 34. The stimulation may then be presented 36 according to a treatment regimen. Stimulation related results can then be assessed 38 and the therapy continued according to the regimen 40, or adjusted 44, if that is deemed to be appropriate 42. Using the IPC to enhance stimulation level on an intended bone target region may functionally increase the intensity from a surface stimulator compared to that which would be provided in the absence of the IPC. Some drugs or medical interventions may show increased specificity, activation, or binding for a target area in the presence of an IPC when stimulation to that region is provided. One mechanism of therapy may be obtained when the IPC causes target tissue to become more permeable, for example, to a drug Modulation of Muscle Growth, Decay, and Strength.

In some embodiments the current invention of enhanced stimulation can be used to prevent deep muscle atropy or to otherwise modulate muscle tone, growth, activity and decay. For example, Tanaka et a1 (Comparison of pre-modulated interferential and pulsed current electrical stimulation in prevention of deep muscle atrophy in rats, 2014) used a rat model and compared the effects of electrical stimulation using pulsed current (PC) and pre-modulated interferential current on prevention of muscle atrophy in the deep muscle layer of the calf. In the current invention a patient may be selected who may have a muscle disorder or who may wish to deter atrophy or increase growth. At least one IPC can be surgically situated in a target area so that target tissue, related to modulation of muscle tone or activity, is adjacent to the IPC. At least one stimulator may be cutaneously positioned to provide stimulation to tissue adjacent to the IPC. The stimulation may then be presented according to a protocol which provides for therapy to be delivered according to the stimulation regimen. Results then can be assessed and the therapy adjusted if needed. In one embodiment the stimulation is provided by pre-modulated interferential current provided by at least two stimulators in treatment (for example, treatment of carpal tunnel syndrome).

Modulation of Swallowing and Sswallowing Ddisorders and Symptoms

Modulation of neuromuscular targets may be used to treat various swallowing disorders. In the current invention a patient may be selected 46 who is experiencing dysphagia, who is experiencing globus, or who wishes to deter aspiration related issues. As shown in FIG. 17, at least one tissue target can be selected and/or assessed 48 as suitable. At least one IPC can be surgically situated in, or adjacent to, at least one tissue target 30 such as target tissue in an area of the anterior neck which may be the site which is the primary cause of the dysphagia, as shown in 142*c* of FIG. 21. At least one stimulator 142*c* (e.g., surface electrode #3) may be cutaneously positioned, as shown in block 32 of FIG. 17 to provide stimulation to tissue adjacent to the IPC 32. In an embodiment, at least 4 leads are provided as two pairs of electrodes (one for each side of the neck), with each pair of leads primarily stimulating a respective IPC. The stimulation may then be presented by a nerve stimulation device 50 according to a regimen which provides for therapy to be delivered according to the stimulation regimen 36. Results may then be assessed 38 and the therapy continued according to the regimen 40, or adjusted 44 if that is deemed to be appropriate 42. One regimen that may be appropriate is placing the stimulators and IPCs to target the anterior (and/or posterior) belly of the digastrics, myohyiod and/or thyrohyoid, or other infrahyoid muscles group, targets in order to improve hyolaryngeal excursion/elevation with muscle contraction. This therapy can serve to deter atrophy. In one embodiment, sensors may be used to provide for measure of accelerometry, such as measures the epidermal vibration signals on a patient's neck during swallowing or measures related to muscle activity/tonality which may be made before or after swallowing, or in a non-swallowing period, or both a swallowing and non-swallowing period. The data from the sensors can be evaluated 38 by an algorithm in the device 50, or by the patient or doctor.

Modulation and Treatment of Breathing Disorders and Obstructive Sleep Apnea (OSA)

In patients with OSA, a primary target response of nerve stimulation may include contraction of a tongue muscle in order to move the tongue to a position that does not block the patient's airway. The largest of the pharyngeal muscles responsible for upper airway dilation is the genioglossus muscle, which is one of several different muscles in the tongue. The genioglossus muscle is responsible for forward tongue movement and the stiffening of the anterior pharyngeal wall. In some patients with OSA, the neuromuscular activity of the genioglossus muscle is decreased compared to non-OSA individuals, accounting for insufficient response and contraction to open the airway as compared to a non-OSA individual.

When a sensor and sensing system 55 is provided in, or used by, the device 50, then a processing module 58 can be configured to detect the onset or presence of a sleep apnea event (e.g., snoring can be detected by a microphone or a decrease in airflow can be detected via a flow sensor) or a sleep apnea precursor (e.g., a particular change in EMG pattern that tends to precede an event). The detection of such an event by the processing module 58 may require stimulation to occur. For example, appropriate placement of the IPC seen in block 48, can allow stimulation 36 to modulate the genioglossus muscle of the patient to relieve or avert the OSA related event. Such stimulation may result in contraction of the muscle and movement of the patient's tongue away from the patient's airway.

A system for tissue modulation 50 may be realized as a sleep disordered breathing treatment system comprising an IPC 10 to provide enhanced stimulation of target tissue, at least one pair of stimulation electrodes 88, 90 shown in FIG. 18a is configured to provide an electrical field to target tissue in the proximity of the IPC 10 in order to modulate the target tissue, wherein the IPC 10 is configured for implantation in a subject proximal to at least one of a genioglossus muscle in the vicinity of a hypoglossal nerve (i.e. cranial nerve XII) and the hypoglossal nerve. In one embodiment the stimulators are configured to provide an electric field such that a portion of the field lines extend along a length of the hypoglossal nerve such that the delivery of the electrical, in the presence of appropriately situated IPCs, signal causes modulation of the hypoglossal nerve from a location spaced apart from the hypoglossal nerve. The stimulator may be placed external to a blood vessel, and the IPC may be placed inside or proximate to a blood vessel, for stimulation of an adjacent nerve.

Modulation of Disease States.

Modulation of vagal targets can play a role in deterring disease related complications. For example, Schulte et al (Loss of vagal tone aggravates systemic inflammation and cardiac impairment in endotoxemic rats, 2014) have shown, using vagotomized, rats that, after vagotomy, the inflammatory response was aggravated, measurable by elevated cytokine levels both in plasma and ventricular tissue. To reverse both hemodynamic and immunologic effects of diminished vagal tone, even a brief stimulation of the vagus nerve was enough, for lipopolysaccharide (LPS)-induced septic shock during initial LPS infusion. Accordingly, targeted modulation of the parasympathetic nervus vagus using at least on IPC, according to the systems and methods of the current invention, might play a major role in maintaining hemodynamic stability and cardiac immune homeostasis during conditions such as septic shock. Accordingly, patients suffering various disease states, such as TBI patients, may be selected 46 for targeted vagal nerve modulation via the current invention may offer suitable treatment. Modulation of other targets such as the median nerve, using IPCs, may also assist in modulation of disease states.

Modulation of Pain and Sensory Information

Various types of acute and chronic pain may be modulated according to the current invention of enhanced transcutaneous nerve stimulation. Treatment of pain disorders, using at least one IPC and paired stimulator, related to unwanted activity within the ulnar, median, or other nerves can assist in patients with cubital tunnel syndrome, carpal tunnel syndrome. Treatment of patients suffering from tarsal tunnel syndrome, or plantar fasciitis may be assisted by targeted stimulation of targets such as nerves in the foot, ankle, and elsewhere (e.g. tibial nerve).

Modulation of Drug Delivery

The methods and systems of the current invention can be used in addition to, or as an alternative to other prior art transdermal drug delivery systems for transporting drug carriers across the skin barrier and can further be used with micro-needle or subcutaneous drug infusion in order to guide drugs to a tissue target more efficiently along an intended pathway.

Accordingly, in the current invention a patient may be selected who is experiencing a condition, symptom, or state for which the patient wishes to receive treatment. An appropriate therapy is then selected using drug regimen (e.g. dosage, area of administration, etc) which is directed and well suited towards delivery of drug to a particular tissue target. At least one IPC can then be surgically situated in a target area so that target tissue, related to modulation of the condition, is adjacent to the IPC. A drug may then be introduced to the patient so that it is located within the patient. This may occur by various methods including injection of nanoparticles. At least one stimulator may be positioned external to the patient to provide stimulation to tissue adjacent to at least one IPC. The stimulation may then be presented according to a stimulation regimen which provides for therapy to be delivered in an intended manner. Results then be assessed and the therapy adjusted if needed.

Figure 23B:
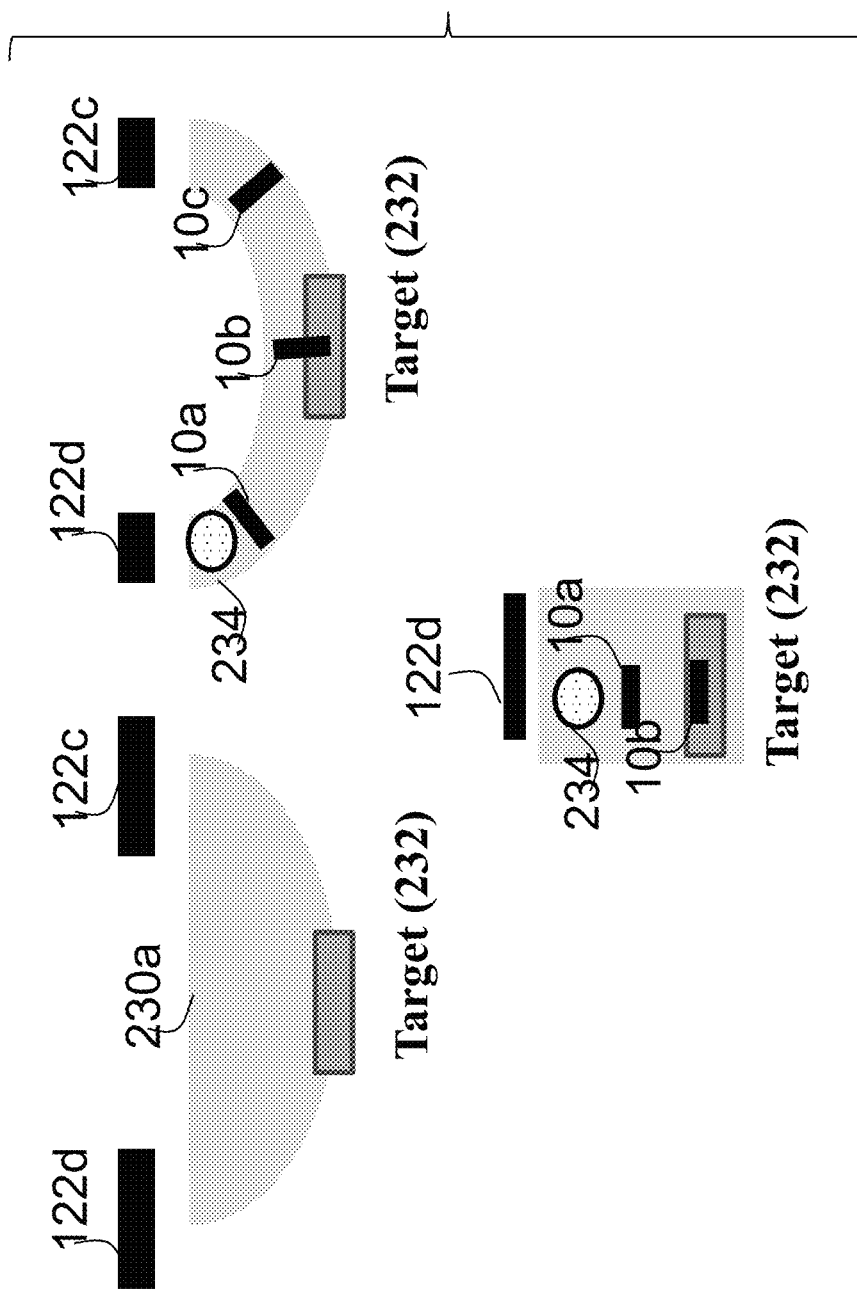
FIG. 23b is a schematic diagram of an alternative embodiment of the subject system in which a plurality of IPCs provides for the shaping of an electrical field.

As shown in FIG. 23a when two stimulators 122c, d are placed such that tissue resides between the stimulators, the unshaped electrical field 230a which arises may be somewhat wide, and may be shaped by the heterogeneous and nonlinear structures and impedances of the tissues, including skin tissue. However, by implanting at least one IPC 10a, the electrical pathway between the two stimulators may be shaped (e.g. narrowed). When multiple IPCs are used 10a, b,c then these may serve to form a conductive pathway 236, having a shaped electrical field 230b which is directed along a path and more narrow than the unshaped field 230a. In this embodiment one stimulator may be subcutaneous, percutaneous, or implanted, and the $2^{nd}$ stimulator (can be the same or other type). FIG. 23b shows a second example of both an unshaped field (left side of figure) and a shaped field (right side of figure). In this embodiment, as shown on the left side of the figure, a drug 234 is introduced into the tissue of the patient, who also has at least one IPC implanted (in the figure there are 3). Stimulation is then provided and the drug is guided in its diffusion along the shaped electrical field to the target 232 to provided improved drug delivery. The bottom portion of the figure shows a monopolar stimulator 122d and two IPCs configure to guide a drug 234 to a target 232, the return electrode is located distally and does not serve to steer the field.

Modulation and Treatment of Autonomic and Neurological Disorders.

In one embodiment, a method for modulating, suppressing or preventing a medical condition in a subject can comprising the steps of: positioning at least one IPC 10 on, or proximate to, at least one of a vidian nerve (VN), a greater petrosal nerve (GPN), a deep petrosal nerve (DPN), or a branch thereof, of the subject; and positioning a stimulator for activating the tissue around at least the one IPC 10 to apply an electrical signal to modulate the activity of at least one of the VN, the GPN, the DPN, or the branch thereof. The method can be used for a medical condition that is mediated by autonomic or neurological dysfunction. The method may include the step of stimulating, shown in block 36 of FIG. 17 to disrupt nerve signal generation in, or transmission through, at least one of the VN, the GPN, the DPN, or the branch thereof. Further, wherein the positioning step 30 occurs, it can comprise advancing the at least one IPC, without penetrating the cranium, into the pterygopalatine fossa so that the at least one IPC is positioned on or proximate to at least one of the VN or the branch thereof.

The at least one IPC and stimulator form a "stimulation pair", which means that the two components must have corresponding physical parameters which are well suited to work together, as disclosed herein, to allow the IPC to provide for targeted electrical stimulation.

In another embodiment, a method for suppressing or preventing a medical condition in a subject comprises the steps of: positioning at least one IPC 30 on or proximate to at least one tissue target including a VN, a GPN, a DPN, or a branch thereof, of a subject. The steps further include activating at least one stimulator 36 to apply an electrical field in the region around the at least one IPC to apply an electrical signal to at least one of the VN, the GPN, the DPN, or the branch thereof. The patient is selected so that the treated medical condition is selected from the group consisting of pain, movement disorders, epilepsy, cerebrovascular diseases, autoimmune diseases, sleep disorders, autonomic disorders, urinary bladder disorders, abnormal metabolic states, disorders of the muscular system, cardiovascular disorders, pulmonary disorders, inflammatory disorders, and neuropsychiatric disorders. In one embodiment, the at least one stimulator is provided 32 at a cutaneous location on the head, or within the nasal or oral openings and has a physical size that has been adjusted 32 to correspond to the size and location of the IPC 10. The at least one IPC and stimulator form a "stimulation pair".

In one embodiment, a method for suppressing or preventing a medical condition in a subject comprises the steps of: implanting at least one IPC 30 on or proximate to tissue target that is at least one of a sphenopalatine ganglion, a sphenopalatine nerve, a vidian nerve, or a branch thereof, of the patient; and supplying stimulation 36 by a stimulator that is localized so as to be sufficiently proximate to the at least one IPC 10 in order to apply an electrical signal in a targeted manner to the target. The medical condition or disorder may include symptoms of pain resulting from one or more of atypical odontalgia, cluster tic syndrome, geniculate neuralgia, occipital neuralgia and temporal arteritis. The method can further comprise the step of disrupting pain signal generation in, or transmission through, at least one tissue target by the stimulation 36. At least one of the stimulator 22 or IPC 10 can be advanced without penetrating the nasal cavity or the palate. The medical condition can also be autonomic dysfunction resulting from one or more of Holmes-Adie syndrome, orthostatic hypotension, striatonigral degeneration, vasovagal syncope, Lyme disease and autonomic instability. The medical condition can also be a neurological disorder resulting from one or more of hemifacial spasm, Melkersson-Rosenthal syndrome and Parry-Romberg syndrome.

Transcutaneous Neurostimulation for Improving Memory, Attention, and Performance as well as Treatment of Various Disorders.'

TENS systems have been used apply electrical fields to the brain in order to modulate sleep, anxiety, depression, and pain. Others are using TENS to apply electrical fields to the brain in order to modulate (e.g. improve) attention, memory, and other types of cognitive/sensory processing putatively by increasing blood flow at intracranial sites, although additional mechanisms may also be contributing to these effects. While many TENS systems use only 2 or 3 stimulators, TENS can also be applied to the brain using full-head multiple-electrode montages. TENS systems can also comprise a stimulation unit and a dedicated ear electrode for providing stimulation of the auricular branch of the vagus nerve.

As evidenced by these examples, there is a need for systems and methods that can increase nerve stimulation specificity, while avoiding disadvantages related to conventional transcutaneous, subcutaneous, and percutaneous stimulation methods. The current invention systems and methods that relate to stimulator and IPC pairs may provide for improved benefits over prior solutions, and may also be combined with some of the technology being used by current approaches.

The invention may be used in a manner relevant to wearable brain stimulation technology that enhances brain function. Transcranial electrical stimulation (TES) systems including transcanial direct current stimulation (tDCS) are relatively simple to use because they relies upon external, rather than implanted, stimulators.

In one embodiment of the invention, one IPC is affixed to the left side of the skull and one IPC is affixed to the right side of the skull. At least one stimulator is provided above each respective IPC, and serves to guide the externally applied signals towards the skull in while the IPCs decrease the dispersion of the stimulation fields in surrounding tissue. In a second embodiment, each IPC is realized as conductive member that resides within the skull, rather than simply being affixed to the surface, and which may pass entirely, or only partially through the skull. Each IPC which guides the stimulation signal towards the brain due to decreased resistance relative to surrounding tissue. Although the implantation of IPCs is invasive, it will often be much less invasive than neurosurgery and implantation of a deep brain neurostimulator. Implanation can likely be done on an outpatient basis. In a third embodiment the IPCs are positioned in the temple or frontal area as well as near the mastoid. This may allow for the provision of either lateralized stimulation (when temple-to mastoid) stimulation is used, or both posterior and anterior stimulation when both temple and mastoid stimulation occurs. Other configurations for implantation of IPCs may also be beneficial such as one IPC at the front of the head and the other near the inion, in order to provide fronto-posterior stimulation which is not lateralized. Further, the IPCs can be implanted on the surface of the cortex, and above or below and of the well-known structures of the dura, arachnoid pia matter, or within the cerebral cortex grey matter itself. At least one stimulator is situated proximate to the IPC on or near the head in order to provide enhanced transcutaneous (e.g., TENS, magnetic, TDCS or TNS) to a patient. For a patient suffering from Alzheimer disorder, or in the case of stroke or TBI patient, and the therapy is effective only with longer stimulation periods, this type of intervention may be seen as acceptably invasive.

The methods and systems of the disclosed invention can rely upon the device 400 shown in FIG. 25, in order to provide stimulation to one or more IPCs. Either fixed stimulator surfaces 402 or adjustable surfaces may be used.

Additionally, a stimulator 440 shown in FIG. 25, can be affixed the patients' scalp in order to provide stimulation over a period of time such as 1 hour or more. The stimulator 440 can have multiple electrodes 442a-442e, which serve to allow for stimulation in slightly different locations. This can be used when an IPC is implanted in order to select an electrode which provides the best stimulation coupling to the IPC. However this type of stimulator can also be used in order to accomplish several advantages when providing transcutaneous stimulation either with or without an IPC.

Firstly the array stimulator 440 can be used to provide spatial, or spatial-temporal patterns of activation which are related to the locations of the IPCs. In the case of a patient this may cause a larger area of the cortex to be treated without requiring the subject to manually move the stimulator to different locations. Over time the active electrode may be select in a spatial temporal pattern which allows for different areas of the cortex to be stimulated. Further the spatial temporal activation can occur according to the orientation of the stimulator. If the stimulator is provided in a posterior-anterior direction, then spatial-temporal patterns of activation may occur such that the cortex is stimulator in a poster-to-anterior manner. This feature can obviously be extended into many more types of beneficial stimulation patterns. The selection of spatial or spatial-temporal patterns which are beneficial to a patient can be guided by assessment of data sensed or otherwise provided by the patient.

Secondly, the stimulator 440, can be used to provide or discrete stimulation using smaller electrode contacts. Because the density of the electrical field generally becomes larger as a larger electrode is used, the ability to individually provide for discrete stimulator surfaces may increase the current density near a cortical target without simultaneously activating adjacent tissue.

When the IPC 10 is realized as and stimulus redirecting system (SRS) the electrode pickup plate may be situated outside of the skull and electrodes may route the electrical energy through an opening which has been made in the skull to an electrode that is implanted within the brain of patient.

Transvascular Biomodulation

Example tissue targets to be treated by the current invention, either using transvascular or other type of nerve modulation, may include sympathetic nerve chain of a patient and all of the associated structures and nerves in communication with the sympathetic nerve chain, such as endocrine glands including the adrenal gland, or nerves to the kidneys. In one embodiment, a method for treating a patient suffering from a pulmonary or respiratory condition comprises inserting a therapy delivery device (which may include a stimulator) into a vessel of the patient's body; advancing the therapy delivery device in the vessel to a position adjacent to an adrenal gland; deploying an IPC to a tissue target near the adrenal gland (by way of the therapy delivery device or by other means), and positioning a stimulator in order to modulate tissue in the vicinity of the IPC to deliver a therapy signal to the adrenal gland and to electrically modulate the adrenal gland to treat the patient's pulmonary or respiratory condition. The stimulator can be a implantable stimulator or a stimulator located outside of the patient, and the therapy signal is an stimulation signal that modulates the activity of the adrenal gland. The vessel can be a vein, a suprarenal vein or a tributary thereof, or an inferior vena cava or a tributary thereof. The pulmonary or respiratory condition can be asthma or chronic obstructive pulmonary disorder. The IPC can be positioned on or adjacent to an adrenal cortex, adrenal medulla, one or more neural structures that innervate the adrenal medulla. The stimulator which can provide at least one stimulation signal field in the vicinity of the IPC can be implanted in a retroperitoneal space, lower abdomen, or a vein of the patient. The stimulation can be, for example, an electrical signal that has been determined to cause differential release of epinephrine and norepinephrine, or, more specifically, to cause release of more epinephrine relative to release of norepinephrine.

In an embodiment, the invention is implemented as a method of treating a patient in which modulation of the adrenal gland is desired. The method may include inserting a therapy delivery device into a patient's body, such as vessel into a vessel of the patient and advancing the therapy delivery device to a position adjacent to an adrenal gland. The therapy device may be configured to provide stimulation to the adrenal gland in conjunction with an IPC which has been previously implanted in the patient. Alternatively the therapy device can be a catheter which is used to deliver the IPC into a location in the patient.

Tissue Modulation for Treatment of Hypertension

In an embodiment the invention of enhanced tissue modulation can be configured, to enhance, bias and/or shape an electric field including promotion of field lines extending along a path, such as the longitudinal direction of the blood vessel. The IPC 10 may be implanted in or around a carotid artery, and further may be implanted in a location in the vicinity of carotid baroreceptors. Electrical modulation of the baroreceptor can, in turn influence the heart cardiac output and vascular smooth muscle so as to influence total peripheral resistance. Baroreceptors act as part of a negative feedback system called the baroreflex and, if there is a change from a usual mean arterial blood pressure, the reflex can serve to return the pressure toward a normal level. The IPC 10 can be implanted at a location near the branching of the internal carotid artery and the external carotid artery. By modulating electrical fields in the vicinity of carotid baroreceptors the IPC may facilitate the focusing of an electric or magnetic field provided by a stimulator that is configured to modulate carotid baroreceptors and modulate the blood pressure of a subject. "Modulating" the blood pressure of a subject may include reducing, increasing, controlling, regulating, and otherwise influencing the blood pressure of a subject.

Furthermore, the IPC 10 may be configured for implantation in a blood vessel, such as carotid artery or jugular vein, in a location that, when paired with the stimulation signals provided by a stimulator, is suitable for modulation of glossopharyngeal nerve. Since the glossopharyngeal nerve innervates carotid baroreceptors, stimulation of that target may serve to modulate the blood pressure of a subject. The glossopharyngeal nerve or baroreceptor may be modulated by an IPC 10 and stimulator pair when the stimulator is located external to the patient, cutaneously, or subcutaneously. Either the IPC 10 or the stimulator can be located in a vascular or non-intravascular location. The modulation of targets within the neck related to regulation of cardiovascular tone and activity may occur simultaneously, after, or before pharmaceutical or other interventions. Thereby the systems and methods of the invention can be practiced in order to enhance or supplement other interventions.

Modulation and Control of Blood Glucose Levels.

In an embodiment, a method of glucose level control can comprise providing at least one IPC adapted to amplify, guide and direct an electric field which is provided by at least one stimulator in order to modulate the pancreas. The treatment can include applying an electric field to modulate the pancreatic activity using the at least one paired IPC and stimulator.

Systems and Methods for Using the Invention with Electrocore Technology.

The systems and methods of the disclosed invention are relevant to a series of technologies related to tissue modulation that have been disclosed by Electrocore Inc. The technologies use electrical stimulation provided by cutaneous electrical stimulation or use implanted stimulators driven by magnetically driven stimulation. In the case of cutaneous electrical stimulation, the stimulation is often provided by means of two fixed stimulators or "electrically permeable contact surfaces" termed gammacore. Although stimulator-IPC pairing may occur using the gammacore, in improved embodiments the gammacore stimulator can use stimulators that are configured to be better matched to the physical dimensions of the IPCs. This goal may also be achieved by providing stimulation templates, which are components that shape the field provided by at least 1 fixed stimulator as shown in FIGS. 23a, 23b. This goal may also be achieved using other types of stimulators which are attached to the gammacore device as disclosed herein.

For example, a system for treating a medical condition of a patient can comprise a stimulator with a housing which has at least one electrically permeable contact surface for contacting an outer skin surface of the patient. An energy source within the housing is configured to generate an electric field sufficient to transmit an electric current through the outer skin surface of the patient to a region which includes an IPC that is located proximate to a target within the patient such as a nerve. The electric current produced by the device, in combination with the effects of the IPC, is sufficient to treat the medical condition of the patient. Although the device may be used without the IPC, the addition of the IPC may provide for enhanced focus of the electrical energy towards an anatomical target and may allow for reduced stimulation amplitude in the stimulation signals at the level of the skin, and for reduced spread of the signal to regions adjacent to the IPC and target nerve. As will be disclosed the electrically permeable contact surface and IPC may be paired. In other words, they both may be configured to increase the electrical coupling of the stimulator and IPC in terms of their physical dimensions, orientations, and distances. The pairing can occur according to "Pairing rules" which have been derived empirically to produce enhanced stimulation when followed.

In an embodiment, a patient's behavioral response may be used to inform the device, patient, or doctor, that the stimulation has met some criteria related to the provision of electrical stimulation. For example, a button can be depressed by a patient when a subjective feeling such as "relief from symptoms" occurs. Further, the device can be configured to detect whether the modulation signal (e.g., electric current) is effectively modulating said nerve. This can occur using a sensor which can sense a measure such as a physiological response from the patient. For example, the stimulator can be used for directed modulation of the vagus nerve in conjunction with the IPC 10 which serves to enhance the electrical pattern provided by the stimulator (that is used to provide cutaneous stimulation to the patient) at a target proximate to the location of the IPC.

In an embodiment, the system may further by configured with a sensor that is a microphone which is configured to sense data which is processed by the processor 58 shown in FIGS. 18a,18b, in order to measure a property of the patient's voice and/or a laryngeal electromyographic signal and/or an electroglottographic signal. Further sensors can be adapted, and the processor 58 can be similarly configured, to calculate relevant measures from data obtained from the patient via the sensing module 55 and its sensors, such as a pupil diameter and/or a blood flow within an eye, electrodermal activity and/or heart rate variability, a property of the patient's autonomic nervous system, vagal artery blood flow, cerebral blood flow, an evoked potential, an electroencephalogram, and quantified electroencephalogram (QEEG), a pain threshold and/or a sway and/or a chemical within the patient's blood. In an embodiment, the sensor is an optical device configured to detect data related to the patient (e.g. oxygen in a patient's blood, or heart rate), or may be configured to detect a contrast or other measuring agent such as fluorescent material that has been applied onto or under a skin of the patient.

In an embodiment, by using at least one sensor, the device 50 can obtained the sensed data which can be processed and evaluated by the sensing and processing modules 55,58 in order to evaluate and adjust the electrical field provided by the stimulator until it is deemed sufficient, in combination with the IPC, to modulate a target in a target region such as nerve fiber. The sensed data may also be used to insure that the electric field provided by the stimulator, in the presence of the IPC, is not sufficient in its amplitude or other characteristics to substantially modulate a nerve or muscle that is not the intended target, in order to reduce or deter any unwanted side-effect.

The system can generate at least 1 stimulation signal at one or more stimulators which is configured to generate an electric field in the vicinity of the IPC proximate to a target portion of vagus nerve so that the field is above a threshold, in the presence of the IPC, for generating action potentials within A and B fibers of the vagus nerve and below a threshold for generating action potentials within C fibers of the vagus nerve.

In another embodiment, a method of testing stimulation of a branch of a vagus nerve in a patient comprises electrically stimulating the tissue near a branch of a vagus nerve of a patient in which an IPC has been implanted and having the patient vocalize a glissando. The branch of the vagus nerve can be a recurrent laryngeal nerve which has had both an IPC and stimulator pair selected, and situated suitably to allow enhanced nerve modulation to be provided to the patient. The method can further include a step in which electromyography or electroglottography is performed during the implantation of the IPC and/or positioning of the stimulator. Further an additional method comprises testing a branch of a vagus nerve in a patient by; implanting an IPC in a patient, using an external stimulator to electrically stimulate said branch of a vagus nerve; and measuring a physiological response of the patient such as the diameter of a pupil of an eye of a patient. The method can further include, measuring the absolute or relative diameters of pupils of left and right eyes of the patient, a pupil response latency, a blood flow within an eye of a patient or within both the left and right eyes of a patient. The measures can be compared using lateralization criteria, where a change, relative to a pre-stimulation baseline period, must be approximately symmetrical or asymmetrical. A measure of symmetry may be calculated by the processing module 58.

The systems and methods of the current invention can treat medical conditions, such as migraine headache, by electrically stimulating a target relatively noninvasively using an IPCs and stimulators that have been paired. The target may be at least one portion of at least one vagus nerve situated within a patient's neck. Preferred embodiments allow a patient to self-treat and/or modulate an unwanted condition, state, attribute or symptom. The system and method can assist to ensure that at least one stimulator is positioned correctly and that the amplitude and other parameters of the stimulation, in conjunction with the IPC, enable the stimulation field to be enhanced by the IPC so that the vagus nerve is modulated in an intended manner by a therapeutic waveform signal. Those methods can comprise measuring properties of the patient's larynx, pupil diameters, blood flow within an eye, electrodermal activity and/or heart rate variability as a means to evaluate, halt, or adjust a least one modulation signal.

In an embodiment, the invention may include a method of treating a headache in a patient comprises positioning a stimulator adjacent to a skin surface of a neck of the patient and implanting at least one IPC in the neck of a patient, wherein the stimulator and IPC have been paired. The stimulator is powered by one or more electrical impulses generated by the device. The electrical impulses of the stimulator works jointly with the IPC to modulate the vagus nerve of the patient to provide enhanced stimulation. In one embodiment, the electrical impulses can have a frequency of about 1,000 Hz to about 10,000 HZ and are selected to be sufficient to at least partially relieve pain associated with the headache when the stimulation is provided and the IPC is present. The method further includes using electrical stimulation impulses which, when used in conjunction with the IPC, are sufficient to generate action potentials within fibers of the vagus nerve responsible for activating neural pathways causing changes within a brain of the patient to at least partially relieve pain associated with the headache.

The method further comprises generating an electrical field and shaping the electrical field such that the electrical field, created by the IPC and stimulator is sufficient to primarily modulate the vagus nerve; and wherein the electric field is not sufficient to substantially modulate a nerve or muscle between the outer skin surface and the target region. The method can modify the transmitting step so that it is implemented by generating a magnetic field exterior to the patient which, when the IPC is present, is sufficient to induce an electrical impulse at or near the selected nerve within the patient that is more targeted than which would occur when the IPC is not present. Evidence for the influence of the IPC may include such things as less side effects, a greater number of responding patients, or the ability to stimulate with lower intensity stimuli than would occur in the absence of the IPC. In embodiments, the electrical impulses can have a frequency of a duty cycle of about 1% to about 10%. The method may use a stimulation frequency of about 4000 Hz to about 6000 Hz, or about 5000 Hz. The method may be used to treat a patient with a headache that is selected to be one of: a migraine headache or a cluster headache, or a tension headache, or a sinus headache.

In another embodiment, a method for treating or preventing a disorder in a patient, which comprises implanting an IPC on or near a vagal nerve of a patient, selecting at least one stimulator that is appropriately paired to at least one of the IPC's location and physical dimension and applying one or more electrical impulses to skin in a region near a vagus nerve of the patient according to a treatment paradigm. Patients may be selected who show response to a treatment paradigm wherein the treatment paradigm comprises approximately continuously applying the electrical impulses for a time period of about 30 seconds to about 5 minutes as a single dose. The treatment paradigm further comprises applying one or more doses on a daily basis. Further, a single dose can comprise applying the electrical impulses for a time period of about 60 seconds to about three minutes or for a time period of about 90 seconds to about 150 seconds.

Further, the method may include operating wherein the electrical impulses are not applied to the vagus nerve between each single dose or where the treatment paradigm comprises applying a single dose two to five times per day or wherein the treatment paradigm comprises applying one or more treatment sessions per day, wherein each treatment session comprises applying a single dose 2 to 4 times within an hour time period, or wherein the treatment session comprises applying a single dose twice within a 15 minute time period, or wherein each single dose is applied within 5 minutes of each other. Some patients may be selected who are classified as being More Resistant. More Resistant patients can receive therapy with a) more intense stimulation signals b) longer or more frequent stimulation sessions c) stimulation that is provided by an additional stimulator and IPC pairing, and d) concurrent pharmaceutical treatment given before, after, or concurrently with the stimulation treatment.

In one embodiment, patients are first provided with therapy using a stimulator and no IPC, and those who are found to be refractory are implanted with an IPC for providing enhanced stimulation to the vagus nerve.

In another embodiment, only patients having a body mass index (BMI) which is over a certain amount may be implanted with an IPC, while other patients with a BMI below a certain amount are not implanted with an IPC.

In another embodiment, only patients having a skin +fat +target distance (SFTD) which is over a certain amount may be implanted with an IPC, while other patients with a SFTD below a certain amount are not implanted with an IPC. In other words, for some patients, the distribution of skin, fat, and target tissue may serve to make cutaneous stimulation non-effective or less effective than desired and the use of at least one IPC can provide enhanced stimulation which is sufficiently effective to produce a desired change within the patient.

Systems and methods for using the invention with implantable vagus nerve stimulators.

The systems and methods of the disclosed invention are relevant to a series of technologies related to tissue modulation that have been disclosed by Cyberonics Inc. The technologies use electrical stimulation provided by implanted electrical stimulation devices, some of which are implanted stimulators driven by magnetic stimulation or wireless power sources which are external to the patient. The disclosed invention may be used in addition to, or as an alternative to, fully implantable vagus nerve stimulators, and may be used before or after implantation of a partially or fully implantable system. The disclosed invention may also be used as a screener technology which can identify appropriate candidates for different types of chronically implanted systems such as disclosed in FIG. 22*b* and associated text.

In one embodiment, a method for using a neurostimulation system for managing bradycardia through vagus nerve stimulation, comprises an implantable IPC configured to enhance electrical therapeutic stimulation provided by an external stimulator in a manner that results in creation and propagation in both afferent and efferent directions of action potentials within neuronal fibers of a cervical vagus nerve of a patient. The system can further comprises a recordable memory 60 configured to store an operating mode of for a treatment regimen that is operated by a processor 58 to control a pulse generator of the signal generator module 62 connected to the at least one stimulator 88. The treatment regimen may comprise parametrically defined maintenance doses of the electrical therapeutic stimulation which have been adjusted and tuned to restore cardiac autonomic balance through application of the treatment regimen. The treatment regimen may include stimulation parameters that produce stimulation signal patterns such as continuously-cycling, intermittent and periodic electrical pulses. The under control of the processor 58, the pulse generator of the signal generator module 62 (also known as a signal generator) is configured to therapeutically deliver the maintenance doses to the at least one stimulator in order to modulate the vagus nerve via an electrically coupled nerve stimulation therapy IPC 10. The therapy regimen may be configured to deliver the therapy independent of cardiac cycle. Additionally, sensing module 54 and a sensor such as a physiological sensor can be configured to monitor the patient to obtain sensed data relevant to the patient's physiology can also be used. Upon processing the sensed data and detecting a condition indicative of bradycardia, the treatment regimen can be configured to cause the device to suspend the delivery of the maintenance doses by the pulse generator of the signal generator module 62. The system may also include a treatment regimen that is configured to cause the processor 58 to wait a progressively increasing amount of time, each progressively increasing amount of time having a time period greater than a time period of an initial delay, and, upon detecting a condition indicative of an absence or termination of the bradycardia after suspension of the delivery of the maintenance doses, the processor 58 may be configured to then resume delivery of progressively increasing partial maintenance doses to the stimulator in order to deliver electrical field stimulation to an area near the vagus nerve via which is further directed to a specific portion of the vagus nerve by means of the IPC. The therapy regimen may be further configured so that each progressively increasing partial maintenance dose has a duty cycle that is less than a duty cycle of a full maintenance dose. In an embodiment, the neurostimulator comprises sensing and processing modules to detect physiological markers of abnormally slow sinus rhythm as indicative of bradycardia, and this detection is specified as part of the operating mode of the therapy regimen that is stored in the recordable memory. The system can further use the electrode sensor to monitor the patient's sinus rhythm and the processor 58 is further configured to, upon sensing of the physiological markers of abnormally slow sinus rhythm, trigger the suspension of the delivery of the maintenance dose by the pulse generator of the signal generator module 62. The above disclosed method may be provided as a therapy, or may be provided as a screening method which is provided during a screening period in order to determine if the patient is a suitable candidate for the implantation of a chronic system.

In an embodiment a method of treating an individual suffering from a brain disorder such as epilepsy comprises providing stimulation to a site comprising a volume of neural tissue in an area of the individual's brain selected from the group consisting of insula, subcallosal area, cingulate, thalamus, prefrontal cerebral cortex, mesial temporal lobe, cerebellum, hypothalamus, hippocampus, amygdala, brain stem, occipital lobe, temporal lobe, frontal lobe, parietal lobe, Wernicke's area, area tempestas, basal ganglia, globus pallidus, superior colliculus, stratum, ventral striatum, ventral pallidum, caudate nucleus, putamen, nucleus accumbens, substantia nigra, ventral tegmentum, Brodmann areas 24, 25, 32, piriform cortex, ventricular region, ventral pallidum, and forebrain circumventricular organs, reticulate substantia nnominate, rostral midbrain, red nucleus, periaqueductal gray, and/or white matter tracts leading to an aforementioned area or nucleus. In embodiments, the brain stimulator may be external or implanted and may stimulate a neural target directly or may be coupled to at least one IPC located in a target brain region.

In this manner said combination of at least first and second modulation attenuates at least one type of brain symptom such as an epilepsy symptom and/or deter recurrence of an epileptic event. The method includes selecting and adjusting a second stimulation signal which causes sufficient stimulation of a site on the vagus nerve when the IPC is present, that at least one vagus nerve pathway or neural activating circuit is affected in a manner that is desirable to the patient and which serves as a goal of the stimulation. The method may cause a responsive effect on neural activity in at least one area of the brain to further attenuate the same or different epilepsy symptom and/or to further deter recurrence of an epileptic event. The method may also be modified to only provide stimulation at the Vagus nerve, or to provide stimulation at the vagus nerve at times that are different than, prior to, or after other types of tissue modulation. Of course the stimulation can be provided in addition to pharmaceutical therapy.

Using an implantable system for brain stimulation and an external system for Vagal stimulation provides various advantages. Firstly, the electrode configuration is less complicated and the implanted medical device does not have to send stimulation electrodes to both the brain and vagus target. This provides benefits to both the patient (e.g., better comfort) and the implanting physician (e.g. less complexity). Secondly, this configuration will can save power in the implantable device since external power is being applied. Thirdly, using the IPC will provide for better therapy and less refractory cases.

In one embodiment, a medical system for treating an epileptic patient comprises: an external stimulator and device operative when activated for generating selected electrical waveforms representing preprogrammed therapy regimens to control epileptic seizures; an implantable IPC adapted for placement on or near a selected cranial nerve; the stimulator and IPC configured for providing selected said therapy regimens to modulate the electrical field near a preselected cranial nerve of the patient and thereby modulate electrical activity of the selected nerve in a manner which is predetermined to control seizures. The device may be further configured with a sensor, and a processor which operates a sensing subsystem for detecting time rate of change of the patient's heart rate from cardiac activity sensed by the sensor, and which is configured to provide stimulation responsive to detection of a sudden time rate of change of heart rate which is inconsistent with normal physical activity of the patient, as being indicative of an impending seizure, for automatically activating the electronic means to generate a selected one of the therapy regimens for application of a stimulation signal to the stimulator, whereby a desired stimulus is provided to modulate the selected cranial nerve. The sensing system is configured to include an algorithm for assessing the time rate of change of detected cardiac activity relative to a preset threshold slope indicative of an impending seizure. The above disclosed method may be provided as a therapy, or may be provided as a screening method which is provided during a screening period in order to determine if the patient is a suitable candidate for the implantation of a chronic system.

Systems and Methods for Using the Invention with Cerbomed-Like Technology.

In one embodiment, an apparatus for transcutaneous stimulation of the skin of a human comprises a housing configured to fit completely in a pinna of the human and a stimulation unit, housed within the housing, configured to produce an electronic stimulation signal. The system also has electronic controls (which may be realized in the form of a processor and stimulation module), housed in the housing, which are configured to control the transcutaneous stimulation. The system provides a first curved section having a proximal end and a distal end wherein the proximal end of the first curved section is attached to one end of the housing; a second curved section having a proximal end and a distal end, wherein the proximal end of the second curved section is attached to the other end of the housing, each of the curved sections having a spring action for securing the housing and the curved sections in the pinna. This configuration allows two stimulators to be strategically positioned to provide therapeutic stimulation using a first electrode stimulator that is mounted at the distal end of the first curved section and a second electrode stimulator that is mounted at the distal end of the second curved section, separated by a distance D. The first and second electrode stimulators are electrically connected to the electronic controls in order to apply electrical stimulation to the patient's skin. In a preferred embodiment the distance D between the two electrodes are configured in accordance with the physical dimensions (e.g. length) of an IPC that has been implanted in the patient, and are also configured to promote the alignment of at least one edge of an electrode and the IPC. The pairing between the two electrodes and the IPC allows for enhanced stimulation of a particular target with less diffusion of the field into nearby areas. The apparatus may use electrodes that are spherically shaped, and are situated so that at least the first electrode has an edge that is configured to reside over an edge of the IPC. The housing and electrode stimulators of the apparatus can be designed so that the electrodes rest in a region of, or near a target and proximate to the IPC, and the electrodes are designed so that the electrodes are situated on the skin above the IPC which has been implanted proximate to an area of the vagus nerve and/or a region near the tragus and or/in a region or above or below the cutaneous afferences of the vagus nerve (nervus vagus).

In an embodiment, the invention is used to stimulate an auricular acupuncture point by implanting an IPC proximate to a target that is known to treat a symptom by serving as an acupuncture target and then providing stimulation using electrode stimulators that have been configured, shaped, and spaced in order to provide for enhanced stimulation as a method of electro-acupuncture.

Modulation for Spinal Cord Stimulation and for Inhibition of Pain.

Although the enhanced stimulation technology of the current invention can be used in many areas of the body and/or head to treat disorders (such as headache or trigeminal allodynia known as "facial pain") and to deter, modulate, and decrease pain signals and the resulting experience of pain, spinal stimulation may be considered a primary candidate area for the technology.

In an embodiment, a method for providing selective high-frequency spinal cord modulation for inhibiting pain with reduced side-effects includes providing high-frequency modulation in the range of about 1.5 KHz to about 50 KHz to a stimulator applied either cutaneously or subcutaneously to the patient's spinal cord region to address low back pain, while also positioning at least one IPC near the target tissue in order to deter creating unwanted sensory and/or motor side-effects.

In one embodiment, the stimulator (e.g., an electrode) is placed near a primary spinal target and one or more IPCs may be implanted in adjacent targets to steer the field provided at the primary target. Accordingly, rather than needing to provide multiple wires, a single stimulator may be implanted and one or more IPCs may be implanted within sufficient distances from the stimulator that multiple targets may be modulated by providing stimulation at the electrode site. Multiple IPCs may also be configured in order to guide stimulation provided cutaneously by one or more stimulators in order to increase TENS therapy. The above disclosed method may be provided as a therapy, or may be provided as a screening method which is provided during a screening period in order to determine if the patient is a suitable candidate for the implantation of a chronic system. In various embodiments spinal cord stimulation may be provided using different frequencies, stimulation regimens, number of stimulators and IPCs, shapes of stimulators and IPCs, provided that the system follows the principles disclosed herein so that enhanced stimulation is provided.

A method of using enhanced transcutaneous electrical nerve stimulation to modulate a target in the neck can also be used to modulate at least one gland of a patient. For example, the method can include the first step of implanting, within the patient, at least one IPC proximate to at least one gland of the patient, the IPC having a length L and a distal edge and proximal edge. The method can also include providing at least one stimulation signal to the patient from a stimulator located outside of the patient which is configured with at least one edge aligned with at least one of the distal and proximal edge of the IPC.

In one embodiment, the providing of at least one stimulation signal to the patient from a tissue stimulator located outside of the patient which is configured with at least one edge aligned with at least one of the distal and proximal edge of the IPC, includes at least both of the distal and proximal edge of the IPC. In this embodiment of the method, the gland can be the thyroid gland. In this case the IPC can be located proximate to at least one of a patient's two thyroid glands, or two IPCs can be implanted for each thyroid gland. Stimulation which is provided by the external stimulator can be designed to modulate the thyroid gland in order to increase or decrease the amount of thyroxin produced by the gland. Alternatively, the stimulation can serve to provide modulation that increases, decreases, or otherwise modulates the physiological activity or metabolism of the gland. The stimulation can be intended for the treatment of a thyroid disorder, unwanted state, or complication. The treatment can also be for obesity.

In other embodiments of the invention, other sites which are appropriate for the IPCs can be: supraclavical, subclavical, cervical, subscapular (underneath the scapulae), surrounding kidney/renal cortex, paraspinal, and major blood vessels. Although some sites are difficult to provide corresponding transcutaneous stimulation with surface stimulation, these can be accessible by transvascular or other method of stimulation. The transvascular approach would be beneficial for certain applications such as if the therapy only involved monthly or other long-interval stimulation protocols.

Modulation of Nerves Related to Acupuncture Sites.

The IPC can be implanted at any site in the ear, that is used in acupuncture or electro-acupuncture in order to provide an increase in targeted therapy. It should be understood, that any site used in acupuncture or electro-acupuncture to stimulate tissue so as to effect a change in a patient, can be more specifically activated by use of an IPC and paired stimulator in order to effect a similar change as providing acupuncture at that site.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

The various steps disclosed herein (such as, for non-limiting example, logic that performs a function or process) may be described as data and/or instructions embodied in various computer-readable media, in terms of their behavioral, and/or other characteristics. The logic and methods described herein may comprise, according to various embodiments of the invention, software, hardware, or a combination of software and hardware.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. When the word "or" is used in reference to a list of two or more items, that word covers all of the following interpretations of the word: any of the items in the list, all of the items in the list and any combination of the items in the list.

The above descriptions of illustrated embodiments of the system, methods, or devices are not intended to be exhaustive or to be limited to the precise form disclosed. While specific embodiments of, and examples for, the system, methods, or devices are described herein for illustrative purposes, various equivalent modifications are possible within the scope of the system, methods, or devices, as those skilled in the relevant art will recognize. The teachings of the system, methods, or devices provided herein can be applied to other processing systems, methods, or devices, not only for the systems, methods, or devices described.

In general, in the following claims, the terms used should not be construed to limit the system, methods, or devices to the specific embodiments disclosed in the specification and the claims, but should be construed to include all systems that operate under the claims.

While preferred embodiments of the present invention have been shown and described herein, it will be obvious to those skilled in the art that such embodiments are provided by way of example only. Numerous variations, changes, and substitutions will now occur to those skilled in the art without departing from the invention.

What is claimed is:

1. A method of providing treatment of a pelvic floor disorder comprising:
   providing a neurostimulator configured for providing at least one stimulation signal to at least one stimulator located external to a patient with a pelvic floor disorder;
   establishing at least one field shaping element for said stimulator, said field shaping element configured for adjusting a shape of at least one stimulation field of the stimulation signal to provide targeted stimulation of a saphenous nerve of the patient; and,
   operationally activating the neurostimulator, adapted to provide a stimulation signal to the saphenous nerve in a lower limb of the patient, the signal having a stimulus characteristic configured to treat the pelvic floor disorder by stimulation of the saphenous nerve.

2. The method of claim 1 wherein the pelvic floor disorder is an overactive bladder disorder.

3. The method of claim 1 wherein the at least one stimulator is at least one electric stimulator.

4. The method of claim 3 wherein establishing at least one field shaping element comprises providing a stimulation template configured with a ridge defining a shape that retains electroconductive gel within the shape.

5. The method of claim 3 wherein the at least one field shaping element is at least one of: a stimulation template having at least two layers that are electrically non-conductive for at least a portion of their geometry and flank an electrically conductive layer sandwiched therebetween, or an electrically conductive material having an upper side facing the stimulator and a lower side facing the nerve of the patient wherein each side is coated on at least a portion of a side surface with a non-conductive film.

6. The method of claim 3 wherein said at least one field shaping element which is configured for adjusting the shape of the stimulation field of the at least one stimulator includes a plurality of at least two additional stimulators which are electrode stimulators, and said field shaping includes defining a set of at least two stimulators to be selectively activated to provide a stimulation pattern.

7. The method of claim 3 wherein said at least one field shaping element that is configured for adjusting the shape of the stimulation field of the at least one stimulator includes a shaping electrode grid containing at least three grid elements, wherein at least two sets of grid elements are selectively activated to provide at least two patterns of stimulation and wherein each of said grid elements has an associated optical indicator to provide a visual indication of which of said grid elements are activated.

8. The method of claim 3 wherein said at least one field shaping element is configured for adjusting the shape of the stimulation field of the at least one stimulator and includes a shaping electrode grid that is divided into a plurality of electrically conductive elements each of which being selectively attached to at least one connector of a signal generator.

9. The method of claim 8 wherein the electrically conductive elements are each separated from the other by electrically non-conductive surfaces of said at least one field shaping element.

10. The method of claim 3 wherein said at least one field shaping element includes a stimulation template that includes an electrode grid having a set of conductive contacts selectively activated to cause alignment between an edge formed by the selectively activated electrically conductive elements and a portion of an implantable electrically conductive element.

11. The method of claim 1 wherein establishing at least one field shaping element comprises providing a stimulation template formed of an electrically non-conductive material portion and an electrically conductive material portion wherein said electrically non-conductive portion limits the region of the stimulator surface that stimulates a portion of the skin of the patient.

12. The method of claim 1 wherein establishing at least one field shaping element comprises establishing a stimulation template which is an adhesive element having an electrically conductive region and an electrically non-conductive region, said electrically conductive region having a predetermined shape which permits passage of said stimulation signal in a predetermined pattern, said adhesive element having a pair of opposing adhesive element surfaces selected from the group of: one of said opposing adhesive surfaces being configured to_be releasably attached to a skin surface of the patient, one of said opposing adhesive element surfaces being configured to be releasably attached to said stimulator, respective opposing adhesive element surfaces being realeasably attached to said stimulator and the skin surface of the patient.

13. The method of claim 1 wherein establishing at least one field shaping element comprises providing a stimulation template having at least one adhesive surface that is at least partially electrically non-conductive.

14. The method of claim 1 wherein establishing at least one field shaping element includes providing a stimulation template having a predetermined shape that provides for the passage of energy which is a function of a physical dimension of an implantable electrically conductive element.

15. The method of claim 1 wherein establishing at least one field shaping element includes providing a stimulation template having a portion that is adapted to be shaped according to the patient's anatomical data.

16. The method of claim 1 wherein establishing at least one field shaping element is a stimulation template adapted to be shaped according to imaging data of the patient.

17. The method of claim 1 wherein establishing at least one field shaping element includes providing a stimulation template adapted to be configured according to assessment of the patients feedback provided during a procedure that determines an area on the surface of the patient's skin where stimulation is determined to be successful in stimulating a target nerve.

18. The method of claim 1 wherein said at least one field shaping element which is configured for adjusting the shape of the stimulation field of the at least one stimulator includes a shaping electrode grid containing at least three grid elements having fixed positions, of which at least two are selectively activated to provide at least two different stimulation patterns.

19. The method of claim 1 wherein at least one of a set of shaping parameter values are defined for the at least 3 grid elements of an electrode grid, and are stored in memory and retrieved to provide a selected stimulation field shape.

20. The method of claim 1 wherein the at least one stimulator is one of at least 3 stimulators provided on a surface substrate that provides a fixed geometry of stimulation, and a set of shaping parameter values are defined for the at least 3 stimulators to enable the neurostimulator to operate at least one stimulus generator to provide at least two stimulation field shapes.

21. The method of claim 1 wherein the at least one stimulator is at least one magnetic stimulator located external to the patient.

22. The method of claim 1 wherein the at least one stimulator is at least one sonic stimulator.

* * * * *